US012595510B2

(12) United States Patent
Baribaud et al.

(10) Patent No.: US 12,595,510 B2
(45) Date of Patent: Apr. 7, 2026

(54) METHODS AND COMPOSITIONS FOR PREDICTION OF RESPONSE TO A THERAPY OF AN INFLAMMATORY BOWEL DISEASE

(71) Applicant: JANSSEN BIOTECH, INC., Horsham, PA (US)

(72) Inventors: Frederic Baribaud, Broomall, PA (US); Carrie Brodmerkel, West Chester, PA (US); Xilin Li, Wallingford, PA (US); Takahiro Sato, Philadelphia, PA (US); Shannon Telesco, Lansdale, PA (US); Feifei Yang, Wayne, PA (US); Prerak Desai, Lansdale, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 1165 days.

(21) Appl. No.: 17/292,926

(22) PCT Filed: Nov. 14, 2019

(86) PCT No.: PCT/US2019/061459
§ 371 (c)(1),
(2) Date: May 11, 2021

(87) PCT Pub. No.: WO2020/102519
PCT Pub. Date: May 22, 2020

(65) Prior Publication Data
US 2022/0002805 A1 Jan. 6, 2022

Related U.S. Application Data

(60) Provisional application No. 62/767,636, filed on Nov. 15, 2018.

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/106* (2013.01); *C12Q 2600/158* (2013.01)

(58) Field of Classification Search
CPC ..................... C12Q 2600/106; G01N 2800/52
See application file for complete search history.

(56) References Cited

U.S. PATENT DOCUMENTS

| | | | | |
|---|---|---|---|---|
| 5,739,282 A | * | 4/1998 | Colotta ................... | A61P 35/02 |
| | | | | 536/23.5 |
| 2005/0272080 A1 | | 12/2005 | Palma et al. | |
| 2007/0157325 A1 | | 7/2007 | Mojtahedian | |
| 2009/0054253 A1 | | 2/2009 | Li et al. | |
| 2010/0069256 A1 | | 3/2010 | Baribaud et al. | |
| 2015/0010544 A1 | | 1/2015 | Ariaans et al. | |
| 2016/0304969 A1 | | 10/2016 | Ayers et al. | |
| 2017/0145044 A1 | | 5/2017 | Hudson et al. | |

FOREIGN PATENT DOCUMENTS

| | | | | | |
|---|---|---|---|---|---|
| JP | 2012501452 A | 1/2012 | | | |
| JP | 2019501133 A | 1/2019 | | | |
| JP | 2020501699 A | 1/2020 | | | |
| WO | WO 2010025340 A2 | 3/2010 | | | |
| WO | WO 2010/062663 | * | 6/2010 | ............. | G01N 33/50 |
| WO | WO 2017091544 A1 | 6/2017 | | | |
| WO | WO 2018112232 A1 | 6/2018 | | | |

OTHER PUBLICATIONS

Kuboyama, Kurume Med J 45:33-37, 1998.*
Wils et al, Clin Gastroenterol Hepatol 14:242-250, epub 2015.*
Arijs et al., 2009, "Mucosal gene signatures to predict response to infliximab in patients with ulcerative colitis," Gut, 58(12):1612-1619.
Callahan et al., 2016, "DADA2: High-resolution sample inference from Illumina amplicon data," Nat. Methods, 13(7):581-583 and Online Methods (7 pages).
ClinicalTrials.gov No. NCT01863771, "A Safety and Effectiveness Study of Golimumab in Japanese Patients With Moderately to Severely Active Ulcerative Colitis," first posted: May 29, 2013, last updated: Apr. 5, 2017 (9 pages).
ClinicalTrials.gov No. NCT01988961, "A Study to Evaluate the Accuracy of a Subset of the Length-109 Probe Set Panel (a Genetic Test) in Predicting Response to Golimumab in Participants With Moderately to Severely Active Ulcerative Colitis," first posted: Nov. 20, 2013, last updated: Jan. 5, 2017 (11 pages).
Ferrante et al., 2007, "Predictors of early response to infliximab in patients with ulcerative colitis," Inflamm. Bowel Dis., 13(2):123-128.
Hajian-Tilaki, 2013, "Receiver Operating Characteristic (ROC) Curve Analysis for Medical Diagnostic Test Evaluation," Caspian J. Intern. Med., 4(2):627-635.
Hanley et al., 1982, "The meaning and use of the area under a receiver operating characteristic (ROC) curve," Radiology, 143(1):29-36.
Hanzelmann et al., 2013, "GSVA: gene set variation analysis for microarray and RNA-seq data," BMC Bioinformatics, 14:7 (15 pages).
Hibi et al., 2017, "Efficacy and safety of golimumab 52-week maintenance therapy in Japanese patients with moderate to severely active ulcerative colitis: a phase 3, double-blind, randomized, placebo-controlled study—(PURSUIT-J study)," J. Gastroenterol., 52(10):1101-1111.

(Continued)

*Primary Examiner* — Mark Halvorson
(74) *Attorney, Agent, or Firm* — JONES DAY

(57) ABSTRACT

Biomarkers that are indicative of the response to the therapy of the inflammatory bowel disease, including ulcerative colitis (UC) and Crohn's disease (CD), are described. Also described are probes capable of detecting the biomarkers and related methods and kits for predicting the response to the therapy of the inflammatory bowel disease.

14 Claims, 5 Drawing Sheets
Specification includes a Sequence Listing.

(56) References Cited

OTHER PUBLICATIONS

International Search Report and Written Opinion for International Patent Application No. PCT/US2019/061459 (Pub No. WO 2020102519) mailed Feb. 11, 2020 (19 pages).

Irizarry et al., 2003, "Exploration, normalization, and summaries of high density oligonucleotide array probe level data," Biostatistics, 4(2):249-264.

Kolho et al., 2015, "Fecal Microbiota in Pediatric Inflammatory Bowel Disease and Its Relation to Inflammation," Am. J. Gastroenterol., 110(6):921-930 and Supplemental Materials (13 pages).

Kozich et al., 2013, "Development of a dual-index sequencing strategy and curation pipeline for analyzing amplicon sequence data on the MiSeq Illumina sequencing platform," Appl. Environ. Microbiol., 79(17):5112-5120.

Lewis et al., 1997, "Stool form scale as a useful guide to intestinal transit time," Scand J. Gastroenterol., 32(9):920-924.

Li et al., 2018, "Molecular Comparison of Adult and Pediatric Ulcerative Colitis Indicates Broad Similarity of Molecular Pathways in Disease Tissue," J. Pediatr. Gastroenterol. Nutr., 67(1):45-52.

Liberzon et al., 2015, "The Molecular Signatures Database (MSigDB) hallmark gene set collection," Cell Syst., 1(6):417-425 and Supplemental Information (20 pages).

Love et al., 2014, "Moderated estimation of fold change and dispersion for RNA-seq data with DESeq2," Genome Biol., 15(12):550 (21 pages).

McMurdie eta 1., 2013, "phyloseq: an R package for reproducible interactive analysis and graphics of microbiome census data," PLoS One, 8(4):e61217 (11 pages).

Ritchie et al., 2015, "limma powers differential expression analyses for RNA-sequencing and microarray studies," Nucleic Acids Res., 43(7):e47 (13 pages).

Rutgeerts et al., 2009, "Biological therapies for inflammatory bowel diseases," Gastroenterology, 136(4):1182-1197.

Sandborn et al., 2014, "Subcutaneous golimumab induces clinical response and remission in patients with moderate-to-severe ulcerative colitis," Gastroenterology, 146(1):85-95; quiz e14-5 and Supplemental Materials (Epub 2013) (32 pages).

Shaw et al., 2016, "Dysbiosis, inflammation, and response to treatment: a longitudinal study of pediatric subjects with newly diagnosed inflammatory bowel disease," Genome Med., 8(1):75 (13 pages).

Telesco et al., 2018, "Gene Expression Signature for Prediction of Golimumab Response in a Phase 2a Open-Label Trial of Patients With Ulcerative Colitis," Gastroenterology, 155(4):1008-1011.e8 (12 pages).

Travis et al., 2012, "Developing an instrument to assess the endoscopic severity of ulcerative colitis: the Ulcerative Colitis Endoscopic Index of Severity (UCEIS)," Gut, 61(4):535-542 (Epub 2011).

Wang et al., 2007, "Naive Bayesian classifier for rapid assignment of rRNA sequences into the new bacterial taxonomy," Appl. Environ. Microbiol., 73(16):5261-5267.

West et al., 2017, "Oncostatin M drives intestinal inflammation and predicts response to tumor necrosis factor-neutralizing therapy in patients with inflammatory bowel disease," Nat. Med., 23(5):579-589 and Online Methods (14 pages).

Zhou et al., 2018, "Gut Microbiota Offers Universal Biomarkers across Ethnicity in Inflammatory Bowel Disease Diagnosis and Infliximab Response Prediction," mSystems, 3(1):e00188-17 (14 pages).

* cited by examiner

FC>2, FDR<0.05

METHODS AND COMPOSITIONS FOR PREDICTION OF RESPONSE TO A THERAPY OF AN INFLAMMATORY BOWEL DISEASE

CROSS-REFERENCE TO RELATED APPLICATIONS

This application is a U.S. National Stage Application under 35 U.S.C. § 371 of International Patent Application No. PCT/US2019/061459, filed Nov. 14, 2019, which claims the benefit of U.S. Provisional Application No. 62/767,636, filed Nov. 15, 2018, the disclosure of each of which is incorporated by reference herein in its entirety.

FIELD OF THE INVENTION

The present invention is directed generally to the prediction of response to a therapy of an inflammatory bowel disease in a subject, and provides methods, reagents, and kits useful for this purpose. Provided herein are a panel of biomarkers that are indicative of the response to the therapy of the inflammatory bowel disease, including ulcerative colitis and Crohn's disease, probes capable of detecting the panel of biomarkers and related methods and kits for predicting the response to the therapy of the inflammatory bowel disease. Also provided herein are a panel of biomarkers that are indicative of the response to combination therapies for treating inflammatory bowel disease.

SEQUENCE LISTING

This application contains a sequence listing, which is submitted electronically via EFS-Web as an ASCII formatted sequence listing with a file name of "14620-004-228_SEQ_LISTING.txt" and a creation date of Oct. 31, 2019 and having a size of 13,976 bytes. The sequence listing submitted via EFS-Web is part of the specification and is herein incorporated by reference in its entirety.

BACKGROUND OF THE INVENTION

Inflammatory bowel disease (IBD) is a chronic disease with uncontrolled inflammation of the gastrointestinal system, with Crohn's disease (CD) and ulcerative colitis (UC) representing the two main subtypes of disease. The treatment options for patients with IBD greatly improved with the introduction of biologics, which has decreased the incidence of hospital visits and surgeries (Rutgeerts, et al., Gastroenterology, 2009, 136: 1182-1197). However, even biologics such as golimumab (anti-TNF therapy) demonstrate clinical non-responder rates as high as 50% (Sandborn, et al., Gastroenterology, 2014, 146: 85-95; quiz e14-15). As new drugs with distinct mechanisms of action become available, an ability to identify subsets of patients with distinct responses to different anti-inflammatory therapies could be beneficial in many ways, including reduced exposure of patients to ineffective treatments, achievement of higher response rates, and the ability to treat predicted non-responder patients with alternative therapies and combination therapies to avoid stepping through less effective treatments.

To this end, many previous studies have identified candidate biomarkers for prediction of response to anti-TNF therapy in IBD. (Arijs, et al., Gut., 2009, 58: 1612-1619; Kolho, et al., Am. J. Gastroenterol., 2015, 110: 921-930; Shaw, et al., Genome Med., 2016, 8: 75; Ferrante, et al., Inflamm. Bowel Dis., 2007, 13: 123-128; Zhou, et al., mSystems, 2018, 3; West et al., Nat. Med., 2017, 23:579-589). However, all of these studies are limited in their clinical utility since they either used small sample sizes or were not prospectively validated in an independent cohort.

Thus, it is desirable to develop biomarkers that predict response to the IBD treatment, identify responder and/or non-responder patients, preferably before the subject is treated with the disease. Likewise, there remains a general need to develop biomarkers that predict response to combination therapies for IBD. The biomarkers can also be used for other purposes, such as to serve to stratify patients in clinical trials.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

The present invention relates to the prediction of response to a therapy of an inflammatory bowel disease in a subject, and provides methods, reagents, and kits useful for this purpose.

In one aspect, provided herein is a method of predicting a response of a subject diagnosed with an inflammatory bowel disease (IBD) to an anti-interleukin (IL) treatment of the IBD, the method comprising:

a. contacting a sample from a subject with a set of probes capable of detecting a panel of biomarkers comprising 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3); and b. determining a pattern of the panel of biomarkers; wherein the pattern of the panel of biomarkers predicts the response to the anti-IL treatment in the subject.

In other embodiments, the panel of biomarkers provided herein comprises CMTM2, C5AR1, FGF2, GK, HGF, IL1RN, LILRA2, NAMPT, PAPPA, SNCA, SOD2, STEAP4, and ZBED3.

In some embodiments, the sample is obtained before the subject is treated with the anti-IL treatment.

In certain embodiments, the probe provided herein is selected from the group consisting of an aptamer, an antibody, an affibody, a peptide, and a nucleic acid. In one embodiment, the probe is a nucleic acid. In other embodiments, the probe is selected from the group consisting of SEQ ID NOS. 1-14, SEQ ID NO. 17, SEQ ID NO. 20, SEQ ID NO. 23, SEQ ID NO. 26, SEQ ID NO. 29, SEQ ID NO. 32, SEQ ID NO. 35, SEQ ID NO. 38, SEQ ID NO. 41, SEQ ID NO. 44, SEQ ID NO. 47, and SEQ ID NO. 50.

In some embodiments, the pattern of the panel of biomarkers provided herein is determined by: (a) determining the baseline gene expression levels of the panel of biomarkers in the subject, and (b) determining the signature score for each sample.

In certain embodiments, the gene expression levels are determined by quantitative polymerase chain reaction (qPCR). In other embodiments, the qPCR primers are selected from the group consisting of SEQ ID NO. 15, SEQ ID NO. 16, SEQ ID NO. 18, SEQ ID NO. 19, SEQ ID NO. 21, SEQ ID NO. 22, SEQ ID NO. 24, SEQ ID NO. 25, SEQ ID NO. 27, SEQ ID NO. 28, SEQ ID NO. 30, SEQ ID NO. 31, SEQ ID NO. 33, SEQ ID NO. 34, SEQ ID NO. 36, SEQ ID NO. 37, SEQ ID NO. 39, SEQ ID NO. 40, SEQ ID NO. 42, SEQ ID NO. 43, SEQ ID NO. 45, SEQ ID NO. 46, SEQ ID NO. 48, SEQ ID NO. 49, SEQ ID NO. 51, and SEQ ID NO. 52.

In some embodiments, the subject is predicted to be a responder to the anti-interleukin (IL) treatment of the IBD if the signature score of the panel of biomarkers is above a pre-specified threshold indicative of response. In some embodiments, the pre-specified threshold level is selected from the group consisting of between −3.9000 and 1.1000. In some embodiments, the pre-specified threshold level is −3.8234. In some embodiments, the pre-specified threshold level is 1.0000.

In another aspect, provided herein is a method of predicting a response of a subject diagnosed with an inflammatory bowel disease (IBD) to a JAK inhibitor (JAKi) treatment of the IBD, the method comprising:
  a. contacting a sample from a subject with a set of probes capable of detecting a panel of biomarkers comprising 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyl-transferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3); and
  b. determining a pattern of the panel of biomarkers;
  wherein the pattern of the panel of biomarkers predicts the response to the JAKi treatment in the subject.

In some embodiments, the sample is obtained before the subject is treated with the JAKi treatment.

In some embodiments, the subject is predicted to be a responder to the JAKi treatment of the IBD if the signature score of the panel of biomarkers is above a pre-specified threshold indicative of response. In some embodiments, the pre-specified threshold level is selected from the group consisting of between −3.9000 and 1.1000. In some embodiments, the pre-specified threshold level is −3.8234. In some embodiments, the pre-specified threshold level is 1.0000.

In still another aspect, provided herein is a method of predicting a negative response of a subject diagnosed with an inflammatory bowel disease (IBD) to an anti-inflammatory treatment of the IBD, the method comprising:
  a. contacting a sample from a subject with a set of probes capable of detecting a panel of biomarkers comprising 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyl-transferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);
  b. determining baseline gene expression levels of the panel of biomarkers in the sample; and
  c. determining the signature score for each sample;
  wherein the subject is predicted to be a non-responder to the anti-inflammatory treatment of the IBD if the signature score of the panel of biomarkers is below a pre-specified threshold indicative of non-response.

In one aspect, provided herein is a method of predicting a negative response of a subject diagnosed with an inflammatory bowel disease (IBD) to an anti-inflammatory treatment of the IBD, the method comprising:
  a. contacting a sample from a subject with a set of probes capable of detecting a panel of biomarkers consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phospho-ribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);
  b. determining baseline gene expression levels of the panel of biomarkers in the sample by quantitative polymerase chain reaction (qPCR); and
  c. determining the signature score for each sample;
  wherein the subject is predicted to be a non-responder to the anti-inflammatory treatment of the IBD if the signature score of the panel of biomarkers is below a pre-specified threshold indicative of non-response.

In some embodiments, the sample is obtained before the subject is treated with the anti-inflammatory treatment.

In certain embodiments, the method provided herein further comprises administering to the subject one or more of the anti-inflammatory treatment of the IBD.

In some embodiments, the non-responder subjects have one of more of the characteristics selected from the group consisting of high disease burden, microbial dysbiosis, and high levels of inflammatory activity.

In other embodiments, the non-responder subjects are identified as candidates for combination therapy.

In one aspect, the combination therapy provided herein comprises two or more therapies selected from the group consisting of anti-inflammatory treatment, antibiotics, immunomodulators, anti-diarrheal medications, pain relievers, iron supplements, and calcium and vitamin D supplements.

In another aspect, the combination therapy provided herein comprises administering to the subject one or more agents targeting one or more canonical pathways selected from the group consisting of granulocyte adhesion and diapedesis, agranulocyte adhesion and diapedesis, osteoarthritis pathway, role of macrophages, fibroblasts and endothelial cells in rheumatoid arthritis, hepatic fibrosis and hepatic stellate cell activation, inhibition of matrix metallo-proteases, atherosclerosis signaling, bladder cancer signaling, role of pattern recognition receptors in recognition of bacteria and viruses, and HMGB1 signaling.

In some embodiments, the anti-inflammatory treatment provided herein is an anti-tumor necrosis factor (TNF) treatment, a JAK inhibitor (JAKi) treatment, or an anti-interleukin (IL) treatment. In some embodiments, the anti-inflammatory treatment is an anti-IL-23 or anti-IL-12/23 treatment. In other embodiments, the anti-IL treatment is ustekinumab. In some embodiments, the anti-inflammatory treatment is the JAK inhibitor treatment. In other embodiments, the anti-inflammatory treatment is the anti-TNF treatment. In some embodiments, the anti-TNF treatment is golimumab.

In one aspect, provided herein is a method of treating a subject diagnosed with an inflammatory bowel disease (IBD), comprising:

a. predicting the response of the subject to an anti-inflammatory treatment of the IBD, comprising:
  (i) contacting a sample from a subject with a set of probes capable of detecting a panel of biomarkers comprising 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3); and
  (ii) determining a pattern of the panel of biomarkers; wherein the pattern of the panel of biomarkers predicts the response to the anti-inflammatory treatment in the subject; and
b. administering the subject a therapeutically effective amount of one or more anti-inflammatory treatment.

In further embodiments, the subject is predicted to be a responder to the anti-inflammatory treatment of the IBD if the signature score of the panel of biomarkers is above a pre-specified threshold indicative of response. In some embodiments, the pre-specified threshold level is selected from the group consisting of between −3.9000 and 1.1000. In some embodiments, the pre-specified threshold level is −3.8234. In some embodiments, the pre-specified threshold level is 1.0000.

In another aspect, provided herein is a method of treating a subject diagnosed with an inflammatory bowel disease (IBD), comprising:

a. predicting the subject to be a non-responder to an anti-inflammatory treatment of the IBD, comprising:
  (i) contacting a sample from a subject with a set of probes capable of detecting a panel of biomarkers comprising 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);
  (ii) determining baseline gene expression levels of the panel of biomarkers in the sample; and
  (iii) determining the signature score for each sample; wherein the subject is predicted to be a non-responder to the anti-inflammatory treatment of the IBD if the signature score of the panel of biomarkers is below a pre-specified threshold indicative of non-response; and
b. administering the subject a therapeutically effective amount of one or more anti-inflammatory treatment.

In further embodiments, the panel of biomarkers for the method of treating the subject provided herein, includes CMTM2, C5AR1, FGF2, GK, HGF, IL1RN, LILRA2, NAMPT, PAPPA, SNCA, SOD2, STEAP4, and ZBED3. In some embodiments, the sample is obtained before the subject is treated with the anti-inflammatory treatment. In certain embodiments, the probe provided herein is selected from the group consisting of an aptamer, an antibody, an affibody, a peptide, and a nucleic acid. In one embodiment, the probe is a nucleic acid. In other embodiments, the probe is selected from the group consisting of SEQ ID NOS. 1-14, SEQ ID NO. 17, SEQ ID NO. 20, SEQ ID NO. 23, SEQ ID NO. 26, SEQ ID NO. 29, SEQ ID NO. 32, SEQ ID NO. 35, SEQ ID NO. 38, SEQ ID NO. 41, SEQ ID NO. 44, SEQ ID NO. 47, and SEQ ID NO. 50. In some embodiments, the pattern of the panel of biomarkers provided herein is determined by: (a) determining the baseline gene expression levels of the panel of biomarkers in the subject, and (b) determining the signature score for each sample. In certain embodiments, the gene expression levels are determined by quantitative polymerase chain reaction (qPCR). In other embodiments, the qPCR primers are selected from the group consisting of SEQ ID NO. 15, SEQ ID NO. 16, SEQ ID NO. 18, SEQ ID NO. 19, SEQ ID NO. 21, SEQ ID NO. 22, SEQ ID NO. 24, SEQ ID NO. 25, SEQ ID NO. 27, SEQ ID NO. 28, SEQ ID NO. 30, SEQ ID NO. 31, SEQ ID NO. 33, SEQ ID NO. 34, SEQ ID NO. 36, SEQ ID NO. 37, SEQ ID NO. 39, SEQ ID NO. 40, SEQ ID NO. 42, SEQ ID NO. 43, SEQ ID NO. 45, SEQ ID NO. 46, SEQ ID NO. 48, SEQ ID NO. 49, SEQ ID NO. 51, and SEQ ID NO. 52.

In a further embodiment, the predicted non-responder subjects are identified as candidates for combination therapy. Provided herein is a method of treating a subject diagnosed with an inflammatory bowel disease (IBD), comprising predicting the subject to be a non-responder to an anti-inflammatory treatment of the IBD and administering the subject a combination therapy comprising two or more therapies selected from the group consisting of anti-inflammatory treatment, antibiotics, immunomodulators, anti-diarrheal medications, pain relievers, iron supplements, and calcium and vitamin D supplements. In a further embodiment, the combination therapy comprises administering to the subject one or more agents targeting one or more canonical pathways selected from the group consisting of granulocyte adhesion and diapedesis, agranulocyte adhesion and diapedesis, osteoarthritis pathway, role of macrophages, fibroblasts and endothelial cells in rheumatoid arthritis, hepatic fibrosis and hepatic stellate cell activation, inhibition of matrix metalloproteases, atherosclerosis signaling, bladder cancer signaling, role of pattern recognition receptors in recognition of bacteria and viruses, and HMGB1 signaling.

In some embodiments, the anti-inflammatory treatment provided herein for the method of treating the subject diagnosed with IBD, is an anti-tumor necrosis factor (TNF) treatment, a JAK inhibitor (JAKi) treatment, or an anti-interleukin (IL) treatment. In some embodiments, the anti-inflammatory treatment is an anti-IL-23 or anti-IL-12/23 treatment. In other embodiments, the anti-IL treatment is ustekinumab. In some embodiments, the anti-inflammatory treatment is the JAK inhibitor treatment. In other embodiments, the anti-inflammatory treatment is the anti-TNF treatment. In some embodiments, the anti-TNF treatment is golimumab.

In certain embodiments, the method provided herein further comprises predicting the response by one or more other characteristics of the subject. In other embodiments, the other characteristics are selected from the group consisting of protein levels, gut microbiome, histology and clinical characteristics of the subject.

In some embodiments, the method provided herein further comprises measuring the response at or after week 6, 30 or 50 of the treatment, or anytime in between.

In one aspect, the sample is a tissue sample or a blood sample.

In one aspect, the IBD is at least one of ulcerative colitis (UC) or Crohn's disease (CD).

In some embodiments, the subject had previously failed or were intolerant of at least one therapy selected from the group consisting of: vedolizumab, corticosteroids, azathioprine (AZA), and 6 mercaptopurine (6 MP), or the subject had demonstrated corticosteroid dependence.

In one aspect, provided herein is a kit for predicting a response to a treatment in a subject diagnosed with an inflammatory bowel disease (IBD), wherein the kit comprises a set of isolated probes capable of detecting a panel of biomarkers comprising at least 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In another aspect, the kit provided herein comprises a set of isolated probes capable of detecting all biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In some embodiments, the kit further comprises a therapeutic agent.

Further aspects, features and advantages of the present invention will be better appreciated upon a reading of the following detailed description of the invention and claims.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

DETAILED DESCRIPTION OF THE INVENTION

Figure 1:
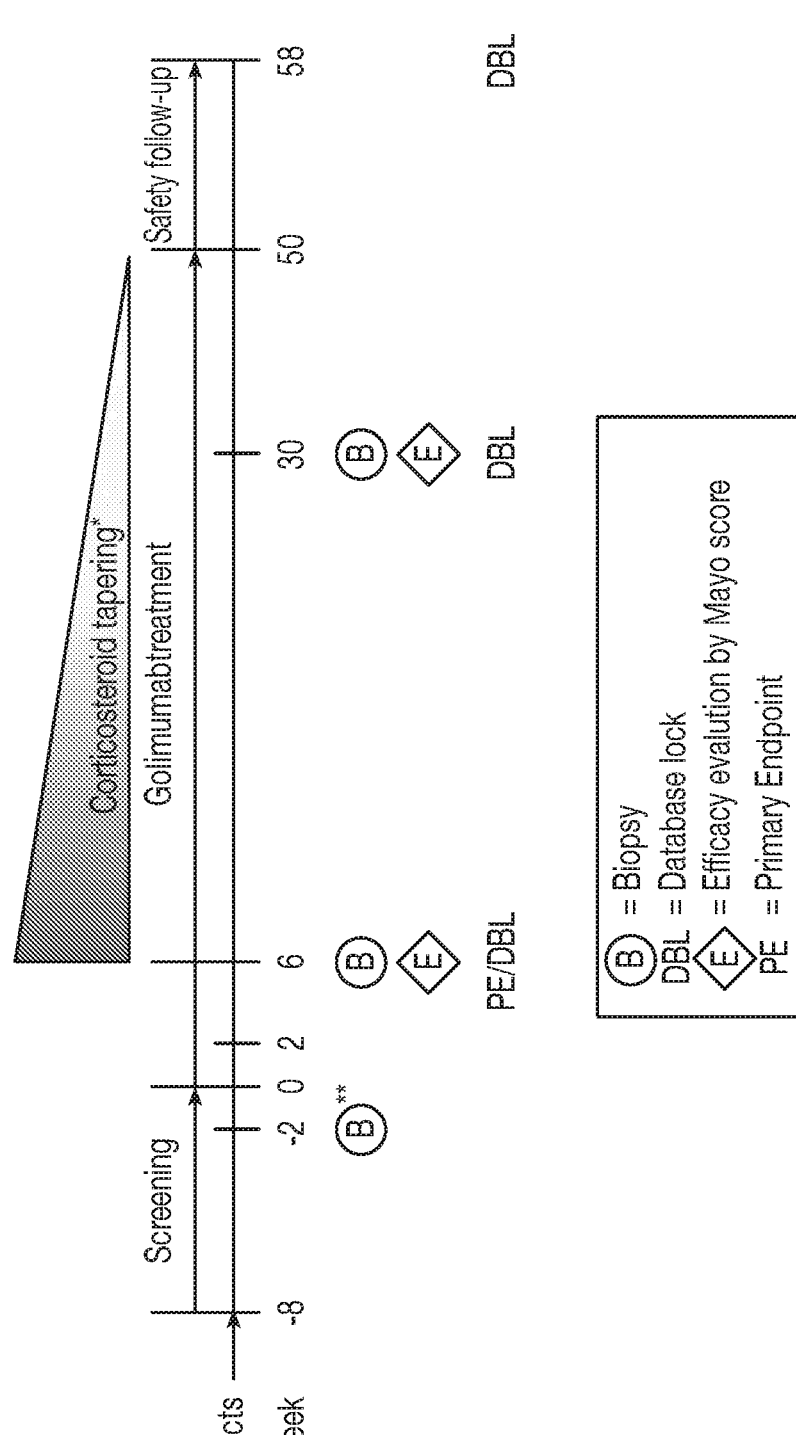
FIG. 1 is the PROgECT (Telesco S E, et al., Gastroenterology, 2018 October, 155(4):1008-1011.e8; and Clinical Trials.gov no. is NCT01988961)) study diagram showing treatment and endpoint timelines.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide, or a portion thereof.

As used herein, "biomarker" refers to a gene or protein whose level of expression or concentration in a sample is altered compared to that of a normal or healthy sample or is indicative of a condition. The biomarkers disclosed herein are genes and/or proteins whose expression level or concentration or timing of expression or concentration correlates with the prognosis of an inflammatory bowel disease (e.g., ulcerative colitis and/or Crohn's disease).

The terms "polypeptide" and "protein," as used interchangeably herein, refer to a polymer of three or more amino acids in a serial array, linked through peptide bonds. The term "polypeptide" includes proteins, protein fragments, protein analogues, oligopeptides, and the like. The term "polypeptide" as used herein can also refer to a peptide. The amino acids making up the polypeptide may be naturally derived, or may be synthetic. The polypeptide can be purified from a biological sample. The polypeptide, protein, or peptide also encompasses modified polypeptides, proteins, and peptides, e.g., glycopolypeptides, glycoproteins, or glycopeptides; or lipopolypeptides, lipoproteins, or lipopeptides.

The term "antibody," "immunoglobulin," or "Ig" as used interchangeably herein, encompasses fully assembled antibodies and antibody fragments that retain the ability to specifically bind to the antigen. Antibodies provided herein include, but are not limited to, synthetic antibodies, monoclonal antibodies, polyclonal antibodies, recombinantly produced antibodies, multispecific antibodies (including bispecific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above.

As used herein, "probe" refers to any molecule or agent that is capable of selectively binding to an intended target biomolecule. The target molecule can be a biomarker, for example, a nucleotide transcript or a protein encoded by or corresponding to a biomarker. Probes can be synthesized by one of skill in the art, or derived from appropriate biological preparations, in view of the present disclosure. Probes can be specifically designed to be labeled. Examples of molecules that can be utilized as probes include, but are not limited to, RNA, DNA, proteins, peptides, antibodies, aptamers, affibodies, and organic molecules.

As used herein, a "baseline gene expression" of a gene in a subject refers to the gene expression level of the gene in the subject before the subject is treated with an IBD treatment.

An mRNA that is "upregulated" is generally increased upon a given treatment or condition. An mRNA that is "downregulated" generally refers to a decrease in the level of expression of the mRNA in response to a given treatment or condition. In some situations, the mRNA level can remain unchanged upon a given treatment or condition. An mRNA from a patient sample can be "upregulated" when treated with a drug, as compared to a non-treated control. This upregulation can be, for example, an increase of about 5%, about 10%, about 20%, about 30%, about 40%, about 50%, about 60%, about 70%, about 80%, about 90%, about 100%, about 200%, about 300%, about 500%, about 1,000%, about 5,000%, or more of the comparative control mRNA level. Alternatively, an mRNA can be "downregulated", or expressed at a lower level, in response to administration of certain compounds or other agents. A downregulated mRNA can be, for example, present at a level of about 99%, about 95%, about 90%, about 80%, about 70%, about 60%, about 50%, about 40%, about 30%, about 20%, about 10%, about 1%, or less of the comparative control mRNA level.

Similarly, the level of a polypeptide or protein biomarker from a patient sample can be increased when treated with a drug, as compared to a non-treated control. This increase can be about 5%, about 10%, about 20%, about 30%, about 40%, about 50%, about 60%, about 70%, about 80%, about 90%, about 100%, about 200%, about 300%, about 500%, about 1,000%, about 5,000%, or more of the comparative control protein level. Alternatively, the level of a protein biomarker can be decreased in response to administration of certain compounds or other agents. This decrease can be, for example, present at a level of about 99%, about 95%, about 90%, about 80%, about 70%, about 60%, about 50%, about 40%, about 30%, about 20%, about 10%, about 1%, or less of the comparative control protein level.

The terms "subject" and "patient" may be used interchangeably. As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human. In one embodiment, the subject is a mammal, e.g., a human, diagnosed with a disease or disorder. In another embodiment, the subject is a mammal, e.g., a human, at risk of developing a disease or disorder.

As used herein, "sample" is intended to include any sampling of cells, tissues, or bodily fluids in which expression of a biomarker can be detected. Examples of such samples include, but are not limited to, biopsies, smears, blood, lymph, urine, saliva, or any other bodily secretion or derivative thereof. Blood can, for example, include whole blood, plasma, serum, or any derivative of blood. Samples can be obtained from a subject by a variety of techniques, which are known to those skilled in the art.

As used herein, "treatment" refers to both therapeutic treatment and prophylactic or preventative measures, wherein the object is to prevent or slow down (lessen) the targeted pathologic condition or disorder. Those in need of treatment include those diagnosed with the disorder as well as those prone to have the disorder (e.g., a genetic predisposition) or those in whom the disorder is to be prevented. The terms "prevent," "preventing," and "prevention" refer to reducing the likelihood of the onset (or recurrence) of a disease, disorder, condition, or associated symptom(s).

As used herein, "a response" to a treatment in a subject diagnosed with an inflammatory bowel disease (IBD) can be a positive response or a negative response to the treatment. As used herein, a "positive response" to an IBD treatment refers to a response comprising at least one of mucosal healing, clinical response, and clinical remission resulting from the IBD treatment. Mucosal healing is defined as an absolute Mayo endoscopy subscore of 0 or 1. A clinical response is defined as a decrease from baseline in the total Mayo score of at least 3 points and at least ≥30%, with an accompanying decrease from the baseline in the subscore for rectal bleeding of at least 1 point or an absolute subscore for rectal bleeding of 0 or 1. A clinical remission is defined as a total Mayo score of 2 points or lower, with no individual subscore exceeding 1 point. For example, a positive response to a IBD treatment can be a complete mucosal healing and histologic normalization, including a Mayo endoscopic subscore of 0 or 1 and a grade of 0 or 1 on the Geboes histological scale for ulcerative colitis (UC). As used herein, a "negative response" or "no response" to an IBD treatment refers to there is no response in any of mucosal healing, clinical response, and clinical remission resulting from the IBD treatment.

As used herein, "a responder" means a subject who has a positive response to an IBD treatment.

As used herein, "a non-responder" means a subject who has no response or negative response to an IBD treatment. For example, a non-responder can have no clinical response to the IBD treatment and the non-responder can have endoscopic subscore of 2 or 3 and a grade of 4 or 5 on the histological scale.

A clinical response to an IBD treatment can be indicated by an improvement in an index of disease activity, by amelioration of clinical symptoms or by any other measure of disease activity. Once such index of disease is the ulcerative colitis (UC) Mayo score. The Mayo score is an established, validated disease activity index for mild, moderate, and severe ulcerative colitis (UC) that is calculated as the sum of the 4 subscores of stool frequency, rectal bleeding, findings of endoscopy, and physician's global assessment (PGA), and ranges from 0-12. A score of 3 to 5 points indicates mildly active disease, a score of 6 to 10 points indicates moderately active disease, and a score of 11 to 12 points indicates severe disease. The partial Mayo score, which is the Mayo score without the endoscopy subscore, is calculated as the sum of stool frequency, rectal bleeding, and physician's global assessment subscores, and ranges from 0 to 9. The modified Mayo score, which is the Mayo score without the PGA subscore, is calculated as the sum of the stool frequency, rectal bleeding, and endoscopy subscores, and ranges from 0 to 9. Other disease activity indexes for UC include for example, Ulcerative Colitis Endoscopic Index of Severity (UCEIS) score and the Bristol Stool Form Scale (BSFS) score. The UCEIS score provides an overall assessment of endoscopic severity of UC, based on mucosal vascular pattern, bleeding, and ulceration (Travis et al., Gut. 61:535-542 (2012)). The score ranges from 3 to 11 with a higher score indicating more severe disease by endoscopy. The BSFS score is used to classify the form (or consistency) of human feces into 7 categories (Lewis and Heaton, Scand J Gastroenterol. 32(9):920-924 (1997)).

The term "administering" with respect to the methods of the invention, means a method for therapeutically or prophylactically preventing, treating or ameliorating a syndrome, disorder or disease (e.g., an inflammatory bowel disease (IBD)) as described herein. Such methods include administering an effective amount of said therapeutic agent at different times during the course of a therapy or concurrently in a combination form. The methods of the invention are to be understood as embracing all known therapeutic treatment regimens.

The term "effective amount" or "therapeutically effective amount" means that amount of active compound or pharmaceutical agent, a combination of therapeutic compounds or pharmaceutical compositions thereof provided herein, that elicits the biological or medicinal response in a tissue system, animal or human, that is being sought by a researcher, veterinarian, medical doctor, or other clinician, which includes preventing, treating or ameliorating a syndrome, disorder, or disease being treated, or the symptoms of a syndrome, disorder or disease being treated (e.g., IBD).

As used herein, the term "targeting" means inhibiting, modulating, upregulating, downregulating, enhancing or binding. As used herein, an "agent targeting a pathway" refers to an agent inhibiting, modulating, upregulating, downregulating, enhancing or binding to one or more known member(s) of the pathway.

As used herein, "STEAP4" refers to STEAP4 metalloreductase. STEAP4 is also known in the art as Tumor Necrosis Factor, Alpha-Induced Protein, Six-Transmembrane Epithelial Antigen Of Prostate, TNFAIP9, STAMP2, or Tumor Necrosis-Alpha-Induced Adipose-Related Protein.

As used herein, "CMTM2" refers to CKLF-like MARVEL transmembrane domain containing 2. CMTM2 is also known in the art as Chemokine-Like Factor Superfamily Member 2, CKLFSF2, or CKLF-Like MARVEL Transmembrane Domain Containing 2.

As used herein, "C5AR1" refers to complement C5a receptor 1. C5AR1 is also known in the art as C5a Anaphylatoxin Chemotactic Receptor 1, Complement Component 5a Receptor 1, C5a-R, C5R1, C5AR, Complement Component 5 Receptor 1, CD88 Antigen, or CSA.

As used herein, "FGF2" refers to fibroblast growth factor 2. FGF2 is also known in the art as Heparin-Binding Growth Factor 2, HBGF-2, FGF-2, BFGF, FGFB, Basic Fibroblast Growth Factor, or Prostatropin.

As used herein, "GK" refers to glycerol kinase. GK is also known in the art as ATP:Glycerol 3-Phosphotransferase, Glycerokinase, GK1, or GKD.

As used herein, "HGF" refers to hepatocyte growth factor. HGF is also known in the art as Fibroblast-Derived Tumor Cytotoxic Factor, Lung Fibroblast-Derived Mitogen, Hepatopoietin-A, Scatter Factor, HPTA, SF, Deafness, Autosomal Recessive 39, DFNB39, F-TCF, or HGFB.

As used herein, "IL1RN" refers to interleukin 1 receptor antagonist. IL1RN is also known in the art as IL1 Inhibitor, ICIL-1RA, IL1F3, IL1RA, IRAP, Intracellular Interleukin-1 Receptor Antagonist, or Type II Interleukin-1 Receptor Antagonist.

As used herein, "LILRA2" refers to leukocyte immuno-globulin like receptor A2. LILRA2 is also known in the art as Leukocyte Immunoglobulin-Like Receptor, Subfamily A (With TM Domain), Member 2, Leukocyte Immunoglobu-lin-Like Receptor 7, CD85 Antigen-Like Family Member H, Immunoglobulin-Like Transcript 1, Leucocyte Ig-Like Receptor A2, ILT1, LIR7, or CD85h Antigen.

As used herein, "NAMPT" refers to nicotinamide phos-phoribosyltransferase. NAMPT is also known in the art as Visfatin, PBEF1, or Pre-B-Cell Colony Enhancing Factor 1.

As used herein, "PAPPA" refers to pappalysin 1. PAPPA is also known in the art as Insulin-Like Growth Factor-Dependent IGF Binding Protein-4 Protease, Differentially Placenta 1 Expressed Protein, Aspecific BCL2 ARE-Binding Protein 2, IGF-Dependent IGFBP-4 Protease, Pregnancy-Associated Plasma Protein A, ASBABP2, or DIPLA1.

As used herein, "SNCA" refers to synuclein alpha. SNCA is also known in the art as PARK1, NACP, Parkinson Disease (Autosomal Dominant, Lewy Body) 4, Non A4 Component Of Amyloid Precursor, Non A-Beta Component Of AD Amyloid, Truncated Alpha Synuclein, or PARK4.

As used herein, "SOD2" refers to superoxide dismutase 2, mitochondrial. SOD2 is also known in the art as Superoxide Dismutase 2, Epididymis Secretory Sperm Binding Protein, Manganese-Containing Superoxide Dismutase, Indophe-noloxidase B, or Mn-SOD.

As used herein, "ZBED3" refers to zinc finger BED-type containing 3. ZBED3 is also known in the art as Axin-Interacting Protein.

Diagnosis of IBD

Inflammatory bowel diseases (IBD), such as ulcerative colitis (UC) and Crohn's disease (CD), are chronic inter-mittent diseases that lead to structural damage of the bowel wall. In UC, the inflammation is limited to the mucosa and extends from the rectum proximally. CD can be located in any part of the gastrointestinal tract and is characterized by transmural inflammation and complications.

The first clue in making a diagnosis of IBD are the symptoms, including unrelenting diarrhea, blood and/or mucus in the stool (more common with UC than CD), fever, and abdominal pain. The diagnosis of IBD is usually con-firmed by blood tests, endoscopic procedures and imaging procedures.

Blood Tests

Examples of blood tests are CBC count such as the white blood cell (WBC) count and the red blood cell (RBC) count, an electrolyte panel, liver function tests, and a fecal occult blood test (also called stool guaiac or hemoccult test). A high WBC count may be a sign that there is inflammation somewhere in the body. A low RBC count could be a sign that there is bleeding somewhere in the body (if not obvious from visible blood in the stool) or even show how much blood has been lost when compared to a prior RBC count level.

An electrolyte panel measures the level of sodium, potas-sium, chloride, and carbon dioxide in the body. Chronic diarrhea may cause these electrolytes to get to abnormally low levels.

Liver function tests (LFTs) measure alanine transaminase (ALT), aspartate transaminase (AST), alkaline phosphatase (ALP), albumin, total protein, and total and direct bilirubin levels. Abnormal levels may be caused by malnutrition because the gastrointestinal tract is not absorbing nutrients as it should.

A fecal occult blood test (also called stool guaiac or hemoccult test) is used to examine stool for traces of blood that cannot be seen with the naked eye. Stool can also be tested for the presence of a bacterial infection that could cause symptoms.

Endoscopic Procedures

An endoscopy is a procedure in which the doctor uses specialized instruments to view and operate on the internal organs and vessels of the patient body. It allows surgeons to see problems within the body without making large inci-sions. Endoscopies fall into different categories, based on the area of the body investigated.

A colonoscopy is an endoscopic procedure used to exam-ine the inside of the colon which can go beyond the areas a sigmoidoscopy can reach. A colonoscopy is useful in detect-ing colon cancer, ulcers, inflammation, and other problems in the colon. Biopsies can also be taken during a colonos-copy and examined for clues in making a diagnosis.

A sigmoidoscopy is an endoscopic procedure that is used to examine the last third of the large intestine, which includes the rectum and sigmoid colon. This test can be used to check for cancer, abnormal growths (polyps), inflamma-tion, and ulcers.

An upper endoscopy is used to see inside the esophagus, stomach, and duodenum (first section of the small intestine). It may be used to find the source of swallowing problems, nausea, vomiting, reflux, bleeding, indigestion, abdominal pain, or chest pain.

Capsule endoscopy is sometimes used to help diagnose Crohn's disease involving the small intestine. The patient swallows a capsule that has a camera in it. The images are transmitted to a recorder, after which the capsule exits the body painlessly with the stool. An endoscopy with a biopsy may still be needed to confirm a diagnosis of Crohn's disease.

Imaging Procedures

The common imagining procedure used for the diagnosis of IBD include X-rays, computerized tomography (CT) scan, and magnetic resonance imaging (MRI).

X-rays are quick, cheap, non-invasive, and an X-ray of the abdomen can show if the bowel is narrowed, obstructed, or dilated. Barium enema (also called a lower gastrointestinal series) is a special type of X-ray that uses barium sulfate and air to outline the lining of the rectum and colon. The results can show polyps, tumors, or diverticulosis. An upper gas-trointestinal (upper GI) series is a type of X-rays used to examine the esophagus, stomach, and duodenum (the first section of the small intestine). Sometimes it is used to examine the small intestine.

A CT scan is a special X-ray technique that provides more detail than a standard X-ray does. This test looks at the entire bowel as well as at tissues outside the bowel. CT enterog-raphy is a special CT scan that provides better images of the small bowel. This test has replaced barium X-rays in many medical centers.

An MRI scanner uses a magnetic field and radio waves to create detailed images of organs and tissues. An MRI is particularly useful for evaluating a fistula around the anal area (pelvic MM) or the small intestine (MR enterography). Unlike a CT, there is no radiation exposure with an MRI.

Treatment of IBD

In inflammatory bowel disease (IBD) treatment, a thera-peutic agent can reduce the inflammation that triggers the signs and symptoms, leading not only to symptom relief but also to long-term remission and reduced risks of complica-tions. IBD treatment usually involves either drug therapy or surgery. The drugs for IBD therapy include, but are not limited to, anti-inflammatory drugs, antibiotics, immuno-modulators, anti-diarrheal medications, pain relievers, iron supplements, and calcium and vitamin D supplements.

Anti-Inflammatory Drugs

Anti-inflammatory treatments are often the first step in the treatment of IBD. Anti-inflammatory drugs include, but are not limited to, aminosalicylates, corticosteroids, anti-tumor necrosis factor (TNF) agents, JAK inhibitors, anti-inter-leukin agents, and anti-integrin agents.

Examples of anti-TNF drugs include infliximab (Remi-cade), adalimumab (Humira), and golimumab (Simponi). JAK inhibitors can be the inhibitors against one or more of four JAK members: JAK1, Jak2, JAK3, and TYK2. Example of JAK inhibitors include filgotinib, peficitinib, tofacitinib (Xeljanz/Jakvinus), and upadacitinib. Anti-inter-leukin (IL) agents can be anti-IL-1, anti-IL-6, anti-IL-10, anti-IL-13, anti-IL-17, anti-IL-12/23, or anti-IL-23 agents. Anti-IL-12/23 agents are also called IL-12/23 blockade, including ustekinumab (Stelara). Examples of anti-IL-23 include BI 655066, briakinumab, guselkumab, tildraki-zumab, and ustekinumab (Stelara). Examples of anti-integ-rin drugs include vedolizumab and natalizumab.

Aminosalicylates, given orally or rectally, can help con-trol the inflammation of IBD by delivering a compound containing 5-aminosalicylic acid (5-ASA) to the bowel. Examples of aminosalicylates are sulfasalazine, mesala-mine, olsalazine and balsalazide. These medications are used for both ulcerative colitis and Crohn's disease; how-ever, they are much more effective for ulcerative colitis and are being used less often for Crohn's disease.

Corticosteroids are fast-acting anti-inflammatory drugs, which are used to treat acute (sudden onset and/or short duration) flare-ups. Because of their known side effects, doctors like to either avoid them completely or prescribe them for a short time. Corticosteroids can be given orally, rectally or intravenously. Examples of corticosteroids are prednisone, prednisolone, or methylprednisolone. Budes-onide is a slightly different type of steroid, as very little gets absorbed into the body, so side effects are much less frequent.

Antibiotics

Antibiotics, given orally or intravenously, are used selec-tively in patients with Crohn's disease and in patients with IBD who develop infection with *Clostridium difficile*. Examples of antibiotics are metronidazole and ciprofloxa-cin.

Immunomodulators

It is believed that IBD is caused by an overactive immune system. Immunomodulators work by quieting down the immune system, helping to reduce inflammation. They can be given orally or by injection. Examples of immunomodu-lators are azathioprine (AZA), cyclosporine, 6-mercaptopu-rine (6 MP), and methotrexate (for Crohn's disease).

Combination Therapies

One or more therapies included above as well as other IBD therapies well known in the art can be used in combi-nation to treat a patient with IBD. One or more therapies can be administered prior to, concurrently with, or subsequent to the administration of the other therapy described herein. Administration of one or more therapies and an additional therapy to a patient can occur simultaneously or sequentially by the same or different routes of administration. The suitability of a particular route of administration employed for a particular therapy will depend on the therapy itself. Routes of administration for the therapies for IBD are known to those of ordinary skill in the art. See, e.g., *Physicians' Desk Reference.*

In certain embodiments, the combination therapies described herein can be cyclically administered to a patient with IBD. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

As used herein, the term "in combination" does not restrict the order in which therapies (e.g., prophylactic and/or therapeutic agents) are administered to a patient with IBD. In one embodiment, a first therapy is administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before) the administration of a second therapy provided herein. In one embodiment, a first therapy is administered concomitantly with the administration of a second therapy provided herein. In one embodiment, a first therapy is administered subse-quent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy provided herein.

Various therapies can be used in combination, including any of the exemplified therapies described above. Combi-nation therapy can include two or more therapies selected from the group consisting of anti-inflammatory treatment, antibiotics, immunomodulators, anti-diarrheal medications, pain relievers, iron supplements, and calcium and vitamin D supplements.

Combination therapies can include, but is not limited to, for instance, administration of two or more anti-inflamma-tory drugs to the same subject, administration of one or more anti-inflammatory drug in combination with one or more antibiotic to the same subject, administration of one or more anti-inflammatory drug in combination with one or more immunomodulator to the same subject, administration of one or more immunomodulator in combination with one or more antibiotic to the same subject, and administration of one or more immunomodulators in combination with one or more antibiotics and one or more anti-inflammatory drugs to the same subject. Given the teachings and guidance pro-vided herein one skilled in the art will understand that the disclosure herein is intended to include all combinations and permutations of two or more IBD therapies. Thus, the various combinations and permutations set forth herein is intended to be exemplary and not limiting.

Combination therapies can also include administering to the subject one or more agents targeting one or more cellular or signaling pathways in combination with one or more immunomodulatory, one or more antibiotic, and one or more anti-inflammatory drugs. Exemplary pathways include granulocyte adhesion and diapedesis. Exemplary agents targeting granulocyte adhesion and diapedesis include, but are not limited to, C5AR, ERM, ICAM1, ICAM2, VCAM, Mac1, LFA1, Itg alpha 9, and Itg beta 1. Agents targeting granulocyte adhesion and diapedesis are well known in the art.

Exemplary pathways include agranulocyte adhesion and diapedesis. Exemplary agents targeting agranulocyte adhe-sion and diapedesis include, but are not limited to, C5AR, ERM, ICAM1, ICAM2, VCAM, Mac1, LFA1, Itg alpha 9, and Itg beta 1. Agents targeting agranulocyte adhesion and diapedesis are well known in the art.

Exemplary pathways include osteoarthritis pathway. Exemplary agents targeting osteoarthritis pathway include, but are not limited to, Wnt, beta catenin, MMP3, and Runx2. Agents targeting osteoarthritis pathway are well known in the art.

Exemplary pathways include the role of macrophages, fibroblasts and endothelial cells in rheumatoid arthritis. Exemplary agents targeting the role of macrophages, fibroblasts and endothelial cells in rheumatoid arthritis include, but are not limited to, MyD88, IRAK, PI3K, TRADD, TRAF2, IKK, IKB, JAK2, IKK, PKC, and NFKB. Agents targeting the role of macrophages, fibroblasts and endothelial cells in rheumatoid arthritis are well known in the art.

Exemplary pathways include hepatic fibrosis and hepatic stellate cell activation. Exemplary agents targeting hepatic fibrosis and hepatic stellate cell activation include, but are not limited to, ERK, p38, PDGF-BB, PDGFR, JNK, SREBP2, and miR-33a. Agents targeting hepatic fibrosis and hepatic stellate cell activation are well known in the art.

Exemplary pathways include inhibition of matrix metalloproteases. Exemplary agents targeting inhibition of matrix metalloproteases include, but are not limited to, TIMP1, TIMP2, TIMP3, TIMP4, TSP2, TSPI2, and a2-Macroglobulin. Agents targeting inhibition of matrix metalloproteases are well known in the art.

Exemplary pathways include atherosclerosis signaling. Exemplary agents targeting atherosclerosis signaling include, but are not limited to, HO-1 and MAPK. Agents targeting atherosclerosis signaling are well known in the art.

Exemplary pathways include bladder cancer signaling. Exemplary agents targeting bladder cancer signaling include, but are not limited to, HRAS, FGFR3, CDKN2A, and p53 RB. Agents targeting bladder cancer signaling are well known in the art.

Exemplary pathways include the role of pattern recognition receptors in recognition of bacteria and viruses. Exemplary agents targeting the role of pattern recognition receptors in recognition of bacteria and viruses include, but are not limited to, NOD1, NOD2, NFKB, ERK1/2, IRF7, and PKC. Agents targeting the role of pattern recognition receptors in recognition of bacteria and viruses are well known in the art.

Exemplary pathways include HMGB1 Signaling. Exemplary agents targeting HMGB1 Signaling include, but are not limited to, TLR-4, TLR-2, RAGE, NFkB, and MEK. Agents targeting HMGB1 Signaling are well known in the art.

Based on the teachings and disclosures provided herein, one with ordinary skill in the art would be able to make and use various combination therapies with different agents disclosed herein and others known in the art that target one or more of the disclosed pathways.

Biomarker Panel and Probes for Predicting a Response to an IBD Treatment and Methods of Use International Patent Application Publication No. WO 2010/044952 A2, the content of which is incorporated herein by references in its entirety, disclosed a predictive panel of 109 probe sets, which mapped to 81 unique genes. The set of 109 probe sets was significantly differentially expressed at baseline between responders and non-responders (fold change >2, P<0.05). The panel of 109 probe sets was able to classify patients as responders or non-responders prior to infliximab treatment.

The panel of 109 probe sets was able to predict week 8 response with >90% sensitivity and specificity. A gene signature comprising 13 unique genes (molecular prediction signature or MPS) predicted responders to TNF-antagonist therapy with mixed results, which highlighted the challenge of developing clinical biomarkers of response to therapy due to heterogeneous patient populations and variability in endoscopic scoring.

However, it is discovered in the present invention that, despite the low specificity of the MPS in predicting responders to TNF-antagonist therapy in some cohorts, the MPS demonstrates high negative predictive value (NPV) as reflected by a high proportion (78%-89%) of true negative predictions in three independent TNF-antagonist clinical studies. It is further demonstrated in the present invention the utility of the MPS to identify non-responders to TNF-antagonist therapy in an independent clinical study using TNF-antagonist in a different ethnic population (Japanese), and in a clinical study evaluating an anti-inflammatory intervention other than a TNF-antagonist, such as JAK inhibitor and anti-interleukin (IL) treatment. Notably, the predicted non-responder patients cannot be distinguished by clinical measures or inflammatory markers, but they have specific gene expression and microbiome signatures that assist in targeting this non-responder population.

The present invention relates generally to the prediction of a response or non-response to a treatment in a subject diagnosed with IBD, and provides methods, reagents, and kits useful for this purpose. Provided herein are biomarkers that are indicative of and/or predictive for a response or non-response to the IBD treatment. Provided herein are biomarkers that are indicative of and/or predictive for a response or non-response to combination IBD treatment. In certain embodiments, the present invention provides a panel of biomarkers (e.g., genes that are expressed or proteins in a subject at a specific time point) that indicate the subject will have either a positive response or a negative response to the IBD treatment. In certain embodiments, subjects with a negative response or non-responders are prime candidates for combination therapies.

Provided herein is a method of predicting a response of a subject diagnosed with an inflammatory bowel disease (IBD) to an anti-inflammatory treatment of the IBD. In one embodiment, the IBD is ulcerative colitis. In another embodiment, the IBD is Crohn's disease.

In one embodiment, the subject is any animal. In another embodiment, the subject is a mammal. In one embodiment, the subject is a human. In an embodiment, the subject is a human diagnosed with IBD. In another embodiment, the subject is a human diagnosed with ulcerative colitis. In an embodiment, the subject is a human diagnosed with Crohn's disease.

In certain embodiments, the response to an IBD treatment is predicted before the treatment is administered to the subject. In certain embodiments, the response to an IBD treatment is predicted after the treatment is administered to the subject.

In certain embodiments, the response to the treatment in the subject is a positive response. In one embodiment, the positive response is characterized by at least one of mucosal healing, a clinical response, or a clinical remission. In certain embodiments, the response is a negative response or non-response. In one embodiment, the negative response or non-response to the IBD treatment is characterized by not having at least one of mucosal healing, clinical response, and clinical remission.

In some embodiments, the method includes contacting a sample from the subject with a set of probes. In some embodiments, the sample includes any sampling of cells, tissues, or bodily fluids from the subject. In one embodiment, the sample is a tissue sample. In one embodiment, the sample is a biopsy. In one embodiment, the sample is a colon biopsy. In one embodiment, the sample is a smear. In one embodiment, the sample is blood. In one embodiment, the sample is lymph. In one embodiment, the sample is urine. In one embodiment, the sample is saliva. In one embodiment, the sample is stool. In one embodiment, the sample is obtained before the subject is treated with the anti-inflammatory treatment.

The probe can be any molecule or agent that specifically detects a biomarker. In certain embodiments, the probe is selected from the group consisting of an aptamer, an antibody, an affibody, a peptide, and a nucleic acid. In one embodiment, the probe is an aptamer. An aptamer is an oligonucleotide or a peptide that binds specifically to a target molecule. An aptamer is usually created by selection from a large random sequence pool. Examples of aptamers useful for the invention include oligonucleotides, such as DNA, RNA or nucleic acid analogues, or peptides, that bind to a biomarker of the invention. In one embodiment, the aptamers are single-stranded DNA-based protein affinity binding reagents. In another embodiment, the probe is an antibody. In one embodiment, the probe is an affibody. In another embodiment, the probe is a peptide. In one embodiment, the probe is a nucleic acid. In an embodiment, the nucleic acid probe is an oligonucleotide hybridizing to the gene or mRNA of a biomarker. In another embodiment, the nucleic acid probe is a cDNA synthesized from the mRNA of a biomarker. In an embodiment, the probe is selected from a group consisting of SEQ ID NOS. 1-14, SEQ ID NO. 17, SEQ ID NO. 20, SEQ ID NO. 23, SEQ ID NO. 26, SEQ ID NO. 29, SEQ ID NO. 32, SEQ ID NO. 35, SEQ ID NO. 38, SEQ ID NO. 41, SEQ ID NO. 44, SEQ ID NO. 47, and SEQ ID NO. 50.

In other embodiments, the sample is contacted with a set of probes capable of detecting a panel of biomarkers comprising 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In some embodiments, the sample is contacted with a set of probes capable of detecting a panel of biomarkers consisting of 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In some embodiments, the sample is contacted with a set of probes capable of detecting a panel of biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In other embodiments, the sample is contacted with a set of probes capable of detecting a panel of biomarkers comprising one biomarker selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3). In one embodiment, the biomarker is CMTM2. In one embodiment, the biomarker is C5AR1. In one embodiment, the biomarker is FGF2. In one embodiment, the biomarker is GK. In one embodiment, the biomarker is HGF. In one embodiment, the biomarker is IL1RN. In one embodiment, the biomarker is LILRA2. In one embodiment, the biomarker is NAMPT. In one embodiment, the biomarker is PAPPA. In one embodiment, the biomarker is SNCA. In one embodiment, the biomarker is SOD2. In one embodiment, the biomarker is STEAP4. In one embodiment, the biomarker is ZBED3.

In other embodiments, the sample is contacted with a set of probes capable of detecting a panel of biomarkers comprising two biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In other embodiments, the sample is contacted with a set of probes capable of detecting a panel of biomarkers comprising three biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In other embodiments, the sample is contacted with a set of probes capable of detecting a panel of biomarkers comprising four biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In other embodiments, the sample is contacted with a set of probes capable of detecting a panel of biomarkers comprising five biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In other embodiments, the sample is contacted with a set of probes capable of detecting a panel of biomarkers comprising six biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In other embodiments, the sample is contacted with a set of probes capable of detecting a panel of biomarkers comprising seven biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In other embodiments, the sample is contacted with a set of probes capable of detecting a panel of biomarkers comprising eight biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In other embodiments, the sample is contacted with a set of probes capable of detecting a panel of biomarkers comprising nine biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In other embodiments, the sample is contacted with a set of probes capable of detecting a panel of biomarkers comprising ten biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In other embodiments, the sample is contacted with a set of probes capable of detecting a panel of biomarkers comprising eleven biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

In other embodiments, the sample is contacted with a set of probes capable of detecting a panel of biomarkers comprising twelve biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3).

One embodiment includes a probe capable of detecting a biomarker comprising STEAP4 metalloreductase (STEAP4).

In a further embodiment, the set of probes is capable of detecting a panel of biomarkers comprising STEAP4 metalloreductase (STEAP4) and 1, 2, 3, 4, 5, 6, 7, 8, 9, 10, 11, or 12 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3). In one embodiment, the sample is contacted with a set of probes capable of detecting a panel of biomarkers comprising STEAP4 metalloreductase (STEAP4) and one biomarker selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3).

In some embodiments, the sample is contacted with a set of probes capable of detecting a panel of biomarkers comprising STEAP4 metalloreductase (STEAP4) and two biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3).

In some embodiments, the sample is contacted with a set of probes capable of detecting a panel of biomarkers comprising STEAP4 metalloreductase (STEAP4) and three biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3).

In some embodiments, the sample is contacted with a set of probes capable of detecting a panel of biomarkers comprising STEAP4 metalloreductase (STEAP4) and four biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3).

In some embodiments, the sample is contacted with a set of probes capable of detecting a panel of biomarkers comprising STEAP4 metalloreductase (STEAP4) and five biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3).

In some embodiments, the sample is contacted with a set of probes capable of detecting a panel of biomarkers comprising STEAP4 metalloreductase (STEAP4) and six biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3).

In some embodiments, the sample is contacted with a set of probes capable of detecting a panel of biomarkers comprising STEAP4 metalloreductase (STEAP4) and seven biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3).

In some embodiments, the sample is contacted with a set of probes capable of detecting a panel of biomarkers comprising STEAP4 metalloreductase (STEAP4) and eight biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3).

In some embodiments, the sample is contacted with a set of probes capable of detecting a panel of biomarkers comprising STEAP4 metalloreductase (STEAP4) and nine biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3).

In some embodiments, the sample is contacted with a set of probes capable of detecting a panel of biomarkers comprising STEAP4 metalloreductase (STEAP4) and ten biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3).

In some embodiments, the sample is contacted with a set of probes capable of detecting a panel of biomarkers comprising STEAP4 metalloreductase (STEAP4) and eleven biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3).

Given the teachings and guidance provided herein one skilled in the art will understand that the disclosure herein is intended to include a method of predicting a response of a subject diagnosed with an inflammatory bowel disease (IBD) to an anti-inflammatory treatment of the IBD, the method comprising:

a. contacting a sample from a subject with a probe or a set of probes disclosed above; and b. determining a pattern of the panel of biomarkers, wherein the pattern of the panel of the biomarkers predicts the response to the anti-antinflammatory treatment in the subject. The anti-inflammatory treatment can be, for example, anti-interleukin (anti-IL) or a JAK inhibitor treatment.

In another embodiment, provided herein is a method of predicting a response of a subject diagnosed with an inflammatory bowel disease (IBD) to an anti-inflammatory treatment of the IBD, the method comprising:

a. contacting a sample from a subject with a set of probes capable of detecting a panel of biomarkers comprising 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3); and b. determining a pattern of the panel of biomarkers;

wherein the pattern of the panel of biomarkers predicts the response to the anti-inflammatory treatment in the subject. The anti-inflammatory treatment can be, for example, anti-interleukin (anti-IL) or a JAK inhibitor treatment.

In other embodiment, provided herein is a method of predicting a response of a subject diagnosed with an inflammatory bowel disease (IBD) to an anti-interleukin treatment of the IBD, the method comprising:

a. contacting a sample from a subject with a set of probes capable of detecting a panel of biomarkers comprising 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3); and b. determining a pattern of the panel of biomarkers;

wherein the pattern of the panel of biomarkers predicts the response to the anti-IL treatment in the subject.

Provided herein is a method of predicting a response of a subject diagnosed with an inflammatory bowel disease (IBD) to an JAK inhibitor treatment of the IBD, the method comprising:

a. contacting a sample from a subject with a set of probes capable of detecting a panel of biomarkers comprising 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3); and b. determining a pattern of the panel of biomarkers;

wherein the pattern of the panel of biomarkers predicts the response to the JAK inhibitor treatment in the subject.

Provided herein is a method of predicting a response of a subject diagnosed with an inflammatory bowel disease (IBD) to an anti-inflammatory treatment of the IBD, the method comprising:

a. contacting a sample from a subject with a probe capable of detecting a biomarker comprising STEAP4 metalloreductase (STEAP4); and b. determining a pattern of the panel of biomarker, wherein the pattern of the panel of the biomarker predicts the response to the anti-antinflammatory treatment in the subject. The anti-inflammatory treatment can be, for example, anti-interleukin (anti-IL) or a JAK inhibitor treatment.

Provided herein is a method of predicting a response of a subject diagnosed with an inflammatory bowel disease (IBD) to an anti-inflammatory treatment of the IBD, the method comprising:

a. contacting a sample from a subject with a set of probes capable of detecting a panel of biomarkers comprising STEAP4 metalloreductase (STEAP4) and 1, 2, 3, 4, 5, 6, 7, 8, 9, 10, 11, or 12 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3); and b. determining a pattern of the panel of biomarkers;

wherein the pattern of the panel of biomarkers predicts the response to the anti-inflammatory treatment in the subject. The anti-inflammatory treatment can be, for example, anti-interleukin (anti-IL) or a JAK inhibitor treatment.

Provided herein is a method of predicting a response of a subject diagnosed with an inflammatory bowel disease (IBD) to an anti-interleukin treatment of the IBD, the method comprising:

a. contacting a sample from a subject with a set of probes capable of detecting a panel of biomarkers comprising STEAP4 metalloreductase (STEAP4) and 1, 2, 3, 4, 5, 6, 7, 8, 9, 10, 11, or 12 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3); and b. determining a pattern of the panel of biomarkers;

wherein the pattern of the panel of biomarkers predicts the response to the anti-IL treatment in the subject.

Provided herein is a method of predicting a response of a subject diagnosed with an inflammatory bowel disease (IBD) to an JAK inhibitor treatment of the IBD, the method comprising:

a. contacting a sample from a subject with a set of probes capable of detecting a panel of biomarkers comprising STEAP4 metalloreductase (STEAP4) and 1, 2, 3, 4, 5, 6, 7, 8, 9, 10, 11, or 12 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3); and b. determining a pattern of the panel of biomarkers;

wherein the pattern of the panel of biomarkers predicts the response to the JAK inhibitor treatment in the subject.

The pattern of the panel of biomarkers as provided herein is determined by: (a) determining the baseline gene expression levels of the panel of biomarkers in the subject, and (b) determining the signature score for each sample.

Any methods available in the art for detecting expression of biomarkers are encompassed herein. The expression, presence or amount of a biomarker of the invention can be detected on a nucleic acid level (e.g., as an RNA transcript) or a protein level. By "detecting or determining expression of a biomarker" is intended to include determining the quantity or presence of a protein or its RNA transcript for the biomarkers disclosed herein. Thus, "detecting expression" encompasses instances where a biomarker is determined not to be expressed, not to be detectably expressed, expressed at a low level, expressed at a normal level, or overexpressed.

In certain embodiments, provided herein are DNA-, RNA-, and protein-based diagnostic methods that either directly or indirectly detect the biomarkers described herein. The present invention also provides compositions, reagents, and kits for such diagnostic purposes. The diagnostic methods described herein may be qualitative or quantitative. Quantitative diagnostic methods may be used, for example, to compare a detected biomarker level to a cutoff or threshold level. Where applicable, qualitative or quantitative diagnostic methods can also include amplification of a target, a signal, or an intermediary.

In certain embodiments, biomarkers are detected at the nucleic acid (e.g., RNA) level. For example, the amount of biomarker RNA (e.g., mRNA) present in a sample is determined (e.g., to determine the level of biomarker expression). Biomarker nucleic acid (e.g., RNA, amplified cDNA, etc.) can be detected/quantified using a variety of nucleic acid techniques known to those of ordinary skill in the art, including but not limited to, quantitative polymerase chain reaction (qPCR), nucleic acid hybridization, and nucleic acid amplification. In one embodiment, the PCR primers, including qPCR primers, are selected from the group consisting of SEQ ID NO. 15, SEQ ID NO. 16, SEQ ID NO. 18, SEQ ID NO. 19, SEQ ID NO. 21, SEQ ID NO. 22, SEQ ID NO. 24, SEQ ID NO. 25, SEQ ID NO. 27, SEQ ID NO. 28, SEQ ID NO. 30, SEQ ID NO. 31, SEQ ID NO. 33, SEQ ID NO. 34, SEQ ID NO. 36, SEQ ID NO. 37, SEQ ID NO. 39, SEQ ID NO. 40, SEQ ID NO. 42, SEQ ID NO. 43, SEQ ID NO. 45, SEQ ID NO. 46, SEQ ID NO. 48, SEQ ID NO. 49, SEQ ID NO. 51, and SEQ ID NO. 52.

In certain embodiments, a microarray is used to detect the biomarker. Microarrays can, for example, include DNA microarrays; protein microarrays; tissue microarrays; cell microarrays; chemical compound microarrays; and antibody microarrays. A DNA microarray, commonly referred to as a gene chip can be used to monitor expression levels of thousands of genes simultaneously. Microarrays can be used to identify disease genes by comparing expression in disease states versus normal states. Microarrays can also be used for diagnostic purposes, i.e., patterns of expression levels of genes can be studied in samples prior to the diagnosis of disease, and these patterns can later be used to predict the occurrence of a disease state in a healthy subject. Microarrays can also be used to predict the response of a subject to a given therapeutic treatment by detecting patters of expression levels of genes prior to/or concurrent with diagnosis of a disease state in the subject.

In certain embodiments, the expression products are proteins corresponding to the biomarkers of the panel. In certain embodiments, detecting the levels of expression products comprises exposing the sample to antibodies for the proteins corresponding to the biomarkers of the panel. In certain embodiments, the antibodies are covalently linked to a solid surface. In certain embodiments, detecting the levels of expression products comprises exposing the sample to a mass analysis technique (e.g., mass spectrometry).

In certain embodiments, reagents are provided for the detection and/or quantification of biomarker proteins. The reagents can include, but are not limited to, primary antibodies that bind the protein biomarkers, secondary antibodies that bind the primary antibodies, affibodies that bind the protein biomarkers, aptamers that bind the protein or nucleic acid biomarkers (e.g., RNA or DNA), and/or nucleic acids that bind the nucleic acid biomarkers (e.g., RNA or DNA). The detection reagents can be labeled (e.g., fluorescently) or unlabeled. Additionally, the detection reagents can be free in solution or immobilized.

In certain embodiments, when quantifying the level of a biomarker(s) present in a sample, the level can be determined on an absolute basis or a relative basis. When determined on a relative basis, comparisons can be made to controls, which can include, but are not limited to historical samples from the same patient (e.g., a series of samples over a certain time period), level(s) found in a subject or population of subjects without the disease or disorder (e.g., IBD), a threshold value, and an acceptable range.

In some embodiments, 1 to 13 biomarkers are used to predict a patient's response. Any range therein is also contemplated. In one embodiment, 1 biomarker is used to predict a patient's response. In one embodiment, 2 biomarkers are used to predict a patient's response. In one embodiment, 3 biomarkers are used to predict a patient's response. In one embodiment, 4 biomarkers are used to predict a patient's response. In one embodiment, 5 biomarkers are used to predict a patient's response. In another embodiment, 6 biomarkers are used to predict a patient's response. In another embodiment, 7 biomarkers are used to predict a patient's response. In yet another embodiment, 8 biomarkers are used to predict a patient's response. In yet another embodiment, 9 biomarkers are used to predict a patient's response. In yet another embodiment, 11 biomarkers are used to predict a patient's response. In yet another embodiment, 12 biomarkers are used to predict a patient's response. In another embodiment, 13 biomarkers are used to predict a patient's response.

In some embodiments, the one or more biomarkers are independently selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3). In one embodiment, the biomarker is CMTM2. In one embodiment, the biomarker is C5AR1. In one embodiment, the biomarker is FGF2. In one embodiment, the biomarker is GK. In one embodiment, the biomarker is HGF. In one embodiment, the biomarker is IL1RN. In one embodiment, the biomarker is LILRA2. In one embodiment, the biomarker is NAMPT. In one embodiment, the biomarker is PAPPA. In one embodiment, the biomarker is SNCA. In one embodiment, the biomarker is SOD2. In one embodiment, the biomarker is STEAP4. In one embodiment, the biomarker is ZBED3.

In one embodiment, the pattern of the panel of biomarkers is determined using a method comprising determining the baseline gene expression level of each of the biomarkers in the panel. In one embodiment, the pattern of the panel of biomarkers is determined using a method comprising utilizing the baseline gene expression level of each of the biomarkers to determine the signature score for each sample. As used herein, "signature score" is a unique risk score individually calculated for each sample based on the gene expression levels of the panel of biomarkers. Exemplary method of determining the signature score is illustrated in Example 8. In some embodiments, the signature score can be determined by other techniques known in the art.

In certain embodiments, the subject is predicted to be a responder to the anti-inflammatory treatment of the IBD if the signature score of the panel of biomarkers is above a pre-specified threshold indicative of response. In one embodiment, the subject is predicted to be a responder to the anti-IL treatment of the IBD if the signature score of the panel of biomarkers is above a pre-specified threshold indicative of response. In another embodiment, the subject is predicted to be a responder to the JAKi treatment of the IBD if the signature score of the panel of biomarkers is above a pre-specified threshold indicative of response. In certain embodiments, the subject is predicted to be a non-responder to the anti-inflammatory treatment of the IBD if the signature score of the panel of biomarkers is below a pre-specified threshold indicative of non-response. In one embodiment, the subject is predicted to be a non-responder to the anti-IL treatment of the IBD if the signature score of the panel of biomarkers is below a pre-specified threshold indicative of non-response. In another embodiment, the subject is predicted to be a non-responder to the JAKi treatment of the IBD if the signature score of the panel of biomarkers is below a pre-specified threshold indicative of response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising one biomarker selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising two biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising three biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising four biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising five biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising six biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising seven biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising eight biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample; and c. determining the signature score for each sample; wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising nine biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample; and c. determining the signature score for each sample; wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising ten biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample; and c. determining the signature score for each sample; wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising eleven biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample; and c. determining the signature score for each sample; wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising twelve biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample; and c. determining the signature score for each sample; wherein the subject is predicted to be a non-responder to the anti-inflammatory treatment of the IBD if the signature score of the panel of biomarkers is below a pre-specified threshold indicative of non-response.

In one embodiment, provided herein is a method of predicting a negative response of a subject diagnosed with an inflammatory bowel disease (IBD) to an anti-inflammatory treatment of the IBD, the method comprising:

a. contacting a sample from a subject with a of probe capable of detecting a biomarker comprising STEAP4 metalloreductase (STEAP4);

b. determining baseline gene expression levels of the panel of biomarkers in the sample; and c. determining the signature score for each sample;

wherein the subject is predicted to be a non-responder to the anti-inflammatory treatment of the IBD if the signature score of the biomarker is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising STEAP4 metalloreductase (STEAP4) and 1, 2, 3, 4, 5, 6, 7, 8, 9, 10, 11, or 12 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising STEAP4 metalloreductase (STEAP4) and one biomarker selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In one embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising STEAP4 metalloreductase (STEAP4) and two biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising STEAP4 metalloreductase (STEAP4) and three biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In one embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising STEAP4 metalloreductase (STEAP4) and four biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In one embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising STEAP4 metalloreductase (STEAP4) and five biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In other embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising STEAP4 metalloreductase (STEAP4) and six biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In one embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising STEAP4 metalloreductase (STEAP4) and seven biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In another embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising STEAP4 metalloreductase (STEAP4) and eight biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In one embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising STEAP4 metalloreductase (STEAP4) and nine biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In certain embodiment, provided herein is a method of predicting a negative response of a subject diagnosed with an inflammatory bowel disease (IBD) to an anti-inflammatory treatment of the IBD, the method comprising:

a. contacting a sample from a subject with a set of probes capable of detecting a panel of biomarkers comprising STEAP4 metalloreductase (STEAP4) and ten biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobu-lin like receptor A2 (LILRA2), nicotinamide phospho-ribosyltransferase (NAMPT), pappalysin 1 (PAPPA), synuclein alpha (SNCA), superoxide dismutase 2, mitochondrial (SOD2), and zinc finger BED-type con-taining 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In one embodiment, provided herein is a method of predicting a negative response of a subject diagnosed with an inflammatory bowel disease (IBD) to an anti-inflamma-tory treatment of the IBD, the method comprising:

a. contacting a sample from a subject with a set of probes capable of detecting a panel of biomarkers comprising STEAP4 metalloreductase (STEAP4) and eleven bio-markers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobu-lin like receptor A2 (LILRA2), nicotinamide phospho-ribosyltransferase (NAMPT), pappalysin 1 (PAPPA), synuclein alpha (SNCA), superoxide dismutase 2, mitochondrial (SOD2), and zinc finger BED-type con-taining 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In one embodiment, provided herein is a method of predicting a negative response of a subject diagnosed with an inflammatory bowel disease (IBD) to an anti-inflamma-tory treatment of the IBD, the method comprising:

a. contacting a sample from a subject with a set of probes capable of detecting a panel of biomarkers comprising STEAP4 metalloreductase (STEAP4) and all biomark-ers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobu-lin like receptor A2 (LILRA2), nicotinamide phospho-ribosyltransferase (NAMPT), pappalysin 1 (PAPPA), synuclein alpha (SNCA), superoxide dismutase 2, mitochondrial (SOD2), and zinc finger BED-type con-taining 3 (ZBED3);

b. determining baseline gene expression levels of the panel of biomarkers in the sample; and c. determining the signature score for each sample;

wherein the subject is predicted to be a non-responder to the anti-inflammatory treatment of the IBD if the signature score of the panel of biomarkers is below a pre-specified threshold indicative of non-response.

In one embodiment, provided herein is a method of predicting a negative response of a subject diagnosed with an inflammatory bowel disease (IBD) to an anti-inflamma-tory treatment of the IBD, the method comprising:

a. contacting a sample from a subject with a set of probes capable of detecting a panel of biomarkers consisting of CKLF-like MARVEL transmembrane domain contain-ing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobu-lin like receptor A2 (LILRA2), nicotinamide phospho-ribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b. determining baseline gene expression levels of the panel of biomarkers in the sample by quantitative polymerase chain reaction (qPCR); and c. determining the signature score for each sample;

wherein the subject is predicted to be a non-responder to the anti-inflammatory treatment of the IBD if the signature score of the panel of biomarkers is below a pre-specified threshold indicative of non-response.

In some embodiments, the pre-specified threshold level is selected from the group consisting of between −3.9000 and 1.1000. All ranges between −3.9000 and 1.1000 are con-templated. In other embodiments, the pre-specified thresh-old level is selected from the group consisting of between −3.8500 and 1.0500. In certain embodiments, the pre-speci-fied threshold level is selected from the group consisting of between −3.8250 and 1.0250. In another embodiments, the pre-specified threshold level is selected from the group consisting of between −3.8234 and 1.0000. In another embodiment, the pre-specified threshold level is selected from the group consisting of between −3.8000 and 0.9000. In other embodiments, the pre-specified threshold level is selected from the group consisting of between −3.5000 and 0.6000. In other embodiments, the pre-specified threshold level is selected from the group consisting of between −3.0000 and 0.2000. In another embodiments, the pre-specified threshold level is selected from the group consist-ing of between −2.5000 and 1.0000. In other embodiments, the pre-specified threshold level is selected from the group consisting of between −2.5000 and 0.6000. In other embodi-ments, the pre-specified threshold level is selected from the group consisting of between −2.5000 and 0.2000. In another embodiments, the pre-specified threshold level is selected from the group consisting of between −1.5000 and 1.0000. In other embodiments, the pre-specified threshold level is selected from the group consisting of between −1.5000 and 0.6000. In other embodiments, the pre-specified threshold level is selected from the group consisting of between −1.5000 and 0.2000. In one embodiment, the pre-specified threshold level is −3.8234. In another embodiment, the pre-specified threshold level is 1.0000.

In certain embodiments, the threshold level of a signature score can be determined to represent the maximum sum of sensitivity and specificity. In other embodiments, the thresh-old level of a signature score can be determined to represent the maximum positive predictive value. In other embodi-ments, the threshold level of a signature score can be determined to represent the maximum negative predictive value.

In certain embodiments, the non-responder subjects have one or more of the characteristics selected from the group consisting of high disease burden, microbial dysbiosis, and high levels of inflammatory activity. In one embodiment, the non-responder subjects have high disease burden. In another embodiment, the non-responder subjects have microbial dysbiosis. In one embodiment, the non-responder subjects have microbial dysbiosis of the gastrointestinal tract. In another embodiment, the non-responder subjects have microbial dysbiosis of the small intestine. In another embodiment, the non-responder subjects have microbial dysbiosis of the large intestine. In other embodiments, the non-responder subjects have high levels of inflammatory activity.

In certain embodiments, provided are methods of determining a treatment regimen for a subject diagnosed with inflammatory bowel disease (IBD). The methods comprise: (a) contacting a sample obtained from the subject with an isolated set of probes of the invention to detect a panel of biomarkers of the invention in the sample; and (b) detecting a pattern of the panel of biomarkers that determines the appropriate treatment regimen for the subject. By way of an example, when detecting a pattern of the panel of biomarkers, upon determining a first pattern with increased or decreased baseline gene expression levels of certain biomarker genes relative to the baseline gene expression level in control, such as a healthy subject, or a pre-specified threshold indicative of positive response or non-response to a treatment, one skilled in the art would understand that a specific treatment regimen could be used to successfully treat IBD. Upon determining a second pattern with increased or decreased expression of a different set of biomarkers, one skilled in the art would understand that a different treatment regimen could be used to successfully treat IBD.

In certain embodiments, provided are methods of monitoring the responsiveness to a treatment regimen in a subject being treated for inflammatory bowel disease (IBD). The methods comprise (a) obtaining a first sample from the subject being treated for IBD; (b) obtaining a second sample from the subject being treated for IBD; (c) contacting the samples with an isolated set of probes of the invention to detect the panel of biomarkers in the samples; and (c) detecting a difference in the pattern of the panel of biomarkers between the two samples, wherein the difference in the pattern of the panel of biomarkers between the two samples indicates the responsiveness to the treatment regimen in the subject. By way of an example, a subject being treated for IBD will express a certain pattern of a panel of biomarkers of the invention at the start of the treatment regimen. During the course of treatment, a sample or multiple samples can be obtained from the subject, and these samples can be used to determine a difference in the pattern of the panel of biomarkers. In one embodiment, the pattern of the panel of biomarkers comprises gene expression levels of the biomarkers within the panel. Increased expression or decreased expression of the panel of biomarkers can indicate that the treatment regimen is successfully treating the IBD. The expression level of a second set of biomarkers can also be used to indicate whether the treatment regimen is successful to treat the IBD.

In certain embodiments, when determining a treatment regimen or monitoring the response to a treatment regimen, multiple samples can be obtained from the subject and the pattern of biomarkers can be determined for each sample that is obtained from the subject. Monitoring the pattern of biomarkers over time and in response to the treatment regimen can provide one skilled in the art the information necessary to determine a treatment regimen, to maintain the same treatment regimen, or to change the treatment regimen.

In some embodiments, provided herein is a method of predicting a response of a subject diagnosed with an inflammatory bowel disease (IBD) to an anti-inflammatory treatment of the IBD, the method further comprising administering to the subject one or more of the anti-inflammatory treatment of the IBD. In further embodiments, the anti-inflammatory treatment provided herein includes, but is not limited to, aminosalicylates, corticosteroids, anti-tumor necrosis factor (TNF) agents, anti-integrin agents, JAK inhibitors, and anti-interleukin agents. In one embodiment, the anti-inflammatory treatment is one or more aminosalicylate. In one embodiment, the aminosalicylate is sulfasalazine. In one embodiment, the aminosalicylate is mesalamine. In one embodiment, the aminosalicylate is olsalazine. In one embodiment, the aminosalicylate is balsalazide. In one embodiment, the anti-inflammatory treatment is one or more corticosteroid. In one embodiment, the corticosteroid is prednisone. In one embodiment, the corticosteroid is prednisolone. In one embodiment, the corticosteroid is methylprednisolone. In one embodiment, the anti-inflammatory treatment is budesonide. In one embodiment, the anti-inflammatory treatment is one or more anti-tumor necrosis factor (TNF) agent. In one embodiment, the anti-TNF agent is infliximab (Remicade). In one embodiment, the anti-TNF agent is adalimumab (Humira). In one embodiment, the anti-TNF agent is golimumab (Simponi). In one embodiment, the anti-inflammatory treatment is one or more anti-integrin agent. In one embodiment, the anti-integrin agent is vedolizumab. In one embodiment, the anti-integrin agent is natalizumab. In one embodiment, the anti-inflammatory treatment is one or more JAK inhibitors. In some embodiments, the JAK inhibitors are inhibitors against one or more of four JAK members: JAK1, JAK2, JAK3, and TYK2. In one embodiment, the JAK inhibitor is filgotinib. In one embodiment, the JAK inhibitor is peficitinib. In one embodiment, the JAK inhibitor is tofacitinib (Xeljanz/Jakvinus). In one embodiment, the JAK inhibitor is upadacitinib. In one embodiment, the anti-inflammatory treatment is one or more anti-interleukin agent. In some embodiments, the anti-interleukin (IL) agents include but are not limited to one or more of anti-IL-1 agents, anti-IL-6 agents, anti-IL-10 agents, anti-IL-13 agents, anti-IL-17 agents, anti-IL-12/23 agents, or anti-IL-23 agents. In one embodiment, the anti-IL agent is BI 655066. In one embodiment, the anti-IL agent is briakinumab. In one embodiment, the anti-IL agent is guselkumab. In one embodiment, the anti-IL agent is tildrakizumab. In one embodiment, the anti-IL agent is ustekinumab (Stelara).

In some embodiments, the non-responder subjects are identified as candidates for combination therapy. In certain embodiments, the combination therapy comprises two or more therapies selected from the group consisting of anti-inflammatory treatment, antibiotics, immunomodulators, anti-diarrheal medications, pain relievers, iron supplements, and calcium and vitamin D supplements. In certain embodiments, the combination therapy includes administering to the subject an inhibitor of NKG2D.

In certain embodiments, the combination therapy comprises using two or more anti-inflammatory drugs. Exemplary combination therapies with two anti-inflammatory drugs include, but are not limited to, administration of aminosalicylates and corticosteroids to the same patient, administration of aminosalicylates and anti-TNF agents to the same patient, administration of aminosalicylates and JAK inhibitors to the same patient, administration of aminosalicylates and anti-interleukin agents to the same patient, corticosteroids and anti-TNF agents to the same patient, administration of corticosteroids and JAK inhibitors to the same patient, administration of corticosteroids and anti-interleukin agents to the same patient, administration of anti-TNF agents and JAK inhibitors to the same patient, administration of anti-TNF agents and anti-interleukin agents to the same patient, administration of JAK inhibitors and anti-interleukin agents to the same patient, administration of anti-integrin agents and aminosalicylates to the same patient, administration of anti-integrin agents and corticosteroids to the same patient, administration of anti-integrin agents and anti-TNF agents to the same patient, administration of anti-integrin agents and JAK inhibitors to the same patient, and administration of anti-integrin agents and anti-interleukin agents to the same patient.

In other embodiments, the combination therapy comprises using one or more anti-inflammatory drug in combination with one or more antibiotic. Exemplary combination therapies with one anti-inflammatory drug in combination with antibiotics include, but are not limited to, administration of aminosalicylates and metronidazole to the same patient, administration of corticosteroids and metronidazole to the same patient, administration of anti-TNF agents and metronidazole to the same patient, administration of anti-integrin agents and metronidazole to the same patient, administration of JAK inhibitors and metronidazole to the same patient, administration of anti-interleukin agents and metronidazole to the same patient, administration of aminosalicylates and ciprofloxacin to the same patient, administration of corticosteroids and ciprofloxacin to the same patient, administration of anti-TNF agents and ciprofloxacin to the same patient, administration of anti-integrin agents and ciprofloxacin to the same patient, administration of JAK inhibitors and ciprofloxacin to the same patient, and administration of anti-interleukin agents and ciprofloxacin to the same patient.

In some embodiments, the combination therapy comprises using one or more anti-inflammatory drug in combination with one or more immunomodulators. Exemplary combination therapies with one anti-inflammatory drug in combination with immunomodulatory include, but are not limited to, administration of aminosalicylates and azathioprine (AZA) to the same patient, administration of corticosteroids and AZA to the same patient, administration of anti-TNF agents and AZA to the same patient, administration of anti-integrin agents and AZA to the same patient, administration of JAK inhibitors and AZA to the same patient, administration of anti-interleukin agents and AZA to the same patient, administration of aminosalicylates and cyclosporine to the same patient, administration of corticosteroids and cyclosporine to the same patient, administration of anti-TNF agents and cyclosporine to the same patient, administration of anti-integrin agents and cyclosporine to the same patient, administration of JAK inhibitors and cyclosporine to the same patient, administration of anti-interleukin agents and cyclosporine to the same patient, administration of aminosalicylates and 6-mercaptopurine (6 MP) to the same patient, administration of corticosteroids and 6 MP to the same patient, administration of anti-TNF agents and 6 MP to the same patient, administration of anti-integrin agents and 6 MP to the same patient, administration of JAK inhibitors and 6 MP to the same patient, administration of anti-interleukin agents and 6 MP to the same patient, administration of aminosalicylates and methotrexate to the same patient, administration of corticosteroids and methotrexate to the same patient, administration of anti-TNF agents and methotrexate to the same patient, administration of anti-integrin agents and methotrexate to the same patient, administration of JAK inhibitors and methotrexate to the same patient, and administration of anti-interleukin agents and methotrexate to the same patient.

In some embodiments, the combination therapy comprises using one or more immunomodulators in combination with one or more antibiotic. Exemplary combination therapies with one immunomodulator in combination with one antibiotic include, but are not limited to, administration of AZA and metronidazole to the same patient, administration of cyclosporine and metronidazole to the same patient, administration of 6 MP and metronidazole to the same patient, administration of methotrexate and metronidazole to the same patient, administration of AZA and ciprofloxacin to the same patient, administration of cyclosporine and ciprofloxacin to the same patient, administration of 6 MP and ciprofloxacin to the same patient, administration of JAK inhibitors and ciprofloxacin to the same patient, and administration of methotrexate and ciprofloxacin to the same patient.

In some embodiments, the combination therapy comprises using one or more immunomodulators in combination with one or more antibiotics and one or more anti-inflammatory drugs. Exemplary combinations as such include, but are not limited to, administration of anti-TNF agent, ciprofloxacin and AZA to the same patient, administration of anti-IL agent, metronidazole and 6 MP to the same patient, administration of JAKi, ciprofloxacin and cyclosporine to the same patient, administration of aminosalicylates, metronidazole and methotrexate to the same patient, and administration of corticosteroids, ciprofloxacin and AZA to the same patient.

In some embodiments, the combination therapy comprises using two or more antibiotics. In other embodiments, the combination therapy comprises using two or more immunomodulators.

In other embodiments, the combination therapy comprises using one or more anti-inflammatory drug in combination with one or more anti-diarrheal medications. In some embodiments, the combination therapy comprises using one or more anti-inflammatory drug in combination with one or more pain relievers. In other embodiments, the combination therapy comprises using one or more anti-inflammatory drug in combination with one or more iron supplements. In some embodiments, the combination therapy comprises using one or more anti-inflammatory drug in combination with one or more calcium and vitamin D supplements.

In other embodiments, the combination therapy comprises using one or more antibiotics in combination with one or more anti-diarrheal medications. In some embodiments, the combination therapy comprises using one or more antibiotics in combination with one or more pain relievers. In other embodiments, the combination therapy comprises using one or more antibiotics in combination with one or more iron supplements. In some embodiments, the combination therapy comprises using one or more antibiotics in combination with one or more calcium and vitamin D supplements.

In other embodiments, the combination therapy comprises using one or more immunomodulators in combination with one or more anti-diarrheal medications. In some embodiments, the combination therapy comprises using one or immunomodulators in combination with one or more pain relievers. In other embodiments, the combination therapy comprises using one or more immunomodulators in combination with one or more iron supplements. In some embodiments, the combination therapy comprises using one or more immunomodulators in combination with one or more calcium and vitamin D supplements.

In some embodiments, the combination therapy comprises using one or more anti-diarrheal medications in combination with one or more pain relievers. In other embodiments, the combination therapy comprises using one or more anti-diarrheal medications in combination with one or more iron supplements. In some embodiments, the combination therapy comprises using one or more anti-diarrheal medications in combination with one or more calcium and vitamin D supplements. In other embodiments, the combination therapy comprises using one or more pain relievers in combination with one or more iron supplements. In some embodiments, the combination therapy comprises using one or more pain relievers in combination with one or more calcium and vitamin D supplements. In some embodiments, the combination therapy comprises using one or more iron supplements in combination with one or more calcium and vitamin D supplements.

In other embodiments, the combination therapy comprises administering to the subject one or more agents targeting one or more canonical pathways selected from the group consisting of granulocyte adhesion and diapedesis, agranulocyte adhesion and diapedesis, osteoarthritis pathway, role of macrophages, fibroblasts and endothelial cells in rheumatoid arthritis, hepatic fibrosis and hepatic stellate cell activation, inhibition of matrix metalloproteases, atherosclerosis signaling, bladder cancer signaling, role of pattern recognition receptors in recognition of bacteria and viruses, and HMGB1 signaling.

In some embodiments, the combination therapy comprises using one or more anti-inflammatory drugs in combination with one or more agents targeting one or more canonical pathways selected from the group consisting of granulocyte adhesion and diapedesis, agranulocyte adhesion and diapedesis, osteoarthritis pathway, role of macrophages, fibroblasts and endothelial cells in rheumatoid arthritis, hepatic fibrosis and hepatic stellate cell activation, inhibition of matrix metalloproteases, atherosclerosis signaling, bladder cancer signaling, role of pattern recognition receptors in recognition of bacteria and viruses, and HMGB1 signaling.

In other embodiments, the combination therapy comprises using one or more anti-inflammatory drugs in combination with one or more agents targeting granulocyte adhesion and diapedesis. In certain embodiments, the combination therapy comprises using one or more anti-inflammatory drugs in combination with one or more agents targeting agranulocyte adhesion and diapedesis. In other embodiments, the combination therapy comprises using one or more anti-inflammatory drugs in combination with one or more agents targeting osteoarthritis pathway. In some embodiments, the combination therapy comprises using one or more anti-inflammatory drugs in combination with one or more agents targeting role of macrophages, fibroblasts and endothelial cells in rheumatoid arthritis. In other embodiments, the combination therapy comprises using one or more anti-inflammatory drugs in combination with one or more agents targeting hepatic fibrosis and hepatic stellate cell activation. In other embodiments, the combination therapy comprises using one or more anti-inflammatory drugs in combination with one or more agents targeting inhibition of matrix metalloproteases. In some embodiments, the combination therapy comprises using one or more anti-inflammatory drugs in combination with one or more agents targeting atherosclerosis signaling. In other embodiments, the combination therapy comprises using one or more anti-inflammatory drugs in combination with one or more agents targeting bladder cancer signaling. In certain embodiments, the combination therapy comprises using one or more anti-inflammatory drugs in combination with one or more agents targeting role of pattern recognition receptors in recognition of bacteria and viruses. In other embodiments, the combination therapy comprises using one or more anti-inflammatory drugs in combination with one or more agents targeting HMGB1 signaling.

In other embodiments, the combination therapy comprises using one or more anti-TNF drugs in combination with one or more agents targeting granulocyte adhesion and diapedesis. In certain embodiments, the combination therapy comprises using one or more anti-TNF drugs in combination with one or more agents targeting agranulocyte adhesion and diapedesis. In other embodiments, the combination therapy comprises using one or more anti-TNF drugs in combination with one or more agents targeting osteoarthritis pathway. In some embodiments, the combination therapy comprises using one or more anti-TNF drugs in combination with one or more agents targeting role of macrophages, fibroblasts and endothelial cells in rheumatoid arthritis. In other embodiments, the combination therapy comprises using one or more anti-TNF drugs in combination with one or more agents targeting hepatic fibrosis and hepatic stellate cell activation. In other embodiments, the combination therapy comprises using one or more anti-TNF drugs in combination with one or more agents targeting inhibition of matrix metalloproteases. In some embodiments, the combination therapy comprises using one or more anti-TNF drugs in combination with one or more agents targeting atherosclerosis signaling. In other embodiments, the combination therapy comprises using one or more anti-TNF drugs in combination with one or more agents targeting bladder cancer signaling. In certain embodiments, the combination therapy comprises using one or more anti-TNF drugs in combination with one or more agents targeting role of pattern recognition receptors in recognition of bacteria and viruses. In other embodiments, the combination therapy comprises using one or more anti-TNF drugs in combination with one or more agents targeting HMGB1 signaling.

In other embodiments, the combination therapy comprises using golimumab in combination with one or more agents targeting granulocyte adhesion and diapedesis. In certain embodiments, the combination therapy comprises using golimumab in combination with one or more agents targeting agranulocyte adhesion and diapedesis. In other embodiments, the combination therapy comprises using golimumab in combination with one or more agents targeting osteoarthritis pathway. In some embodiments, the combination therapy comprises using golimumab in combination with one or more agents targeting role of macrophages, fibroblasts and endothelial cells in rheumatoid arthritis. In other embodiments, the combination therapy comprises using golimumab in combination with one or more agents targeting hepatic fibrosis and hepatic stellate cell activation. In other embodiments, the combination therapy comprises using golimumab in combination with one or more agents targeting inhibition of matrix metalloproteases. In some embodiments, the combination therapy comprises using golimumab in combination with one or more agents targeting atherosclerosis signaling. In other embodiments, the combination therapy comprises using golimumab in combination with one or more agents targeting bladder cancer signaling. In certain embodiments, the combination therapy comprises using golimumab in combination with one or more agents targeting role of pattern recognition receptors in recognition of bacteria and viruses. In other embodiments, the combination therapy comprises using golimumab in combination with one or more agents targeting HMGB1 signaling.

In other embodiments, the combination therapy comprises using one or more anti-IL drugs in combination with one or more agents targeting granulocyte adhesion and diapedesis. In certain embodiments, the combination therapy comprises using one or more anti-IL drugs in combination with one or more agents targeting agranulocyte adhesion and diapedesis. In other embodiments, the combination therapy comprises using one or more anti-IL drugs in combination with one or more agents targeting osteoarthritis pathway. In some embodiments, the combination therapy comprises using one or more anti-IL drugs in combination with one or more agents targeting role of macrophages, fibroblasts and endothelial cells in rheumatoid arthritis. In other embodiments, the combination therapy comprises using one or more anti-IL drugs in combination with one or more agents targeting hepatic fibrosis and hepatic stellate cell activation. In other embodiments, the combination therapy comprises using one or more anti-IL drugs in combination with one or more agents targeting inhibition of matrix metalloproteases. In some embodiments, the combination therapy comprises using one or more anti-IL drugs in combination with one or more agents targeting atherosclerosis signaling. In other embodiments, the combination therapy comprises using one or more anti-IL drugs in combination with one or more agents targeting bladder cancer signaling. In certain embodiments, the combination therapy comprises using one or more anti-IL drugs in combination with one or more agents targeting role of pattern recognition receptors in recognition of bacteria and viruses. In other embodiments, the combination therapy comprises using one or more anti-IL drugs in combination with one or more agents targeting HMGB1 signaling.

In other embodiments, the combination therapy comprises using ustekinumab in combination with one or more agents targeting granulocyte adhesion and diapedesis. In certain embodiments, the combination therapy comprises using ustekinumab in combination with one or more agents targeting agranulocyte adhesion and diapedesis. In other embodiments, the combination therapy comprises using ustekinumab in combination with one or more agents targeting osteoarthritis pathway. In some embodiments, the combination therapy comprises using ustekinumab in combination with one or more agents targeting role of macrophages, fibroblasts and endothelial cells in rheumatoid arthritis. In other embodiments, the combination therapy comprises using ustekinumab in combination with one or more agents targeting hepatic fibrosis and hepatic stellate cell activation. In other embodiments, the combination therapy comprises using ustekinumab in combination with one or more agents targeting inhibition of matrix metalloproteases. In some embodiments, the combination therapy comprises using ustekinumab in combination with one or more agents targeting atherosclerosis signaling. In other embodiments, the combination therapy comprises using ustekinumab in combination with one or more agents targeting bladder cancer signaling. In certain embodiments, the combination therapy comprises using ustekinumab in combination with one or more agents targeting role of pattern recognition receptors in recognition of bacteria and viruses. In other embodiments, the combination therapy comprises using ustekinumab in combination with one or more agents targeting HMGB1 signaling.

In other embodiments, the combination therapy comprises using one or more JAK inhibitors in combination with one or more agents targeting granulocyte adhesion and diapedesis. In certain embodiments, the combination therapy comprises using one or more JAK inhibitors in combination with one or more agents targeting agranulocyte adhesion and diapedesis. In other embodiments, the combination therapy comprises using one or more JAK inhibitors in combination with one or more agents targeting osteoarthritis pathway. In some embodiments, the combination therapy comprises using one or more JAK inhibitors in combination with one or more agents targeting role of macrophages, fibroblasts and endothelial cells in rheumatoid arthritis. In other embodiments, the combination therapy comprises using one or more JAK inhibitors in combination with one or more agents targeting hepatic fibrosis and hepatic stellate cell activation. In other embodiments, the combination therapy comprises using one or more JAK inhibitors in combination with one or more agents targeting inhibition of matrix metalloproteases. In some embodiments, the combination therapy comprises using one or more JAK inhibitors in combination with one or more agents targeting atherosclerosis signaling. In other embodiments, the combination therapy comprises using one or more JAK inhibitors in combination with one or more agents targeting bladder cancer signaling. In certain embodiments, the combination therapy comprises using one or more JAK inhibitors in combination with one or more agents targeting role of pattern recognition receptors in recognition of bacteria and viruses. In other embodiments, the combination therapy comprises using one or more JAK inhibitors in combination with one or more agents targeting HMGB1 signaling.

In other embodiments, the combination therapy comprises using one or more antibiotics in combination with one or more agents targeting one or more canonical pathways selected from the group consisting of granulocyte adhesion and diapedesis, agranulocyte adhesion and diapedesis, osteoarthritis pathway, role of macrophages, fibroblasts and endothelial cells in rheumatoid arthritis, hepatic fibrosis and hepatic stellate cell activation, inhibition of matrix metalloproteases, atherosclerosis signaling, bladder cancer signaling, role of pattern recognition receptors in recognition of bacteria and viruses, and HMGB1 signaling. In other embodiments, the combination therapy comprises using one or more antibiotics in combination with one or more agents targeting granulocyte adhesion and diapedesis. In certain embodiments, the combination therapy comprises using one or more antibiotics in combination with one or more agents targeting agranulocyte adhesion and diapedesis. In other embodiments, the combination therapy comprises using one or more antibiotics in combination with one or more agents targeting osteoarthritis pathway. In some embodiments, the combination therapy comprises using one or more antibiotics in combination with one or more agents targeting role of macrophages, fibroblasts and endothelial cells in rheumatoid arthritis. In other embodiments, the combination therapy comprises using one or more antibiotics in combination with one or more agents targeting hepatic fibrosis and hepatic stellate cell activation. In other embodiments, the combination therapy comprises using one or more antibiotics in combination with one or more agents targeting inhibition of matrix metalloproteases. In some embodiments, the combination therapy comprises using one or more antibiotics in combination with one or more agents targeting atherosclerosis signaling. In other embodiments, the combination therapy comprises using one or more antibiotics in combination with one or more agents targeting bladder cancer signaling. In certain embodiments, the combination therapy comprises using one or more antibiotics in combination with one or more agents targeting role of pattern recognition receptors in recognition of bacteria and viruses. In other embodiments, the combination therapy comprises using one or more antibiotics in combination with one or more agents targeting HMGB1 signaling.

In certain embodiments, the combination therapy comprises using one or more immunomodulators in combination with one or more agents targeting one or more canonical pathways selected from the group consisting of granulocyte adhesion and diapedesis, agranulocyte adhesion and diapedesis, osteoarthritis pathway, role of macrophages, fibroblasts and endothelial cells in rheumatoid arthritis, hepatic fibrosis and hepatic stellate cell activation, inhibition of matrix metalloproteases, atherosclerosis signaling, bladder cancer signaling, role of pattern recognition receptors in recognition of bacteria and viruses, and HMGB1 signaling. In other embodiments, the combination therapy comprises using one or more immunomodulators in combination with one or more agents targeting granulocyte adhesion and diapedesis. In certain embodiments, the combination therapy comprises using one or more immunomodulators in combination with one or more agents targeting agranulocyte adhesion and diapedesis. In other embodiments, the combination therapy comprises using one or more immunomodulators in combination with one or more agents targeting osteoarthritis pathway. In some embodiments, the combination therapy comprises using one or more immunomodulators in combination with one or more agents targeting role of macrophages, fibroblasts and endothelial cells in rheumatoid arthritis. In other embodiments, the combination therapy comprises using one or more immunomodulators in combination with one or more agents targeting hepatic fibrosis and hepatic stellate cell activation. In other embodiments, the combination therapy comprises using one or more immunomodulators in combination with one or more agents targeting inhibition of matrix metalloproteases. In some embodiments, the combination therapy comprises using one or more immunomodulators in combination with one or more agents targeting atherosclerosis signaling. In other embodiments, the combination therapy comprises using one or more immunomodulators in combination with one or more agents targeting bladder cancer signaling. In certain embodiments, the combination therapy comprises using one or more immunomodulators in combination with one or more agents targeting role of pattern recognition receptors in recognition of bacteria and viruses. In other embodiments, the combination therapy comprises using one or more immunomodulators in combination with one or more agents targeting HMGB1 signaling.

In another aspect, provided herein are methods of treating, managing and/or preventing an inflammatory bowel disease (IBD), which comprise administering to a patient in need of such treatment, management or prevention a therapeutically or prophylactically effective amount of anti-inflammatory treatment of the IBD, e.g., anti-tumor necrosis factor (TNF) agents. In one embodiment, the method is a method of treating an inflammatory disease or a related disorder. In one embodiment, the method is a method of managing an inflammatory disease or a related disorder. In one embodiment, the method is a method of preventing an inflammatory disease or a related disorder. In one embodiment, the inflammatory bowel disease (IBD) is Crohn's disease. In one embodiment, the inflammatory bowel disease (IBD) is ulcerative colitis.

In some embodiments, provided herein are methods for treating a subject diagnosed with an inflammatory bowel disease (IBD) with one of more of the anti-inflammatory treatment. In one embodiment of the various methods provided herein, the methods comprise administering one or more anti-inflammatory treatment to the subject diagnosed with an inflammatory bowel disease (IBD). In another embodiment of the various methods provided herein, the methods comprise administering one or more anti-inflammatory treatment to the subject determined to be likely to be responsive to the anti-inflammatory treatment using the methods provided herein.

Thus, in other embodiments, provided herein is a method of treating a subject diagnosed with an inflammatory bowel disease (IBD), comprising:

a. predicting the response of the subject to an anti-inflammatory treatment of the IBD, comprising:
 (i) contacting a sample from a subject with a set of probes capable of detecting a panel of biomarkers comprising 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3); and
 (ii) determining a pattern of the panel of biomarkers, wherein the pattern of the panel of biomarkers predicts the response to the anti-inflammatory treatment in the subject; and
b. administering the subject a therapeutically effective amount of one or more anti-inflammatory treatment.

In some embodiments, provided herein is a method of treating a subject diagnosed with an inflammatory bowel disease (IBD), comprising:

a. predicting the response of the subject to an anti-inflammatory treatment of the IBD, comprising:
 (i) contacting a sample from a subject with a set of probes capable of detecting a panel of biomarkers comprising STEAP4 metalloreductase (STEAP4) and 1, 2, 3, 4, 5, 6, 7, 8, 9, 10, 11, or 12 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3); and
 (ii) determining a pattern of the panel of biomarkers, wherein the pattern of the panel of biomarkers predicts the response to the anti-inflammatory treatment in the subject; and
b. administering the subject a therapeutically effective amount of one or more anti-inflammatory treatment.

In other embodiments, provided herein are methods for treating a subject determined to be likely to be non-responsive to an anti-inflammatory treatment of the IBD with one or more of the anti-inflammatory treatment. In one embodiment of the various methods provided herein, the methods comprise administering one or more anti-inflammatory treatment to the subject determined to be likely to be non-responsive to the anti-inflammatory treatment using the methods provided herein.

Thus, in other embodiments, provided herein is a method of treating a subject diagnosed with an inflammatory bowel disease (IBD), comprising:

a. predicting the subject to be a non-responder to an anti-inflammatory treatment of the IBD, comprising:

(i) contacting a sample from a subject with a set of probes capable of detecting a panel of biomarkers comprising 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

(ii) determining baseline gene expression levels of the panel of biomarkers in the sample; and (iii) determining the signature score for each sample; wherein the subject is predicted to be a non-responder to the anti-inflammatory treatment of the IBD if the signature score of the panel of biomarkers is below a pre-specified threshold indicative of non-response; and b. administering the subject a therapeutically effective amount of one or more anti-inflammatory treatment.

In some embodiments, provided herein is a method of treating a subject diagnosed with an inflammatory bowel disease (IBD), comprising:

a. predicting the subject to be a non-responder to an anti-inflammatory treatment of the IBD, comprising:

(i) contacting a sample from a subject with a set of probes capable of detecting a panel of biomarkers comprising STEAP4 metalloreductase (STEAP4) and 1, 2, 3, 4, 5, 6, 7, 8, 9, 10, 11, or 12 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), and zinc finger BED-type containing 3 (ZBED3);

(ii) determining baseline gene expression levels of the panel of biomarkers in the sample; and (iii) determining the signature score for each sample; wherein the subject is predicted to be a non-responder to the anti-inflammatory treatment of the IBD if the signature score of the panel of biomarkers is below a pre-specified threshold indicative of non-response; and b. administering the subject a therapeutically effective amount of one or more anti-inflammatory treatment.

In further embodiments, the panel of biomarkers for the method of treating the subject provided herein, includes CMTM2, C5AR1, FGF2, GK, HGF, IL1RN, LILRA2, NAMPT, PAPPA, SNCA, SOD2, STEAP4, and ZBED3. In some embodiments, the sample is obtained before the subject is treated with the anti-inflammatory treatment. In certain embodiments, the probe provided herein is selected from the group consisting of an aptamer, an antibody, an affibody, a peptide, and a nucleic acid. In one embodiment, the probe is a nucleic acid. In other embodiments, the probe is selected from the group consisting of SEQ ID NOS. 1-14, SEQ ID NO. 17, SEQ ID NO. 20, SEQ ID NO. 23, SEQ ID NO. 26, SEQ ID NO. 29, SEQ ID NO. 32, SEQ ID NO. 35, SEQ ID NO. 38, SEQ ID NO. 41, SEQ ID NO. 44, SEQ ID NO. 47, and SEQ ID NO. 50. Given the teachings and guidance provided herein, one skilled in the art will understand that the disclosure herein is intended to include methods of treating a subject diagnosed with an inflammatory bowel disease (IBD) with an anti-inflammatory treatment of the IBD, the methods include contacting a sample from the subject with a probe or a set of probes disclosed above.

In some embodiments, the pattern of the panel of biomarkers provided herein is determined by: (a) determining the baseline gene expression levels of the panel of biomarkers in the subject, and (b) determining the signature score for each sample. In certain embodiments, the gene expression levels are determined by quantitative polymerase chain reaction (qPCR). In other embodiments, the qPCR primers are selected from the group consisting of SEQ ID NO. 15, SEQ ID NO. 16, SEQ ID NO. 18, SEQ ID NO. 19, SEQ ID NO. 21, SEQ ID NO. 22, SEQ ID NO. 24, SEQ ID NO. 25, SEQ ID NO. 27, SEQ ID NO. 28, SEQ ID NO. 30, SEQ ID NO. 31, SEQ ID NO. 33, SEQ ID NO. 34, SEQ ID NO. 36, SEQ ID NO. 37, SEQ ID NO. 39, SEQ ID NO. 40, SEQ ID NO. 42, SEQ ID NO. 43, SEQ ID NO. 45, SEQ ID NO. 46, SEQ ID NO. 48, SEQ ID NO. 49, SEQ ID NO. 51, and SEQ ID NO. 52. Given the teachings and guidance provided herein, one skilled in the art will understand that the disclosure herein is intended to include methods of treating a subject diagnosed with an inflammatory bowel disease (IBD) with an anti-inflammatory treatment of the IBD, the methods include determining the pattern of the panel of biomarkers with any of the techniques described above.

In a further embodiment, the predicted non-responder subjects are identified as candidates for combination therapy. In another aspect, provided herein is a method of treating a subject diagnosed with an inflammatory bowel disease (IBD), comprising predicting the subject to be a non-responder to an anti-inflammatory treatment of the IBD and administering the subject a combination therapy comprising two or more therapies selected from the group consisting of anti-inflammatory treatment, antibiotics, immunomodulators, anti-diarrheal medications, pain relievers, iron supplements, and calcium and vitamin D supplements. In a further embodiment, the combination therapy comprises administering to the subject one or more agents targeting one or more canonical pathways selected from the group consisting of granulocyte adhesion and diapedesis, agranulocyte adhesion and diapedesis, osteoarthritis pathway, role of macrophages, fibroblasts and endothelial cells in rheumatoid arthritis, hepatic fibrosis and hepatic stellate cell activation, inhibition of matrix metalloproteases, atherosclerosis signaling, bladder cancer signaling, role of pattern recognition receptors in recognition of bacteria and viruses, and HMGB1 signaling. Given the teachings and guidance provided herein, one skilled in the art will understand that the disclosure herein is intended to include methods of treating a predicted non-responder subject with various combinations of one or more therapies described above.

In some embodiments, provided herein is a method of treating a subject diagnosed with an inflammatory bowel disease (IBD), the method further comprising administering to the subject one or more of the anti-inflammatory treatment of the IBD. In further embodiments, the anti-inflammatory treatment provided herein includes, but is not limited to, aminosalicylates, corticosteroids, anti-tumor necrosis factor (TNF) agents, anti-integrin agents, JAK inhibitors, and anti-interleukin agents. In one embodiment, the anti-inflammatory treatment is one or more aminosalicylate. In one embodiment, the aminosalicylate is sulfasalazine. In one embodiment, the aminosalicylate is mesalamine. In one embodiment, the aminosalicylate is olsalazine. In one embodiment, the aminosalicylate is balsalazide. In one embodiment, the anti-inflammatory treatment is one or more corticosteroid. In one embodiment, the corticosteroid is prednisone. In one embodiment, the corticosteroid is prednisolone. In one embodiment, the corticosteroid is methyl-prednisolone. In one embodiment, the anti-inflammatory treatment is budesonide. In one embodiment, the anti-inflammatory treatment is one or more anti-tumor necrosis factor (TNF) agent. In one embodiment, the anti-TNF agent is infliximab (Remicade). In one embodiment, the anti-TNF agent is adalimumab (Humira). In one embodiment, the anti-TNF agent is golimumab (Simponi). In one embodiment, the anti-inflammatory treatment is one or more anti-integrin agent. In one embodiment, the anti-integrin agent is vedolizumab. In one embodiment, the anti-integrin agent is natalizumab. In one embodiment, the anti-inflammatory treatment is one or more JAK inhibitors. In some embodiments, the JAK inhibitors are inhibitors against one or more of four JAK members: JAK1, JAK2, JAK3, and TYK2. In one embodiment, the JAK inhibitor is filgotinib. In one embodiment, the JAK inhibitor is peficitinib. In one embodiment, the JAK inhibitor is tofacitinib (Xeljanz/Jakvinus). In one embodiment, the JAK inhibitor is upadacitinib. In one embodiment, the anti-inflammatory treatment is one or more anti-interleukin agent. In some embodiments, the anti-interleukin (IL) agents include but are not limited to one or more of anti-IL-1 agents, anti-IL-6 agents, anti-IL-10 agents, anti-IL-13 agents, anti-IL-17 agents, anti-IL-12/23 agents, or anti-IL-23 agents. In one embodiment, the anti-IL agent is BI 655066. In one embodiment, the anti-IL agent is briakinumab. In one embodiment, the anti-IL agent is guselkumab. In one embodiment, the anti-IL agent is tildrakizumab. In one embodiment, the anti-IL agent is ustekinumab (Stelara).

In some embodiments, the method provided herein further comprises predicting the response by one or more other characteristics of the subject. In one embodiment, the characteristic is protein levels. In another embodiment, the characteristic is gut microbiome. In other embodiment, the characteristic is histology of the subject. In another embodiment, the characteristic is clinical characteristics of the subject.

In certain embodiments, the method provided herein further comprises measuring the response to the IBD treatment in the subject at least 6 weeks after the IBD treatment. In another embodiment, the method provided herein further comprises measuring the response to the IBD treatment in the subject more than 6 weeks after the IBD treatment. In certain embodiments, the method provided herein further comprises measuring the response to the IBD treatment in the subject 30 weeks after the IBD treatment. In certain embodiments, the method provided herein further comprises measuring the response to the IBD treatment in the subject more than 30 weeks after the IBD treatment. In other embodiments, the method provided herein further comprises measuring the response to the IBD treatment in the subject 50 weeks after the IBD treatment. In certain embodiments, the method provided herein further comprises measuring the response to the IBD treatment in the subject more than 50 weeks after the IBD treatment.

In some embodiments, the subject had previously failed or were intolerant of at least one therapy selected from the group consisting of: vedolizumab, corticosteroids, azathioprine (AZA), and 6 mercaptopurine (6 MP), or the subject had demonstrated corticosteroid dependence. In some embodiments, the subject had previously failed or was intolerant of anti-integrin treatments. In one embodiment, the subject had previously failed or was intolerant of vedolizumab. In another embodiment, the subject had previously failed or was intolerant of natalizumab. In one embodiment, the subject had previously failed or was intolerant of corticosteroids. In one embodiment, the subject had previously failed or was intolerant of prednisone. In another embodiment, the subject had previously failed or was intolerant of prednisolone. In other embodiment, the subject had previously failed or was intolerant of methylprednisolone. In one embodiment, the subject had previously demonstrated corticosteroid dependence. In another embodiment, the subject had previously demonstrated prednisone dependence. In one embodiment, the subject had previously demonstrated prednisolone dependence. In other embodiment, the subject had previously demonstrated methylprednisolone dependence. In some embodiments, the subject had previously failed or was intolerant of immunomodulators. In one embodiment, the subject had previously failed or was intolerant of AZA. In one embodiment, the subject had previously failed or was intolerant of 6 MP. In one embodiment, the subject had previously failed or was intolerant cyclosporine. In other embodiment, the subject had previously failed or was intolerant of methotrexate.

The panel of biomarkers is able to identify subsets of patients with different responses to different IBD therapies, which could be beneficial in many ways, including reduced exposure of patients to ineffective treatments, achievement of higher response rates, and the ability to treat predicted non-responder patients with alternative therapies to avoid stepping through less effective treatments. The panel of biomarkers can additionally be used for other purposes, such as to stratify patients in clinical trials, reduce sample size in proof of concept trials by excluding predicted non-responsive (NR) patients, and balance treatment arms in clinical trials ensuring that non-responders are equally represented in both arms.

Kits

Compositions for use in the methods disclosed herein include, but are not limited to, probes, antibodies, affibodies, nucleic acids, and/or aptamers. In some embodiments, compositions can detect the level of expression (e.g., mRNA or protein level) of a panel of biomarkers from a biological sample.

Any of the compositions can be provided in the form of a kit or a reagent mixture. By way of an example, labeled probes can be provided in a kit for the detection of a panel of biomarkers. Kits can include all components necessary or sufficient for assays, which can include, but is not limited to, detection reagents (e.g., probes), buffers, control reagents (e.g., positive and negative controls), amplification reagents, solid supports, labels, instruction manuals, etc. In certain embodiments, the kit comprises a set of probes for the panel of biomarkers and a solid support to immobilize the set of probes. In certain embodiments, the kit comprises a set of probes for the panel of biomarkers, a solid support, and reagents for processing the sample to be tested (e.g., reagents to isolate the protein or nucleic acids from the sample).

In one embodiment, included herein is a kit for predicting a response to a treatment in a subject diagnosed with an inflammatory bowel disease (IBD). In other embodiments, the kit comprises a set of isolated probes capable of detecting a panel of biomarkers comprising at least 1, 2, 3, 4, 5, 6, 7, 8, 9, 10, 11, 12, or 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyl-transferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3). In another embodiment, the kit comprises a set of isolated probes capable of detecting a panel of biomarkers comprising at least STEAP4 and 1, 2, 3, 4, 5, 6, 7, 8, 9, 10, 11, or 12, biomarkers selected from the group consisting of CKLF-like MARVEL trans-membrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immu-noglobulin like receptor A2 (LILRA2), nicotinamide phos-phoribosyltransferase (NAMPT), pappalysin 1 (PAPPA), synuclein alpha (SNCA), superoxide dismutase 2, mito-chondrial (SOD2), and zinc finger BED-type containing 3 (ZBED3).

In another embodiment, the kit comprises a set of isolated probes capable of detecting all biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyl-transferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3). In certain embodi-ments, the kit further comprises a therapeutic agent.

EXAMPLES

Example 1: Identification and Refinement of a Predictive Gene Expression Signature of Anti-TNF Response in IBD Patients In this example, a predictive gene expression signature of anti-TNF response was first identified in the ACT1 inflix-imab study (Remicade, a chimeric monoclonal antibody against tumor necrosis factor alpha (TNF-α)) and validated and then refined in the PURSUIT golimumab study (Sim-poni®, a human monoclonal antibody against TNF-α) for UC patients.

The gene expression signature was initially identified in the ACT1 infliximab study via comparative analysis from a subset of 22 patients who consented to participate in the optional biopsy sub-study (Arijs, et al., Gut., 2009, 58: 1612-1619). Total RNA was extracted and then analyzed with Affymetrix Human Genome U133 Plus 2.0 Arrays (Thermo Fisher Scientific's Affymetrix, Santa Clara, CA).

Baseline gene expression was evaluated for the ability to distinguish Week 8 responders (n=12) from non-responders (n=10). A set of 109 probe sets were significantly differen-tially expressed at baseline between responders and non-responders (fold change >2, P<0.05). The panel of 109 probe sets was able to predict Week 8 response with >90% sensitivity and specificity.

The predictive panel of 109 probe sets, which mapped to 81 unique genes, was then retrospectively validated in an independent cohort, the PURSUIT golimumab study (Sand-born, et al., Gastroenterology 2014, 146: 85-95), using gene expression from 59 patient biopsy samples collected at baseline. Golimumab is a human IgG1k monoclonal anti-body specific for human tumor necrosis factor alpha (TNF-a) that exhibits multiple glycoforms with molecular masses of about 150 to 151 kD. The 109 probe set panel was able to predict mucosal healing response at Week 6 in PURSUIT (n=59) with an area under the curve ($AUC_{ROC}$) of 0.762.

The predictive panel of 109 probe sets was then refined in the same PURSUIT golimumab study. A 13-gene signature (Table 1) achieved the maximum area under the receiver operating characteristic (ROC) curve ($AUC_{ROC}$) value for predicting Week 6 mucosal healing response ($AUC_{ROC}$ of 0.768). The 13 gene signature is referred to as the molecular prediction signature (MPS). These genes represented bio-logical processes associated with inflammatory response, oxidative stress, and cell motility, with higher baseline expression of these genes in mucosal healing non-respond-ers compared with mucosal healing responders.

TABLE 1

| Genes included in the MPS Panel | |
| --- | --- |
| Gene Symbol | Gene Name |
| cmtm2 | CKLF-like MARVEL transmembrane domain containing 2 |
| c5ar1 | complement C5a receptor 1 |
| fgf2 | fibroblast growth factor 2 |
| gk | glycerol kinase |
| hgf | hepatocyte growth factor |
| il1rn | interleukin 1 receptor antagonist |
| lilra2 | leukocyte immunoglobulin like receptor A2 |
| nampt | nicotinamide phosphoribosyltransferase |
| pappa | pappalysin 1 |
| snca | synuclein alpha |
| sod2 | superoxide dismutase 2, mitochondrial |
| steap4 | STEAP4 metalloreductase |
| zbed3 | zinc finger BED-type containing 3 |

Example 2: Gene Expression Signature for Prediction of Golimumab Response in a Phase 2a Open-Label Trial of Patients with Ulcerative Colitis A phase 2a open label study of 103 golimumab-treated patients with moderate-to-severe UC (PROgECT) (Telesco S E, et al., Gastroenterology, 2018 October, 155(4):1008-1011.e8; and ClinicalTrials.gov no. is NCT01988961, the disclosure of each of the references is incorporated herein by reference in its entirety) was designed and conducted to confirm that the MPS can be used to predict which patients would achieve mucosal healing, clinical response, and clini-cal remission at weeks 6 and 30 of treatment. Post hoc objectives were to confirm the accuracy of the MPS to predict sustained mucosal healing, sustained clinical response, and sustained clinical remission (the sustained endpoints were defined as meeting the respective response criterion at both Weeks 6 and 30).

Materials and Methods

Study design: Eligible patients had an established diagnosis of UC (for at least 3 months) and moderate-to-severe disease activity, defined as a Mayo score of 6 to 12, inclusive, with an endoscopic subscore (based on the endoscopy subscore assigned by central readers). Patients had an inadequate response to, or had failed to tolerate, 1 or more of the following conventional therapies: oral 5-aminosalicylates, oral corticosteroids, azathioprine, and/or 6-mercaptopurine; or were corticosteroid dependent (i.e., were unable to taper corticosteroids without recurrence of UC symptoms).

All patients enrolled in the study received the approved induction dose regimen of subcutaneous (SC) golimumab: 200 mg at Week 0 (baseline) and 100 mg at Week 2. At Week 6 and thereafter through Week 50, patients received the maintenance dose of SC golimumab that was approved for UC in the country (either 100 mg every 4 weeks [q4w] or 50 mg q4w) where the patient's treatment was administered. In countries where golimumab was not approved for patients with UC, a maintenance dose of 100 mg q4w was used. Following an 8-week screening, the treatment phase of the study was 50 weeks, followed by an 8-week safety follow-up with a final safety visit at Week 58 (FIG. 1). Patients who were receiving oral 5-aminosalicylates or immunomodulators (6-mercaptopurine, azathioprine, and methotrexate) at the time of entry into the study kept their prescribed dosage stable throughout the study (unless dosage reduction or discontinuation was required due to toxicity or medical necessity). Patients receiving oral corticosteroids (at a maximum dose of 40 mg) kept the prescribed dosage stable through Week 6, after which the dose could be tapered at the discretion of the investigator.

Study Evaluation: To assess disease activity, Mayo scores were calculated at baseline, Week 6, and Week 30. Patient eligibility at baseline and the analysis of the treatment effect at Week 6 and Week 30 were based on the endoscopy subscore provided by a central reader selected from a panel of 3 independent central readers who were blinded to patient number and visit. The assigned endoscopic assessments were based on the worst findings identified in the bowel during the endoscopy procedure. Patients at high risk of colon cancer were assessed by colonoscopy; sigmoidoscopy was acceptable for all other patients. For the scoring of rectal bleeding and stool frequency, the mean sub score from the most recent consecutive 3 days before the study visit was used.

Biopsy Sample Processing for Predictive Analyses: Biopsy samples (collected 15 to 20 cm from the anal verge) taken at screening were used to extract total RNA and measure the expression levels of the MPS using the QuantStudio qPCR platform (Thermo Fisher Scientific, Waltham, MA) with primers listed in Table 2. A signature score based on the MPS was generated for each patient.

Biomarker Sample Analysis: Serum samples were collected at baseline and Weeks 6, 30, and 50 for analysis of C-reactive protein (CRP) concentrations. Stool samples were collected at baseline and Weeks 6, 30, and 50 for fecal lactoferrin and calprotectin concentration determinations.

Pharmacokinetic and Immunogenicity Sample Analysis: Serum samples were collected at baseline and Weeks 6, 30, and 50 for analysis of golimumab concentrations. Serum golimumab was detected using a validated electrochemiluminescence assay with a lowest quantifiable concentration of 0.039 µg/mL. Blood samples for the detection of anti golimumab antibodies (using a validated drug intolerant immunoassay) were collected at baseline and Weeks 6, 30, and 50. Patients were classified as positive if antibodies were detected at any time in their serum sample.

Safety Evaluations: Adverse events (AEs), including infections and injection site reactions, clinical laboratory tests, and concomitant medication use were recorded throughout the study.

Statistical Methods: Demographics and baseline disease characteristics were summarized for all treated patients. Efficacy analyses were based on all treated patients, and biomarker analyses were performed for treated patients who had biomarker measurement at baseline. Safety analyses were summarized for all treated patients. The primary hypothesis was that the $AUC_{ROC}$ of the MPS to predict mucosal healing (endoscopy subscore of 0 or 1) at Week 6 would be significantly greater than 0.5 (indicating accuracy better than chance; higher $AUC_{ROC}$ value reflects greater predictive ability).

TABLE 2

| Gene Name | Target or Reference | qPCR Assay ID | Probe Seq | F. Primer Seq | R. Primer Seq |
|---|---|---|---|---|---|
| GK_JC1 | Target | AID1URP | CACGATGGAGCGGTTTGAA (SEQ ID NO: 14) | TCATCACAGCTTTCTTCC ATGTAGA (SEQ ID NO: 15) | ATTAATGCGGAGGAAAGT (SEQ ID NO: 16) |
| FGF2_JC1 | Target | AIX01J5 | CAAAGGAGTGTGTGCTAACC GTTA (SEQ ID NO: 17) | ACACTCATCCGTAACACA TTTAGAAGC (SEQ ID NO: 18) | TGGCTATGAAGGAAGATG (SEQ ID NO: 19) |
| HGF | Target | Hs00900073_m1 | CAAGTGCAAGGACCTACG (SEQ ID NO: 20) | CGAGCATGACATGACTCC TGAAAAT (SEQ ID NO: 21) | CCATCTGGATTTCGGCAGTA ATTTT (SEQ ID NO: 22) |
| ZBED3 | Target | Hs00995410_m1 | CCCGCACGCTTTAAAT (SEQ ID NO: 23) | ACAGGGACCCCAGAATCC TT (SEQ ID NO: 24) | GCTCGCCACTCCTCATTCTG (SEQ ID NO: 25) |
| CMTM2 | Target | Hs00376242_g1 | CAGCCCAAACTCCG (SEQ ID NO: 26) | GGGCACGCTGAGATCAAG ATT (SEQ ID NO: 27) | GAGGACAACAGTATCATTGC AGCTA (SEQ ID NO: 28) |

TABLE 2-continued

MPS PCR Sequences and Probe Sequences for qPCR

| Gene Name | Target or Reference | qPCR Assay ID | Probe Seq | F. Primer Seq | R. Primer Seq |
|---|---|---|---|---|---|
| NAMPT | Target | Hs00237184_m1 | CGACTCCTACAAGGTTAC (SEQ ID NO: 29) | CAGAAGCCGAGTTCAACA TCCT (SEQ ID NO: 30) | GCTTGTGTTGGGTGGATATTG TTTA (SEQ ID NO: 31) |
| IL1RN | Target | Hs00893626_m1 | CTGGAGGCAGTTAACATC (SEQ ID NO: 32) | CTGTGTCAAGTCTGGTGA TGAGA (SEQ ID NO: 33) | CTGTTCTCGCTCAGGTCAGT (SEQ ID NO: 34) |
| LILRA2_JC1 | Target | AIFASXX | CAGCCACAATCACTCATCAG AGTA (SEQ ID NO: 35) | GGTTTGCTGTAGGCTCCT GTCA (SEQ ID NO: 36) | TGACCCCCTGGAGCT (SEQ ID NO: 37) |
| SNCA | Target | Hs00240906_m1 | CTCAGCCACTGTTGC (SEQ ID NO: 38) | GGAGGGAGTGGTGCATGG T (SEQ ID NO: 39) | CATTTGTCACTTGCTCTTTGG TCTT (SEQ ID NO: 40) |
| C5AR1_CLT | Target | AIAAZ80 | GGCAGGAGGGACCTTCGA (SEQ ID NO: 41) | GGGTGGTATAATTGAAGG AGTTC (SEQ ID NO: 42) | CCAGGAGACCAGAACAT (SEQ ID NO: 43) |
| PAPPA | Target | Hs01032305_m1 | ACACTCCGACCCTATGGC (SEQ ID NO: 44) | GCAGTGCCCTGATGGCTA T (SEQ ID NO: 45) | GATGATGGACTCGCTGTTGT G (SEQ ID NO: 46) |
| SOD2 | Target | Hs01553554_m1 | CTCCCCTTTGGGTTCTC (SEQ ID NO: 47) | GGACAAACCTCAGCCCTA ACG (SEQ ID NO: 48) | AGTCACGTTTGATGGCTTCCA (SEQ ID NO: 49) |
| STEAP4 | Target | Hs01026582_m1 | TCGGCAGGTGTTTGTG (SEQ ID NO: 50) | GTCAGGAGCACTGGATGC AA (SEQ ID NO: 51) | CTTGGCTTTGCTGTCATTTCC A (SEQ ID NO: 52) |
| PUM1_A4 | Reference | Hs00472881_m1 | CTGAATGATCTGATGTTCCC (SEQ ID NO: 53) | GGTGATCAATGGCGAGAC TAG (SEQ ID NO: 54) | GGTCTTCTCTGCACCATGATT GG (SEQ ID NO: 55) |
| GUSB_A4 | Reference | Hs99999908_m1 | CGTCGGTGACTGTTC (SEQ ID NO: 56) | CTCATTTGGAATTTTGCC GATT (SEQ ID NO: 57) | CCGAGTGAAGATCCCCTTTTT A (SEQ ID NO: 58) |
| HPRT1_A4 | Reference | Hs02800695_m1 | TCAGTCCTGTCCATAATTA (SEQ ID NO: 59) | GCTGAGGATTTGGAAAGG GTGTTTA (SEQ ID NO: 60) | CCTTCATCACATCTCGAGCA AGAC (SEQ ID NO: 61) |
| IPO8_A2 | Reference | Hs00914041_m1 | CAGATACAAGCTAAGGAATA TA (SEQ ID NO: 62) | TGCCCTTGCTCTTCAGTC TTTAATT (SEQ ID NO: 63) | GGCCTCACATGTGGCTTCA (SEQ ID NO: 64) |

A ROC curve was constructed by plotting the true positive fraction (sensitivity) versus the false-positive fraction (1—specificity), based on results obtained with the MPS, using all possible thresholds of MPS positivity (Hajian-Tilaki, J. Intern. Med., 2013, 4: 627-635). The $AUC_{ROC}$ was estimated using a nonparametric approach to determine the accuracy of the MPS to predict the efficacy outcome of interest (mucosal healing, clinical remission, or clinical response) (Hanley, et al., Radiology, 1982, 143: 29-36). The estimated $AUC_{ROC}$, along with its 1 sided 95% CI and p-value, is provided (null hypothesis: $AUC_{ROC}$ of 0.5).

As part of the primary analysis, sensitivity (with 95% confidence interval [CI] and P) and specificity using pre specified thresholds (Threshold A: 3.8234 [optimal balance between sensitivity and specificity] and Threshold B: 1.0000 [optimal positive predictive value]) were calculated. Similar analyses to those performed for the primary endpoint were conducted for major secondary endpoints, which include the accuracy of the MPS in predicting clinical response at Weeks 6 and 30, clinical remission at Weeks 6 and 30, and mucosal healing at Week 30. Analyses were not adjusted for multiplicity.

Descriptive summary statistics, such as n, mean, median, and SD for continuous variables and counts and percentages for discrete variables, were used to summarize most data. The nonparametric Mann-Whitney U statistics was used to estimate the $AUC_{ROC}$, its 1-sided 95% CI, and the associated P.

Serum Golimumab Concentration: For Week 6 analyses of the relationship between serum golimumab concentration and the MPS, in those subjects included in MPS analyses, the following categories were used: Quartile 1 (≤0.84 μg/mL), Quartile 2 (>0.84 and ≤1.80 μg/mL), Quartile 3 (>1.80 and ≤3.45 μg/mL), and Quartile 4 (>3.45 μg/mL).

Results

Mucosal Healing, Clinical Response, and Clinical Remission: Of the 103 patients, 99 patients were included in the efficacy analysis (4 patients from 1 site were excluded from efficacy analyses due to site compliance issues). At Week 6, after completion of the induction phase, 24.2% (24/99) of patients achieved mucosal healing, while clinical remission was observed in 13.1% (13/99) of patients. Approximately half of the patients (52.5% [52/99]) achieved clinical response at Week 6.

At Week 30, similar proportions of patients achieved mucosal healing (28.3% [28/99]) and clinical response (48.5% [48/99]) as observed for Week 6; clinical remission was observed in almost twice as many patients (22.2% [22/99]). Sustained mucosal healing was achieved in 14.1% (14/99) of patients, while sustained clinical response and clinical remission were achieved in 30.3% (30/99) and 5.1% (5/99) of patients, respectively. The sustained endpoints were defined as meeting the respective response criterion at both Weeks 6 and 30. The median Mayo score remained at 6 throughout the study.

Primary Endpoint: A receiver operating characteristic (ROC) curve for MPS was generated for mucosal healing based on the fraction of true positives and false positives at Week 6. The $AUC_{ROC}$ was 0.688 (P=0.002; Table 3), indicating a better than chance accuracy of the MPS to predict Week 6 mucosal healing. Two thresholds were applied (Threshold A: −3.8234; Threshold B: 1.0000) to dichotomize patients into mucosal healing responder or non-responder (see Statistical Methods for explanation of threshold selection). An analysis based on Threshold A showed superior sensitivity: 1.000, with a lower bound of 95% confidence interval (CI) of 0.878, P<0.001, and a low specificity of 0.186. An analysis based on Threshold B also showed superior sensitivity: 0.870, with a lower bound of 95% CI of 0.696, P<0.001, and a low specificity of 0.343.

Secondary Endpoint: Additionally, the MPS predicted mucosal healing at Week 30 ($AUC_{ROC}$: 0.671, P=0.006, lower bound of 95% CI: 0.569; Table 3). In contrast, the ROC curves for clinical response at Weeks 6 and 30 and for clinical remission at Week 6 showed that the accuracy of prediction was no better than chance (Table 3). Prediction of clinical remission at Week 30 showed a positive trend ($AUC_{ROC}$: 0.633, P=0.059; Table 3).

TABLE 3

MPS Prediction of Primary and Secondary Endpoints

| Parameter | $AUC_{ROC}$ | Lower Bound of 1-sided 95% CI | 1-sided P |
|---|---|---|---|
| Week 6 (N = 93) | | | |
| Mucosal healing | 0.688 | 0.589 | .002 |
| Clinical response | 0.520 | 0.419 | .740 |
| Clinical remission | 0.558 | 0.429 | .462 |
| Week 30 (N = 93) | | | |
| Mucosal healing | 0.671 | 0.569 | .006 |
| Clinical response | 0.588 | 0.488 | .148 |
| Clinical remission | 0.633 | 0.517 | .059 |

Abbreviations: $AUC_{ROC}$ = area under the receiver operating characteristic curve; CI = confidence interval; MPS = molecular prediction signature; N = number of patients.
Note:
Of the 103 treated patients, 93 patients were included in the primary analysis (4 patients from 1 site were excluded due to site compliance issues and 6 patients from other sites were excluded due to lack of valid biomarker samples).

Post Hoc Endpoint: The accuracy of the MPS to predict sustained mucosal healing was better than chance (14.1% of patients; $AUC_{ROC}$: 0.750, lower bound of 95% CI: 0.639, and P<0.001), while the ability to predict sustained clinical response (30.3% of patients; $AUC_{ROC}$: 0.516, lower bound of 95% CI: 0.403, and P=0.811) or sustained clinical remission (5.1% of patients; $AUC_{ROC}$: 0.590, lower bound of 95% CI: 0.333, and P=0.565) was not significant.

There was a subset of patients who were assigned an endoscopy score of 2 by the central reader and were assigned a score of 1 by the local reader. By restricting the predictive analysis to only those patients at the extremes of the endoscopy scale (endoscopy score=0 or 3), the mucosal healing endpoint can be better predicted by the MPS. Therefore, a post hoc analysis was performed to show that removing the patients with scores of 1 and 2 would improve the accuracy of the MPS in predicting mucosal healing response. A total of 44 patients met the criteria for this analysis (n=9 patients with a Week 6 endoscopy score of 0; n=35 patients with a Week 6 endoscopy score of 3). The MPS was able to predict mucosal healing in this subset of patients with an $AUC_{ROC}$ of 0.778 (95% CI lower bound: 0.626).

Additional post hoc analysis was performed to determine whether serum golimumab concentrations were associated with the predictive performance of the MPS. Patients were divided into quartiles based on their serum drug concentrations at Week 6. An $AUC_{ROC}$ value based on the MPS was derived for each quartile separately. However, there was no consistent trend to suggest that low serum drug concentrations contributed to the low specificity of the MPS (Table 4). Additionally, the proportion of patients who were false positives at Week 6 (patients whom the MPS predicted to be mucosal healing responders but did not respond) were assessed in terms of their Week 6 serum drug concentrations. There was a greater number of false-positive patients in the 2 lower dose quartiles compared to the 2 upper dose quartiles; this trend was statistically significant.

Finally, patients who exhibited anti-drug antibodies prior to the Week 30 visit were excluded from the MPS prediction of Week 30 mucosal healing. A total of 71 patients met the criteria for this analysis. The MPS was able to predict mucosal healing in this subset of patients with an $AUC_{ROC}$ of 0.670 (95% CI lower bound: 0.547).

TABLE 4

MPS Prediction (Threshold B = 1.0000) of Mucosal Healing per Week 6 PK Quartile

| | Quartile 1 | Quartile 2 | Quartile 3 | Quartile 4 |
|---|---|---|---|---|
| $AUC_{ROC}$ | 0.818 (0.603, 0.946) | 0.579 (0.362, 0.775) | 0.833 (0.621, 0.954) | 0.675 (0.445, 0.857) |
| Sensitivity | 1.000 (0.852, NaN) | 0.800 (0.588, 0.934) | 1.000 (0.852, NaN) | 0.778 (0.552, 0.925) |
| Specificity | 0.364 (0.176, 0.588) | 0.211 (0.073, 0.424) | 0.600 (0.377, 0.796) | 0.231 (0.080, 0.458) |

Quartile 1 (≤0.84 µg/mL), Quartile 2 (>0.84 and ≤1.80 µg/mL), Quartile 3 (>1.80 and ≤3.45 µg/mL), and Quartile 4 (>3.45 µg/mL)
Abbreviations: $AUC_{ROC}$ = area under the receiver operating characteristic curve; MPS = molecular prediction signature; N = number of patients; NaN = not a number; PK = pharmacokinetic.

Conclusion

The PROgECT study showed the ability of a gene transcript panel measured in colon biopsies to predict golimumab mucosal healing response in patients with moderate-to-severe UC. The predictive performance of the MPS was examined by estimating the $AUC_{ROC}$, and results showed that the MPS was statistically significantly better than chance at predicting mucosal healing at both Weeks 6 and 30. The driver of the overall MPS performance was the high sensitivity of the panel. However, the specificity of the MPS was lower in PROgECT than in PURSUIT, reflecting a high false positive rate, or over-prediction of mucosal healing responders.

Despite the low specificity of the MPS in predicting responders in this trial, the MPS demonstrated high accuracy in predicting non-responders to treatment as reflected by a high negative predictive value (NPV) of 0.85. This study demonstrated the first prospectively validated predictive biomarker that could accurately identify a distinct subset of patients responding to anti-TNF therapy.

Example 3: Utility of MPS to Identify Non-Responders to Golimumab Therapy in Japan PURSUIT-J study (NCT01863771) (Hibi, et al., J. Gastroenterol., 2017, 52: 1101-1111) was a phase 3 multicenter, placebo-controlled, double-blind, randomized-withdrawal study to evaluate the safety and efficacy of golimumab maintenance therapy in Japanese subjects with moderate-to-severe UC. The MPS was applied to the baseline gene expression data generated in the Japanese study to predict mucosal healing at week 6.

Methods and Materials

Two colon biopsy samples were collected per patient at baseline and stored in RNALater (Qiagen). RNA extraction was performed on the QIASymphony SP module and samples were eluted in a volume of 100 µL. The samples were subjected to analysis by quantitative polymerase chain reaction (qPCR) on the QuantStudio Dx system using a panel of genes which included the 13 genes comprising the MPS. All samples were processed as biological replicates. Following quality control, a total of 35 biopsy samples representing 18 patients were available for analysis.

An MPS score was calculated for each patient based on the baseline expression levels of the 13 genes, as described previously. A threshold of −3.8234 (Threshold A, which maximized the sum of sensitivity and specificity) or 1.0000 (Threshold B, which maximized the positive predictive value) was applied to dichotomize patients into responder or non-responder for mucosal healing, as described in Example 2. A receiver operating characteristic (ROC) curve was constructed by plotting the true positive fraction (sensitivity) versus the false-positive fraction (1-specificity), based on results obtained with the MPS, using all possible thresholds of MPS positivity. The area under the ROC curve ($AUC_{ROC}$) was estimated using a nonparametric approach to determine the accuracy of the MPS to predict mucosal healing. Performance metrics, including sensitivity, specificity, PPV, and NPV, were calculated.

Results

Figure 2:
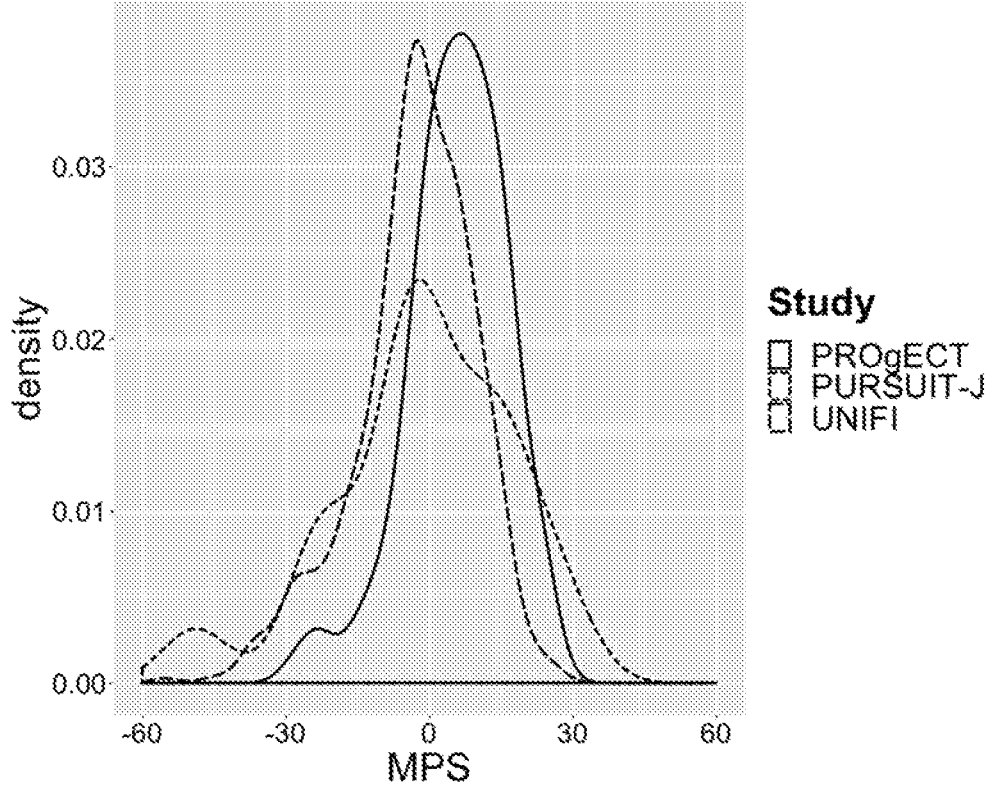
FIG. 2 shows the distribution of the molecular prediction signature (MPS) in the PROgECT, PURSUIT, and UNIFI cohorts.

Comparison of the Japan cohort compared with the PROgECT cohort in Example 2 showed that the two datasets have similar distributions of expression of the 13 genes comprising the MPS (FIG. 2), showing the generalizability of the assay and permitting the same threshold to be used for identifying responders and non-responders. The NPV of the MPS was high in the Japanese cohort, which validates the previous finding in an independent cohort that the MPS was a highly accurate tool in distinguishing a distinct subset of non-responders to golimumab prior to treatment.

As described above, the MPS was tested in multiple additional clinical cohorts, including studies in Examples 1 and 2. Table 5 summarizes the performance of the MPS in all studies with TNF antagonist therapy evaluated to date.

The performance of the MPS in predicting mucosal healing at week 6 of treatment in the Japanese cohort produced an $AUC_{ROC}$ of 0.79 (0.55, 1.00), sensitivity of 0.63 (0.31, 0.86), specificity of 0.80 (0.49, 0.94), and NPV of 0.73 (Table 5). This NPV is comparable to those observed in the initial studies used to establish the MPS.

TABLE 5

| | | | | | | | | |
|---|---|---|---|---|---|---|---|---|
| The predictive performance of the MPS in all clinical studies evaluated | | | | | | | | |
| Clinical Study | Number of patients with available gene expression data | % True Mucosal Healing Responders | % Predicted Mucosal Healing Responders | AUC | Sensitivity | Specificity | PPV | NPV |
| ACT1 | 22 | 54.55% | 59.10% | 0.92 (0.80, 1.00) | 0.83 (0.55, 0.95) | 0.7 (0.40, 0.89) | 0.77 (0.50, 0.92) | 0.78 (0.45, 0.94) |
| PURSUIT-SC | 59 | 47.50% | 52.50% | 0.76 (0.63, 0.89) | 0.79 (0.60, 0.90) | 0.71 (0.53, 0.84) | 0.71 (0.53, 0.84) | 0.79 (0.60, 0.90) |
| PROgECT | 93 | 24.73% | 70.97% | 0.69 (0.57, 0.81) | 0.87 (0.68, 0.95) | 0.34 (0.24, 0.46) | 0.30 (0.21, 0.42) | 0.89 (0.72, 0.96) |
| PURSUT-J | 18 | 44.44% | 38.88% | 0.79 (0.55, 1.00) | 0.63 (0.31, 0.86) | 0.80 (0.49, 0.94) | 0.71 (0.36, 0.92) | 0.73 (0.43, 0.90) |

Footnotes:

MPS threshold = 1.0000

The endpoint predicted by the MPS is mucosal healing at week 6 for all studies, except for ACT1 (mucosal and histologic response at week 8)

In the Japan study, the MPS was applied to 35 biopsy samples representing 18 unique patients.

Example 4A: Predictive Performance of MPS in Stelara Treatment for Crohn's Disease Methods and Materials A total of 326 intestinal biopsy samples were collected before treatment from 306 patients enrolled in a clinical trial of Stelara® (ustekinumab) in Crohn's disease, who had previously failed anti-TNF therapy. Ustekinumab is a human IgG1κ monoclonal antibody against the p40 subunit of the IL-12 and IL-23 cytokines. RNA was extracted and the samples were profiled on the Fluidigm BioMark HD platform using a panel including the 13 genes. Samples representing 144 patients were collected from terminal ileum and 162 from rectum. Missing and high data (>25 cycles) were removed from the data matrix. Samples were normalized to the input amount and technical replicates were averaged. Values >30 cycles were removed and the data were normalized to the reference genes. Signature scores were generated using the expression levels of the genes comprising the predictive 13-gene model.

The predictive performance of the 13-gene model was assessed separately in the ileum and rectum samples. In the rectum samples from drug-treated patients, the 13-gene model was able to predict endoscopic improvement at week 8 with an area under the receiver operating curve (AUC) of 0.64 (Table 6). Whereas in the rectum samples from placebo patients, the AUC was only 0.51 and therefore not significantly better than chance. In the ileum samples, the 13-gene model was able to predict endoscopic response at week 8 with an AUC of 0.64 and a negative predictive value (NPV) of 0.85.

These results demonstrated that the predictive 13-gene signature can translate from UC to Crohn's disease, from bio-failure to bio-naïve patients, and from anti-TNF therapy to IL-12/23 blockade.

Example 4B: Predictive Performance of MPS in Stelara Treatment for UC

Methods and Materials

A total of 551 colonic biopsy samples were collected before treatment from 551 unique patients enrolled in a clinical trial of Stelara® (ustekinumab) in moderate to severe ulcerative colitis. RNA was extracted and the samples were profiled on the Fluidigm BioMark HD platform using a panel including the 13 genes. Missing and high data (>25 cycles) were removed from the data matrix. Samples were normalized to the input amount and technical replicates were averaged. Values >30 cycles were removed and the data were normalized to four reference genes. Signature scores were generated using the expression levels of the genes comprising the predictive 13-gene model.

The predictive performance of the 13-gene model was assessed separately in drug-treated and placebo samples. The 13-gene model was able to predict endoscopic response at week 8 with an area under the receiver operating curve (AUC) of 0.71 in the drug-treated patients and an AUC of 0.70 in placebo patients (Table 7). The predictive performance of the 13-gene model is similar between drug-treated

TABLE 6

Performance metrics of the 13-gene signature in the drug-treated rectum samples against 4 endpoints (endoscopic response, endoscopic improvement, clinical response by CDAI, and clinical remission)

|  | Endoscopic Response WK 8 | Endoscopic Improvement WK 8 | Clinical Response WK 8 | Clinical Remission WK 8 |
|---|---|---|---|---|
| AUC | 0.56 (0.44, 0.67) | 0.64 (0.52, 0.75) | 0.48 (0.37, 0.59) | 0.49 (0.39, 0.60) |
| Sensitivity | 0.55 (0.43, 0.67) | 0.6 (0.48, 0.71) | 0.02 (0.00, 0.07) | 0.49 (0.38, 0.59) |
| Specificity | 0.58 (0.46, 0.70) | 0.64 (0.52, 0.75) | 1.00 (0.96, NaN) | 0.59 (0.48, 0.69) |
| PPV | 0.33 (0.23, 0.45) | 0.67 (0.55, 0.77) | 1.00 (0.96, NaN) | 0.43 (0.32, 0.53) |
| NPV | 0.78 (0.66, 0.86) | 0.57 (0.45, 0.68) | 0.42 (0.32, 0.53) | 0.65 (0.54, 0.74) |
| Threshold | 31.5422 | 30.0589 | 40.5491 | 31.9711 |
| Response Rate | 20/73 | 40/73 | 53/91 | 35/91 |

Additionally, the 13-gene signature was applied to a clinical cohort of bio-naïve patients treated with Stelara. A total of 179 samples were available for analysis, representing 63 unique patients. The signature demonstrated an AUC of 0.77 for predicting endoscopic response at week 8 in ileum samples from drug-treated patients.

and placebo cohort. The 13-gene model was also able to predict clinical remission at week 8 with an AUC of 0.70 in the drug-treated subjects but not in the placebo subjects. The low percentage of clinical remitters at week 8 (6%) in placebo subjects might contribute to a low value AUC of 0.57.

TABLE 7

Performance metrics of the 13-gene signature in the colonic samples against 3 endpoints (endoscopic response, clinical response, and clinical remission)

|  | Ustekinumab | | | Placebo | | |
|---|---|---|---|---|---|---|
|  | Endoscopic Response WK 8 | Clinical Response WK 8 | Clinical Remission WK 8 | Endoscopic Response WK 8 | Clinical Response WK 8 | Clinical Remission WK 8 |
| AUC | 0.71 (0.66, 0.77) | 0.59 (0.53, 0.65) | 0.70 (0.63, 0.78) | 0.70 (0.60, 0.80) | 0.60 (0.51, 0.69) | 0.57 (0.40, 0.75) |

TABLE 7-continued

Performance metrics of the 13-gene signature in the colonic samples against
3 endpoints (endoscopic response, clinical response, and clinical remission)

| | Ustekinumab | | | Placebo | | |
|---|---|---|---|---|---|---|
| | Endoscopic Response WK 8 | Clinical Response WK 8 | Clinical Remission WK 8 | Endoscopic Response WK 8 | Clinical Response WK 8 | Clinical Remission WK 8 |
| Sensitivity | 0.86 (0.76, 0.92) | 0.65 (0.58, 0.72) | 0.84 (0.70, 0.93) | 0.70 (0.51, 0.85) | 0.64 (0.50, 0.76) | 0.60 (0.26, 0.88) |
| Specificity | 0.49 (0.43, 0.55) | 0.50 (0.42, 0.58) | 0.45 (0.40, 0.51) | 0.45 (0.37, 0.54) | 0.46 (0.37, 0.55) | 0.43 (0.35, 0.51) |
| PPV | 0.33 (0.27, 0.40) | 0.61 (0.54, 0.67) | 0.19 (0.14, 0.15) | 0.21 (0.13, 0.30) | 0.37 (0.27, 0.47) | 0.06 (0.02, 0.12) |
| NPV | 0.92 (0.87, 0.96) | 0.55 (0.47, 0.63) | 0.95 (0.90, 0.98) | 0.88 (0.78, 0.94) | 0.72 (0.60, 0.82) | 0.95 (0.87, 0.99) |
| Response Rate | 0.23 (83/364) | 0.54 (197/364) | 0.13 (49/364) | 0.17 (30/176) | 0.33 (58/176) | 0.06 (10/176) |

The predictive performance of the 13-gene signature for endoscopic response at week 8 was also evaluated by biologic failure status. Higher AUC and NPV values were observed in both drug-treated and placebo subjects who had a history of biologic failure compared to those who did not have a history of biologic failure (Table 8). The specificity was higher for subjects who were biologic failures compared with those who were not biologic failures (0.55 and 0.43 in drug-treated subjects, respectively).

non-responders, 56 predicted responders) from the PROgECT study were run on Affymetrix HG-U133 Plus 2.0 arrays. Probe sets were normalized using the Robust Multi-array Average (RMA) algorithm (Irizarry, et al., Biostatistics, 2003, 4: 249-64). Differential gene expression was carried out using limma (Ritchie, et al., Nucleic Acids Res, 2015, 43: e47). Gene set variation analysis (GSVA (Hanzelmann, et al., BMC Bioinformatics, 2013, 14: 7)) was performed on UC Disease Profile (Li, et al., J. Pediatr.

TABLE 8

Performance metrics of the 13-gene signature in predicting
endoscopic response at week 8 by biologic failure status

| | Bio-failure | | Bio-Nonfailure | |
|---|---|---|---|---|
| | Ustekinumab | Placebo | Ustekinumab | Placebo |
| AUC | 0.75 (0.66, 0.85) | 0.80 (0.66, 0.95) | 0.67 (0.59, 0.76) | 0.63 (0.49, 0.77) |
| Sensitivity | 0.87 (0.70, 0.96) | 0.78 (0.40, 0.97) | 0.85 (0.72, 0.93) | 0.67 (0.43, 0.85) |
| Specificity | 0.55 (0.46, 0.63) | 0.55 (0.43, 0.67) | 0.43 (0.35, 0.52) | 0.34 (0.23, 0.47) |
| PPV | 0.28 (0.19, 0.38) | 0.17 (0.07, 0.32) | 0.38 (0.29, 0.47) | 0.23 (0.13, 0.36) |
| NPV | 0.95 (0.89, 0.99) | 0.95 (0.85, 0.99) | 0.88 (0.77, 0.94) | 0.77 (0.59, 0.90) |
| Response Rate | 0.17 (31/183) | 0.11 (9/85) | 0.29 (52/181) | 0.23 (21/91) |

Note: Threshold = −3.84

Comparison of the Stelara cohort (UNIFI) compared with the PROgECT cohort in Example 2 and PURSUIT-J cohort in Example 3 showed that the three datasets have similar distributions of expression of the 13 genes comprising the MPS (FIG. 2), showing the generalizability of the assay and permitting the same threshold to be used for identifying responders and non-responders.

These results demonstrated that the predictive 13-gene signature can translate from UC to Crohn's disease, from bio-failure to bio-naïve patients, and from anti-TNF therapy to IL-12/23 blockade (i.e. Stelara).

Example 5: Characterization of Molecular Profile of the Predicted Non-Responders in PROgECT Study The molecular profile of the predicted non-responder patients in PROgECT study of Example 2 were characterized using gene expression and microbiome data.

Methods and Materials

Microarray Analysis: 82 RNA samples from colon biopsies collected at baseline (26 predicted mucosal healing Gastroenterol Nutr., 2018, 66) and hallmark signatures from the molecular signatures database (MSigDB release 6.1, (Liberzon, et al., Cell Syst, 2015, 1: 417-25)). Analysis of functional enrichment was performed using Ingenuity Pathway Analysis (IPA; Ingenuity Inc., Chicago, IL).

16S Microbiome Analysis: Stool samples were collected from 82 patients at baseline (26 predicted mucosal healing non-responders, 56 predicted responders) from the PROgECT study and were frozen at −80 degrees. Genomic DNA (gDNA) was extracted from fecal samples using the DNeasy® PowerSoil® HTP 96 Kit (Qiagen) according to manufacturer's instructions. 16S rRNA libraries were generated using established primers and protocols (Kozich, et al., Appl. Environ. Microbiol., 2013, 79: 5112-20). Purified libraries were validated and quantitated using the HT DNA NGS 3K Reagent Kit on the LabChip GX Touch HT (Perkin Elmer) and then pooled in equimolar concentrations. Sequence-ready library pools were quantified by qPCR using the Library Quantification Kit—Illumina/ROX Low (Kapa Biosystems) on the ViiA 7 Real-Time PCR System (Applied Biosystems) according to manufacturer's instructions. The quantified library pools, along with Illumina generated PhiX, were denatured and diluted according to the MiSeq System Denature and Dilute Libraries Guide. Samples were sequenced using Illumina Miseq with 2×250 bp reads. The V4 region of the 16S rRNA was sequenced with approximately 100,000 reads per sample. Sequences were mapped to Amplicon Sequence Variants (ASVs) using DADA2 (Callahan, et al., Nat. Methods, 2016, 13: 581-583). Forward reads were truncated at 240 bp, reverse reads were truncated at 160 bp, and reads with maximum expected error >2 were filtered out. Taxonomy was assigned to each ASV using the Ribosomal Database Project (RDP) classifier (release 11.5, (Wang, et al., Appl. Environ. Microbiol., 2007, 73: 5261-5267). ASVs were filtered for 5% prevalence using phyloseq (McMurdie, et al., PLoS One, 2013, 8:e61217) and differential expression of ASVs was evaluated using DESeq2 (Love, et al., Genome. Biol., 2014, 15: 550).

Results

Figures 3A, 3B:
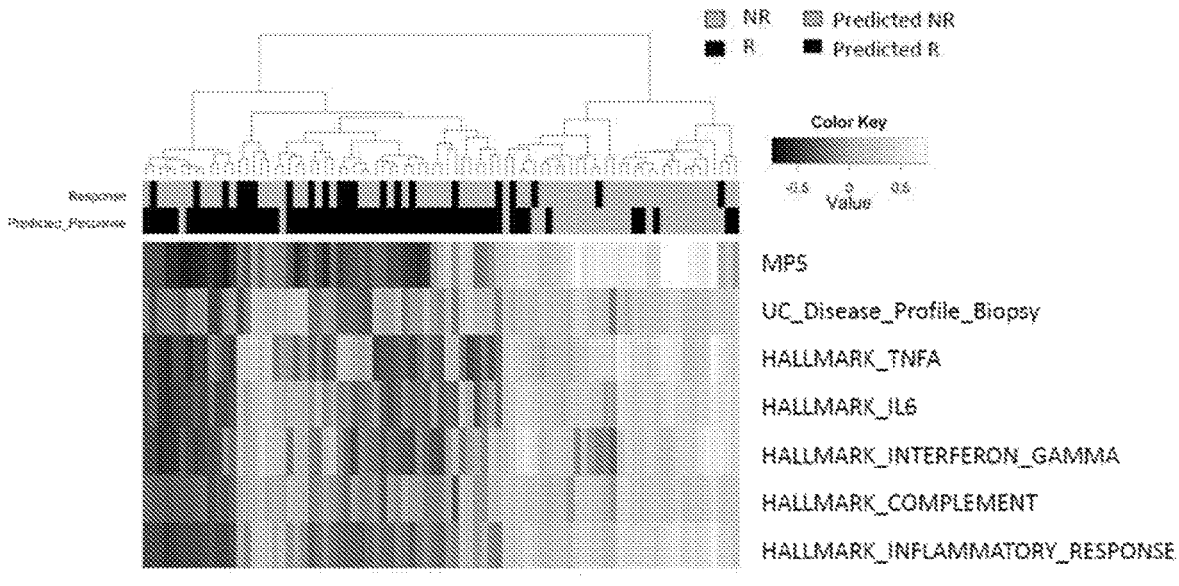
FIGS. 3A-3B show gene expression analysis of colonic biopsies collected from predicted non-responsive (NR) and predicted responsive (R) in PROgECT: number of genes differentially expressed (FC>2, FDR<0.05) between predicted NR and predicted R patients and between true NR and true R patients (FIG. 3A); heatmap of Gene set variation analysis (GSVA) signature Scores (FIG. 3B); top 10 ingenuity pathways using genes differentially expressed between predicted NR and predicted R patients (Table 7).

Biomarker Analysis of Non-responders Predicted by the MPS in PROgECT: Gene expression differences between predicted non-responder and predicted responder patients at baseline was compared and 381 significant differentially expressed probe sets, representing 268 genes were identified (FIG. 3A, fold change >2, P<0.05). Pathway analysis of these 268 genes showed enrichment in predicted non-responders of inflammatory pathways including "Granulocyte/Agranulocyte Adhesion and Diapedesis", "Osteoarthritis Pathway", "Hepatic Fibrosis", "Role of Macrophages, Fibroblasts and Endothelial Cells in Rheumatoid Arthritis", and "Role of Pattern Recognition Receptors in Recognition of Bacteria and Viruses" (Table 9).

TABLE 9

Top 10 Ingenuity pathways using genes differentially expressed between predicted non-responder (N = 26) and predicted responder (N = 57) patients.

| Ingenuity Canonical Pathways | -log(p-value) |
| --- | --- |
| Granulocyte Adhesion and Diapedesis | 24.1 |
| Agranulocyte Adhesion and Diapedesis | 16.2 |
| Osteoarthritis Pathway | 12.2 |
| Role of Macrophages, Fibroblasts and Endothelial Cells in Rheumatoid Arthritis | 10.6 |
| Hepatic Fibrosis/Hepatic Stellate Cell Activation | 10.2 |
| Inhibition of Matrix Metalloproteases | 9.31 |
| Atherosclerosis Signaling | 8.55 |
| Bladder Cancer Signaling | 7.94 |
| Role of Pattern Recognition Receptors in Recognition of Bacteria and Viruses | 7.17 |
| HMGB1 Signaling | 7.1 |

By contrast, no significant differentially expressed probes were observed when comparing true non-responder to responder patients. Additionally, GSVA enrichment scores were generated for each patient using signatures that included genes from the MPS, a UC disease profile (i.e., diseased vs. healthy controls), inflammatory response genes, and specific signaling pathway genes. FIG. 3B shows that the predicted non-responder patients had significantly higher GSVA scores than predicted responders (P<0.05).

Figure 4A:
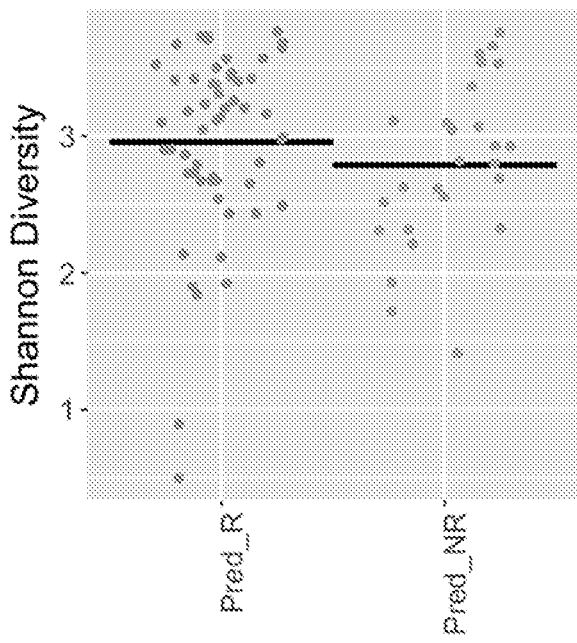
FIGS. 4A-4B show 16S fecal microbiome analysis of predicted NR and predicted R patients in PROgECT: Shannon diversity index comparing predicted NR and predicted R patients (p>0.05) (FIG. 4A), and ASVs differentially expressed between predicted NR and predicted R patients (FIG. 4B) at a FDR cut-off of 0.005.
Figure 4B:
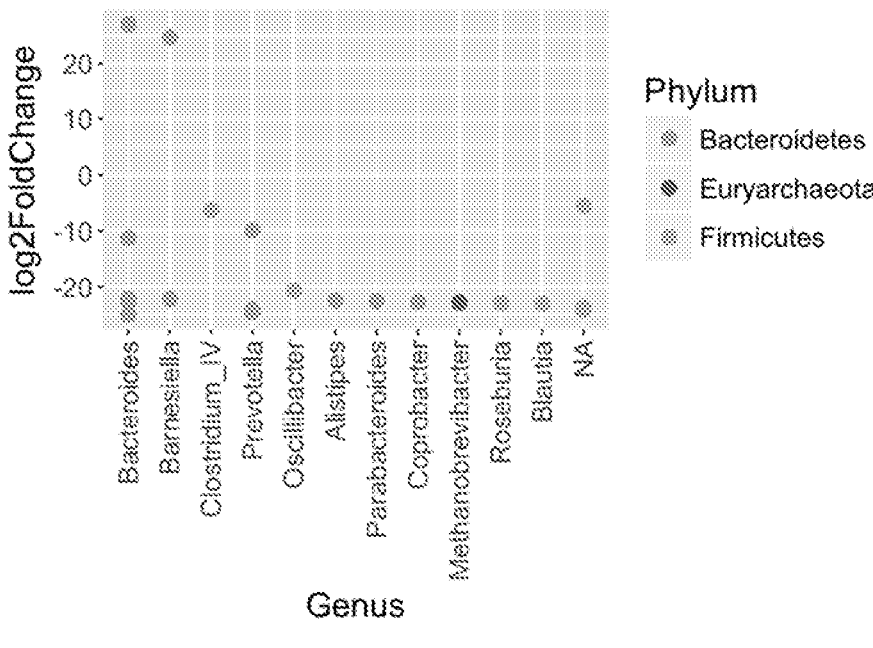

The gut microbiome is dysregulated in IBD patients and the extent of this dysregulation can be an indicator of disease severity. Comparing the fecal 16S microbiome profiles of predicted non-responder and predicted responder patients at baseline demonstrated that alpha diversity (Shannon diversity index) was not significantly different (FIG. 4A). However, a comparison between the two patient populations in the abundances of specific bacterial taxa yielded 22 significantly different alternative sequence variants (ASVs, FDR<0.05) (FIG. 4B).

The results showed that the predicted non-responder patients have molecular characteristics that are reflective of a high disease burden with microbial dysbiosis and high levels of inflammatory activity. These results provide insight into disease state of non-responder subjects and for selecting treatment options for these patients. We propose that these subjects, due to the higher inflammatory burden and severe nature of their disease, would be good candidates for therapies with mechanisms of action that are different from traditional cytokine blockers such as anti-TNF. Alternatively, these non-responder subjects could be good candidates for combination therapy approaches using two therapies with complementary mechanisms of action. The pathway analysis in Table 9 provides the types of pathways that may need to be targeted in these non-responder subjects. For example, therapies targeting cell types involved in intestinal tissue damage in IBD, such as fibroblasts and endothelial cells, may be beneficial to these non-responder subjects. Additionally, therapies targeting bacterial defense pathways may be beneficial. The MPS can therefore be used in selecting a subset of patients for future clinical trials with either monotherapy or combination therapies that target these types of pathways.

Example 6: Predictive Ability of Subsets of the 13-Gene MPS

The ability of a subset of these 13 MPS genes to predict endoscopic improvement in the PURSUIT trial was tested.

Methods and Materials

Microarray data was generated using Affymetrix HT HG-U133+ PM Array and normalized using the robust multi-chip average (RMA) method. Duplicate probesets for genes were removed so that 13 individual probesets were used to represent the 13 genes in the MPS (Table 10).

TABLE 10

Microarray Sequences (Affymetrix HT HG-U133+ PM Array).

| SEQ ID NO. | Probe Set ID | Gene Symbol | Sequence |
| --- | --- | --- | --- |
| 1 | 204422_PM_s_at | FGF2 | ATATCTTCTTCAGGCTCTGACAGGC |
| 2 | 209960_PM_at | HGF | ACTGGTTTTGCAATATAGAGATCAT |
| 3 | 211100_PM_x_at | LILRA2 | GGAAAGAACGTGACCCTGCTGTGTC |
| 4 | 211546_PM_x_at | SNCA | GAGGGTGTTCTCTATGTAGTGGCTG |
| 5 | 212657_PM_s_at | IL1RN | GGTACTATGTTAGCCCCATAATTTT |
| 6 | 215078_PM_at | SOD2 | CACATCTTGTTGACTGGAGGCATCT |
| 7 | 215977_PM_x_at | GK | GTGGAATTCCACTCAGTCATTTGCA |
| 8 | 220088_PM_at | C5AR1 | ATTATGCTTTCTATTTTGAGATCAT |
| 9 | 224941_PM_at | PAPPA | GTCTACTTAAGACTTCTGGTCATTT |
| 10 | 225987_PM_at | STEAP4 | GTGCTTTGGGCGAACTGTATTCCTT |
| 11 | 229967_PM_at | CMTM2 | CCATCTTGAGGCTTATCATCACCAT |

TABLE 10-continued

Microarray Sequences (Affymetrix HT HG-U133+
PM Array).

| SEQ ID NO. | Probe Set ID | Gene Symbol | Sequence |
|---|---|---|---|
| 12 | 235109_PM_at | ZBED3 | AAAACCATGCTTTCCTTGATTTCTC |
| 13 | 243296_PM_at | NAMPT | AGATCTGAGACTACCTCGAGGAGTA |

Results

There were a total of 31 non-responders and 28 responders by Week 6 endoscopic improvement. A logistic regression model was built using 13 genes of the MPS or a subset of the 13 genes to predict endoscopic improvement. The full 13 gene model could predict endoscopic improvement with an area under the curve (AUC) of 0.78 (Table 11). Reducing the model to 8 genes (0.77), or 4 genes (0.73), did not dramatically decrease the accuracy of the model (Table 11). Building a model with the single genes to predict endoscopic improvement still gave an AUC of over 0.7 (Table 11).

TABLE 11

Predictive Ability of Subsets of the 13-Gene MPS

| Genes in Model | AUC |
|---|---|
| 13 genes | 0.78 |
| 8 genes (IL1RN, NAMPT, STEAP4, HGF, SNCA, SOD2, GK, C5AR1) | 0.77 |
| 4 genes (IL1RN, NAMPT, STEAP4, HGF) | 0.73 |
| 4 genes (IL1RN, PAPPA, NAMPT, LILRA2) | 0.73 |
| IL1RN | 0.72 |
| PAPPA | 0.70 |

These results demonstrate that gene sets that consist of less than the full 13 genes still have predictive capability for endoscopic improvement.

Example 7: Performance of the 13-Gene MPS in Peripheral Blood Samples

The objective of this study was to test whether peripheral blood from patients can be used to predict response to treatment using the 13-gene MPS.

In the PURSUIT study, 2.5 mL blood samples were collected at week 0 (pre-treatment) using PAXgene tubes. Following collection, the blood samples were stored at 80° C. until RNA isolation was performed. Total RNA plus miRNA was extracted with PAXgene Blood RNA MDx Kit plus customized reagent BM3 (Cat #762431, lot 136255926) according to the manufacturer's instructions (Qiagen Inc., Valencia, CA). Briefly, PAXgene Blood RNA Tubes were incubated at room temperature approximately 2 hrs before extraction. After centrifugation for 10 min at 3000-5000× g, the pellets were resuspended in 290 µl Buffer BR1 with 35 µl proteinase K. The remaining procedures were performed on BioRobot Universal System. RNA samples were amplified by NuGEN Ovation RNA Amplification System V2 Whole Blood solution (NuGEN, San Carlos, CA), and purified using Agencourt RNAClean magnetic beads (Agencourt, Beverly, MA) on a Caliper SciClone robot. Labeling was done using the NuGEN Encore Biotin Module (NuGEN). Samples were hybridized to Affymetrix GeneChip HT HGU133+ PM 96-Array plates (Affymetrix, Santa Clara, CA, Cat #901262, lot 413123) for 16 hours at 48° C. according to the manufacturer's protocol with the exception of DMSO replacing TMAC (Tetramethylammonium Chloride Solution) in the hybridization buffer. Arrays were washed and stained on the Affymetrix GeneChip Array Station, then scanned on an HTAPS scanner.

After quality control, there were 11 genes from within the 13 gene panel which were present in the PURSUIT blood data set. As there was not enough data to be able to build reliable models (66 subjects), 34 more synthetic subjects were generated based on the actual data and the modeling was done based on a total on 66 real and 34 synthetic data points. A total of 35 different models were built and the best performing model was selected. Performance of model was tested using the 5-fold cross validation frame work.

Figure 5:
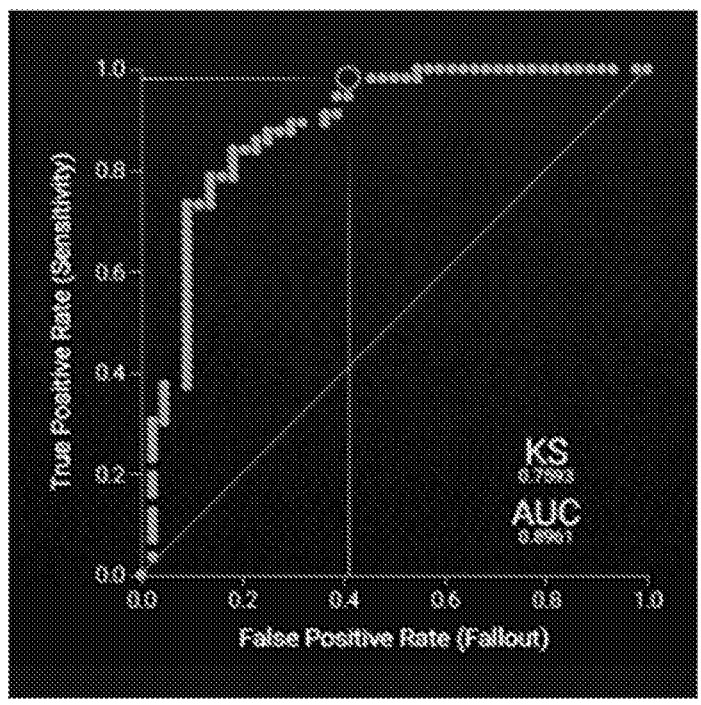
FIG. 5 shows the performance of the MPS model as measured in whole blood gene expression in the PURSUIT cohort (AUC of 0.90).

The best performing model was a rule-based classifier (FIG. 5). The algorithm fit rule-based models first by fitting a generalized boosted model (GBM) to the input data. The trees of the GBM were then extracted as simple binary rules, and the input dataset was encoded as 0/1 binary variables, representing whether or not the rule is in effect for a given input point. After the data was encoded using the rules, the algorithm fit an L1-penalized (lasso) logistic regression model using the rules as inputs and the target as an output. To predict on new data, it was first encoded using the rules and then the coefficients from the logistic regression model were applied.

In PURSUIT the Sensitivity of this model was 0.98, Specificity was 0.59, Positive Predictive Value was 0.75, and Negative Predictive Value was 0.96. These results demonstrate that it is possible to translate the performance of MPS from tissue (colon biopsy) to blood.

Example 8: Methodology of Calculating MPS Score

Data for clinical samples and controls (profiled in triplicate) were loaded into GenEx for pre-processing. Any values >25 cycles were removed then the data were efficiency corrected. Missing data points were replaced with a temporary large value (100) then outliers were found and removed (standard deviation 0.25, Grubb's test p-value 0.8).

Technical replicates were averaged then any values >30 were removed. A group of reference genes were selected based on their expression stability across previous cohorts and were run alongside the 13 signature genes. Same rules of handling missing value and outliers were applied to reference genes data process. The delta Cq value of 13 signature genes were obtained through normalizing to the reference genes. The samples with high missing data rate were removed prior to analysis.

Grubb's Test for Outliers:

$$\frac{|Ct - \overline{Ct}|}{s} > \frac{N-1}{\sqrt{N}} \sqrt{\frac{\left(t_{\alpha/2N,N-2}\right)^2}{N-2+\left(t_{\alpha/2N,2N}\right)^2}}$$

Delta Cq data for the patient samples was inverted for analysis (−deltaCq) and the PURSUIT 13 gene Naïve Bayes model (Table 12) was applied to calculate a signature score for each sample and classifies the sample based on a threshold.

TABLE 12

| Configuration parameters of PURSUIT 13 gene Naive Bayes model | | | | |
|---|---|---|---|---|
| Gene i | XBTESTCD | $x_{i0}$ | $x_{i1}$ | $s_i$ |
| GK__JC1 | GKN | −0.654555579306452 | −1.130499887107140 | 0.612446640134252 |
| FGF2__JC1 | FGF2N | −2.100036769532260 | −2.988364540571430 | 0.986379819909083 |
| HGF | HGFN | −1.977545671096770 | −2.976187467803570 | 1.053290489064460 |
| ZBED3 | ZBED3N | −3.485514691338710 | −3.294534637892860 | 0.376792877109258 |
| CMTM2 | CMTM2N | −7.783099208661290 | −8.356577307107140 | 0.774518086020830 |
| NAMPT | NAMPTN | 2.541782593500000 | 1.625816028071430 | 0.917565448057176 |
| IL1RN | IL1RN | 1.743165946919350 | 0.570590981500000 | 1.079513997153800 |
| LILRA2__JC1 | LILRA2N | −2.574509446677420 | −3.695475940142860 | 1.160264409824710 |
| SNCA | SNCAN | −1.549037488774190 | −2.211029210928570 | 0.793532087771329 |
| C5AR1__CLT | C5AR1N | −2.949766796967740 | −3.945219031071430 | 0.977955890287082 |
| PAPPA | PAPPAN | −2.016585409370970 | −3.115274212803570 | 1.084255701977760 |
| SOD2 | SOD2N | 4.246135594532260 | 3.435486254553570 | 0.840541122484868 |
| STEAP4 | STEAP4N | −0.814238545048387 | −1.821983996750000 | 1.001925281749200 |

In Table 12, $x_i$ is the $-\Delta Cq$ expression of gene i; $[\overline{x}_{i0}, \overline{x}_{i1}]$ are the group means of each gene i in T17 non-responder and responder group respectively; $s_i$ is the pooled within group variance for gene i and the constant term Log DetSigma=−3.77796. The formulae below were used to calculate the value based on mean of two response conditions.

$$A = \ln(0.5) - 0.5 \times \left( \sum_{i=1}^{13} \left( \frac{x_i - \overline{x}_{i1}}{s_i} \right)^2 + LogDetSigma \right)$$

$$B = \ln(0.5) - 0.5 \times \left( \sum_{i=1}^{13} \left( \frac{x_i - \overline{x}_{i0}}{s_i} \right)^2 + LogDetSigma \right)$$

Then A and B are then transformed using a scaling factor defined by the following equations:

$A\_Transform = \exp(A - \max(A,B))$ $B\_Transform = \exp(B - \max(A,B))$

The transformed values for A and B are then used to calculate a probability of A and a probability of B where:

$$Pr(A) = \frac{A\_Transform}{A\_Transform + B\_Transform}$$

$$Pr(B) = \frac{B\_Transform}{A\_Transform + B\_Transform}$$

The probability scores are subject to a final transformation to the log it scale, to enable a more accurate evaluation of the signature's analytical properties. The equations below are followed to generate the final log it transformed signature score:

If $Pr(A) < 0.5$ $$\text{Final Signature Score} = (+)\ln\left( \frac{Pr(A)}{1 - Pr(A)} \right)$$

If $Pr(B) > 0.5$ $$\text{Final Signature Score} = (-)\ln\left( \frac{Pr(B)}{1 - Pr(B)} \right)$$

The 13 gene Naïve Bayes signature is a probability-based model, whereby the signature score is the log it transformed probability of responder class membership. Once the final signature score has been calculated this should be dichotomized at the threshold.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

All documents cited herein are incorporated by reference.

It is claimed:

1. A method of treating a subject diagnosed with an inflammatory bowel disease (IBD), comprising:

(i) identifying a subject diagnosed with an IBD to be a responder to an IBD treatment comprising an anti-interleukin 23 (anti-IL23) antibody, the method comprising:

a). contacting a sample from a subject with a set of probes capable of detecting a panel of biomarkers comprising 13 biomarkers selected from the group consisting of CKLF-like MARVEL transmembrane domain containing 2 (CMTM2), complement C5a receptor 1 (C5AR1), fibroblast growth factor 2 (FGF2), glycerol kinase (GK), hepatocyte growth factor (HGF), interleukin 1 receptor antagonist (IL1RN), leukocyte immunoglobulin like receptor A2 (LILRA2), nicotinamide phosphoribosyltransferase (NAMPT), pappalysin 1 (PAPPA), synuclein alpha (SNCA), superoxide dismutase 2, mitochondrial (SOD2), STEAP4 metalloreductase (STEAP4), and zinc finger BED-type containing 3 (ZBED3);

b). determining a signature score of the panel of biomarkers, wherein the determining comprises determining the baseline gene expression levels of the panel of biomarkers; and c). identifying a subject to be a responder to the IBD treatment if the signature score of the panel of biomarkers is above a pre-specified threshold indicative of response; and (ii) administering to the subject who has been identified as a responder in c) a therapeutically effective amount of the IBD treatment.

2. The method of claim 1, wherein a. the sample is obtained before the subject is treated with the IBD treatment; or b. the probe is selected from the group consisting of an aptamer, an antibody, an affibody, a peptide, and a nucleic acid.

3. The method of claim 2, wherein the probe is a nucleic acid.

4. The method of claim 2, wherein the probe is selected from the group consisting of SEQ ID NOS. 1-14, SEQ ID NO. 17, SEQ ID NO. 20, SEQ ID NO. 23, SEQ ID NO. 26, SEQ ID NO. 29, SEQ ID NO. 32, SEQ ID NO. 35, SEQ ID NO. 38, SEQ ID NO. 41, SEQ ID NO. 44, SEQ ID NO. 47, and SEQ ID NO. 50.

5. The method of claim 1, wherein the gene expression levels of the panel of biomarkers are determined by quantitative polymerase chain reaction (qPCR).

6. The method of claim 5, wherein the qPCR primers are selected from the group consisting of SEQ ID NO. 15, SEQ ID NO. 16, SEQ ID NO. 18, SEQ ID NO. 19, SEQ ID NO. 21, SEQ ID NO. 22, SEQ ID NO. 24, SEQ ID NO. 25, SEQ ID NO. 27, SEQ ID NO. 28, SEQ ID NO. 30, SEQ ID NO. 31, SEQ ID NO. 33, SEQ ID NO. 34, SEQ ID NO. 36, SEQ ID NO. 37, SEQ ID NO. 39, SEQ ID NO. 40, SEQ ID NO. 42, SEQ ID NO. 43, SEQ ID NO. 45, SEQ ID NO. 46, SEQ ID NO. 48, SEQ ID NO. 49, SEQ ID NO. 51, and SEQ ID NO. 52.

7. The method of claim 1, wherein the pre-specified threshold level is a. selected from the group consisting of between-3.9000 and 1.1000;

b. −3.8234; or c. 1.0000.

8. The method of claim 1, further comprising predicting the response by one or more other characteristics of the subject.

9. The method of claim 8, wherein the other characteristics are selected from the group consisting of protein levels, gut microbiome, histology and clinical characteristics of the subject.

10. The method of claim 1, further comprising measuring the response at or after week 6, 30 or 50 of the IBD treatment, or anytime in between.

11. The method of claim 1, wherein the sample is a tissue sample or a blood sample.

12. The method of claim 1, wherein the IBD is at least one of ulcerative colitis (UC) or Crohn's disease (CD).

13. The method of claim 1, wherein the subject had previously failed or were intolerant of at least one therapy selected from the group consisting of: vedolizumab, corticosteroids, azathioprine (AZA), and 6 mercaptopurine (6 MP), or the subject had demonstrated corticosteroid dependence.

14. The method of claim 1, wherein the anti-IL23 antibody is ustekinumab.

* * * * *

SEQUENCE LISTING

```
<160> NUMBER OF SEQ ID NOS: 64

<210> SEQ ID NO 1
<211> LENGTH: 25
<212> TYPE: DNA
<213> ORGANISM: Homo sapiens
<220> FEATURE:
<223> OTHER INFORMATION: 204422_PM_s_at (Gene Name: FGF2)

<400> SEQUENCE: 1
atatcttctt caggctctga caggc                                      25

<210> SEQ ID NO 2
<211> LENGTH: 25
```

-continued

```
<212> TYPE: DNA
<213> ORGANISM: Homo sapiens
<220> FEATURE:
<223> OTHER INFORMATION: 209960_PM_at (Gene name: HGF)

<400> SEQUENCE: 2
actggttttg caatatagag atcat                                             25

<210> SEQ ID NO 3
<211> LENGTH: 25
<212> TYPE: DNA
<213> ORGANISM: Homo sapiens
<220> FEATURE:
<223> OTHER INFORMATION: 211100_PM_x_at (Gene name: LILRA2)

<400> SEQUENCE: 3
ggaaagaacg tgaccctgct gtgtc                                             25

<210> SEQ ID NO 4
<211> LENGTH: 25
<212> TYPE: DNA
<213> ORGANISM: Homo sapiens
<220> FEATURE:
<223> OTHER INFORMATION: 211546_PM_x_at (Gene name: SNCA)

<400> SEQUENCE: 4
gagggtgttc tctatgtagt ggctg                                             25

<210> SEQ ID NO 5
<211> LENGTH: 25
<212> TYPE: DNA
<213> ORGANISM: Homo sapiens
<220> FEATURE:
<223> OTHER INFORMATION: 212657_PM_s_at (Gene name: IL1RN)

<400> SEQUENCE: 5
ggtactatgt tagccccata atttt                                            25

<210> SEQ ID NO 6
<211> LENGTH: 25
<212> TYPE: DNA
<213> ORGANISM: Homo sapiens
<220> FEATURE:
<223> OTHER INFORMATION: 215078_PM_at (Gene name: SOD2)

<400> SEQUENCE: 6
cacatcttgt tgactggagg catct                                            25

<210> SEQ ID NO 7
<211> LENGTH: 25
<212> TYPE: DNA
<213> ORGANISM: Homo sapiens
<220> FEATURE:
<223> OTHER INFORMATION: 215977_PM_x_at (Gene name: GK)

<400> SEQUENCE: 7
gtggaattcc actcagtcat ttgca                                            25

<210> SEQ ID NO 8
<211> LENGTH: 25
<212> TYPE: DNA
<213> ORGANISM: Homo sapiens
<220> FEATURE:
<223> OTHER INFORMATION: 220088_PM_at (Gene name: C5AR1)

<400> SEQUENCE: 8
```

US 12,595,510 B2

-continued attatgcttt ctattttgag atcat                                          25

<210> SEQ ID NO 9
<211> LENGTH: 25
<212> TYPE: DNA
<213> ORGANISM: Homo sapiens
<220> FEATURE:
<223> OTHER INFORMATION: 224941_PM_at (Gene name: PAPPA)

<400> SEQUENCE: 9
gtctacttaa gacttctggt cattt                                          25

<210> SEQ ID NO 10
<211> LENGTH: 25
<212> TYPE: DNA
<213> ORGANISM: Homo sapiens
<220> FEATURE:
<223> OTHER INFORMATION: 225987_PM_at (Gene name: STEAP4)

<400> SEQUENCE: 10
gtgctttggg cgaactgtat tcctt                                          25

<210> SEQ ID NO 11
<211> LENGTH: 25
<212> TYPE: DNA
<213> ORGANISM: Homo sapiens
<220> FEATURE:
<223> OTHER INFORMATION: 229967_PM_at (Gene name: CMTM2)

<400> SEQUENCE: 11
ccatcttgag gcttatcatc accat                                          25

<210> SEQ ID NO 12
<211> LENGTH: 25
<212> TYPE: DNA
<213> ORGANISM: Homo sapiens
<220> FEATURE:
<223> OTHER INFORMATION: 235109_PM_at (Gene name: ZBED3)

<400> SEQUENCE: 12
aaaaccatgc tttccttgat ttctc                                          25

<210> SEQ ID NO 13
<211> LENGTH: 25
<212> TYPE: DNA
<213> ORGANISM: Homo sapiens
<220> FEATURE:
<223> OTHER INFORMATION: 243296_PM_at (Gene name: NAMPT)

<400> SEQUENCE: 13
agatctgaga ctacctcgag gagta                                          25

<210> SEQ ID NO 14
<211> LENGTH: 19
<212> TYPE: DNA
<213> ORGANISM: Homo sapiens
<220> FEATURE:
<223> OTHER INFORMATION: Probe Sequence of AID1URP (Gene name: GK_JC1)

<400> SEQUENCE: 14
cacgatggag cggtttgaa                                                 19

<210> SEQ ID NO 15
<211> LENGTH: 25
<212> TYPE: DNA
<213> ORGANISM: Homo sapiens -continued

```
<220> FEATURE:
<223> OTHER INFORMATION: F.Primer Sequence of AID1URP (Gene name:
     GK_JC1)

<400> SEQUENCE: 15
tcatcacagc tttcttccat gtaga                                              25

<210> SEQ ID NO 16
<211> LENGTH: 18
<212> TYPE: DNA
<213> ORGANISM: Homo sapiens
<220> FEATURE:
<223> OTHER INFORMATION: R.Primer Sequence of AID1URP (Gene name:
     GK_JC1)

<400> SEQUENCE: 16
attaatgcgg aggaaagt                                                      18

<210> SEQ ID NO 17
<211> LENGTH: 24
<212> TYPE: DNA
<213> ORGANISM: Homo sapiens
<220> FEATURE:
<223> OTHER INFORMATION: Probe Sequence of AIX01J5 (Gene name: FGF2_JC1)

<400> SEQUENCE: 17
caaaggagtg tgtgctaacc gtta                                               24

<210> SEQ ID NO 18
<211> LENGTH: 27
<212> TYPE: DNA
<213> ORGANISM: Homo sapiens
<220> FEATURE:
<223> OTHER INFORMATION: F.Primer Sequence of AIX01J5 (Gene name:
     FGF2_JC1)

<400> SEQUENCE: 18
acactcatcc gtaacacatt tagaagc                                            27

<210> SEQ ID NO 19
<211> LENGTH: 18
<212> TYPE: DNA
<213> ORGANISM: Homo sapiens
<220> FEATURE:
<223> OTHER INFORMATION: R.Primer Sequence of AIX01J5 (Gene name:
     FGF2_JC1)

<400> SEQUENCE: 19
tggctatgaa ggaagatg                                                      18

<210> SEQ ID NO 20
<211> LENGTH: 18
<212> TYPE: DNA
<213> ORGANISM: Homo sapiens
<220> FEATURE:
<223> OTHER INFORMATION: Probe Sequence of Hs00900073_m1 (Gene name:
     HGF)

<400> SEQUENCE: 20
caagtgcaag gacctacg                                                      18

<210> SEQ ID NO 21
<211> LENGTH: 25
<212> TYPE: DNA
<213> ORGANISM: Homo sapiens
<220> FEATURE:
<223> OTHER INFORMATION: F.Primer Sequence of Hs00900073_m1 (Gene name:
```

-continued

HGF)

<400> SEQUENCE: 21
cgagcatgac atgactcctg aaaat                                          25

<210> SEQ ID NO 22
<211> LENGTH: 25
<212> TYPE: DNA
<213> ORGANISM: Homo sapiens
<220> FEATURE:
<223> OTHER INFORMATION: R.Primer Sequence of Hs00900073_m1 (Gene name:
      HGF)

<400> SEQUENCE: 22
ccatctggat ttcggcagta atttt                                         25

<210> SEQ ID NO 23
<211> LENGTH: 16
<212> TYPE: DNA
<213> ORGANISM: Homo sapiens
<220> FEATURE:
<223> OTHER INFORMATION: Probe Sequence of Hs00995410_m1 (Gene name:
      ZBED3)

<400> SEQUENCE: 23
cccgcacgct ttaaat                                                   16

<210> SEQ ID NO 24
<211> LENGTH: 20
<212> TYPE: DNA
<213> ORGANISM: Homo sapiens
<220> FEATURE:
<223> OTHER INFORMATION: F.Primer Sequence of Hs00995410_m1 (Gene name:
      ZBED3)

<400> SEQUENCE: 24
acagggaccc cagaatcctt                                               20

<210> SEQ ID NO 25
<211> LENGTH: 20
<212> TYPE: DNA
<213> ORGANISM: Homo sapiens
<220> FEATURE:
<223> OTHER INFORMATION: R.Primer Sequence of Hs00995410_m1 (Gene name:
      ZBED3)

<400> SEQUENCE: 25
gctcgccact cctcattctg                                               20

<210> SEQ ID NO 26
<211> LENGTH: 14
<212> TYPE: DNA
<213> ORGANISM: Homo sapiens
<220> FEATURE:
<223> OTHER INFORMATION: Probe Sequence of Hs00376242_g1 (Gene name:
      CMTM2)

<400> SEQUENCE: 26
cagcccaaac tccg                                                     14

<210> SEQ ID NO 27
<211> LENGTH: 21
<212> TYPE: DNA
<213> ORGANISM: Homo sapiens
<220> FEATURE:
<223> OTHER INFORMATION: F.Primer Sequence of Hs00376242_g1 (Gene name:
      CMTM2)

<400> SEQUENCE: 27
gggcacgctg agatcaagat t                                             21

<210> SEQ ID NO 28
<211> LENGTH: 25
<212> TYPE: DNA
<213> ORGANISM: Homo sapiens
<220> FEATURE:
<223> OTHER INFORMATION: R.Primer Sequence of Hs00376242_g1 (Gene name:
      CMTM2)

<400> SEQUENCE: 28
gaggacaaca gtatcattgc agcta                                         25

<210> SEQ ID NO 29
<211> LENGTH: 18
<212> TYPE: DNA
<213> ORGANISM: Homo sapiens
<220> FEATURE:
<223> OTHER INFORMATION: Probe Sequence of Hs00237184_m1 (Gene name:
      NAMPT)

<400> SEQUENCE: 29
cgactcctac aaggttac                                                 18

<210> SEQ ID NO 30
<211> LENGTH: 22
<212> TYPE: DNA
<213> ORGANISM: Homo sapiens
<220> FEATURE:
<223> OTHER INFORMATION: F.Primer Sequence of Hs00237184_m1 (Gene name:
      NAMPT)

<400> SEQUENCE: 30
cagaagccga gttcaacatc ct                                            22

<210> SEQ ID NO 31
<211> LENGTH: 25
<212> TYPE: DNA
<213> ORGANISM: Homo sapiens
<220> FEATURE:
<223> OTHER INFORMATION: R.Primer Sequence of Hs00237184_m1 (Gene name:
      NAMPT)

<400> SEQUENCE: 31
gcttgtgttg ggtggatatt gttta                                         25

<210> SEQ ID NO 32
<211> LENGTH: 18
<212> TYPE: DNA
<213> ORGANISM: Homo sapiens
<220> FEATURE:
<223> OTHER INFORMATION: Probe Sequence of Hs00893626_m1 (Gene name:
      IL1RN)

<400> SEQUENCE: 32
ctggaggcag ttaacatc                                                 18

<210> SEQ ID NO 33
<211> LENGTH: 23
<212> TYPE: DNA
<213> ORGANISM: Homo sapiens
<220> FEATURE:
<223> OTHER INFORMATION: F.Primer Sequence of Hs00893626_m1 (Gene name:
      IL1RN)

-continued

```
<400> SEQUENCE: 33
ctgtgtcaag tctggtgatg aga                                        23

<210> SEQ ID NO 34
<211> LENGTH: 20
<212> TYPE: DNA
<213> ORGANISM: Homo sapiens
<220> FEATURE:
<223> OTHER INFORMATION: R.Primer Sequence of Hs00893626_m1 (Gene name:
      IL1RN)

<400> SEQUENCE: 34
ctgttctcgc tcaggtcagt                                            20

<210> SEQ ID NO 35
<211> LENGTH: 24
<212> TYPE: DNA
<213> ORGANISM: Homo sapiens
<220> FEATURE:
<223> OTHER INFORMATION: Probe Sequence of AIFASXX (Gene name:
      LILRA2_JC1)

<400> SEQUENCE: 35
cagccacaat cactcatcag agta                                       24

<210> SEQ ID NO 36
<211> LENGTH: 22
<212> TYPE: DNA
<213> ORGANISM: Homo sapiens
<220> FEATURE:
<223> OTHER INFORMATION: F.Primer Sequence of AIFASXX (Gene name:
      LILRA2_JC1)

<400> SEQUENCE: 36
ggtttgctgt aggctcctgt ca                                         22

<210> SEQ ID NO 37
<211> LENGTH: 15
<212> TYPE: DNA
<213> ORGANISM: Homo sapiens
<220> FEATURE:
<223> OTHER INFORMATION: R.Primer Sequence of AIFASXX (Gene name:
      LILRA2_JC1)

<400> SEQUENCE: 37
tgaccccctg gagct                                                 15

<210> SEQ ID NO 38
<211> LENGTH: 15
<212> TYPE: DNA
<213> ORGANISM: Homo sapiens
<220> FEATURE:
<223> OTHER INFORMATION: Probe Sequence of Hs00240906_m1 (Gene name:
      SNCA)

<400> SEQUENCE: 38
ctcagccact gttgc                                                 15

<210> SEQ ID NO 39
<211> LENGTH: 19
<212> TYPE: DNA
<213> ORGANISM: Homo sapiens
<220> FEATURE:
<223> OTHER INFORMATION: F.Primer Sequence of Hs00240906_m1 (Gene name:
      SNCA)

<400> SEQUENCE: 39
```

-continued

```
ggagggagtg gtgcatggt                                               19

<210> SEQ ID NO 40
<211> LENGTH: 25
<212> TYPE: DNA
<213> ORGANISM: Homo sapiens
<220> FEATURE:
<223> OTHER INFORMATION: R.Primer Sequence of Hs00240906_m1 (Gene name:
      SNCA)

<400> SEQUENCE: 40
catttgtcac ttgctctttg gtctt                                        25

<210> SEQ ID NO 41
<211> LENGTH: 18
<212> TYPE: DNA
<213> ORGANISM: Homo sapiens
<220> FEATURE:
<223> OTHER INFORMATION: Probe Sequence of AIAAZ80 (Gene name:
      C5AR1_CLT)

<400> SEQUENCE: 41
ggcaggaggg accttcga                                                18

<210> SEQ ID NO 42
<211> LENGTH: 23
<212> TYPE: DNA
<213> ORGANISM: Homo sapiens
<220> FEATURE:
<223> OTHER INFORMATION: F.Primer Sequence of AIAAZ80 (Gene name:
      C5AR1_CLT)

<400> SEQUENCE: 42
gggtggtata attgaaggag ttc                                          23

<210> SEQ ID NO 43
<211> LENGTH: 17
<212> TYPE: DNA
<213> ORGANISM: Homo sapiens
<220> FEATURE:
<223> OTHER INFORMATION: R.Primer Sequence of AIAAZ80 (Gene name:
      C5AR1_CLT)

<400> SEQUENCE: 43
ccaggagacc agaacat                                                 17

<210> SEQ ID NO 44
<211> LENGTH: 18
<212> TYPE: DNA
<213> ORGANISM: Homo sapiens
<220> FEATURE:
<223> OTHER INFORMATION: Probe Sequence of Hs01032305_m1 (Gene name:
      PAPPA)

<400> SEQUENCE: 44
acactccgac cctatggc                                                18

<210> SEQ ID NO 45
<211> LENGTH: 19
<212> TYPE: DNA
<213> ORGANISM: Homo sapiens
<220> FEATURE:
<223> OTHER INFORMATION: F.Primer Sequence of Hs01032305_m1 (Gene name:
      PAPPA)

<400> SEQUENCE: 45
```

-continued gcagtgccct gatggctat                                                    19

<210> SEQ ID NO 46
<211> LENGTH: 21
<212> TYPE: DNA
<213> ORGANISM: Homo sapiens
<220> FEATURE:
<223> OTHER INFORMATION: R.Primer Sequence of Hs01032305_m1 (Gene name:
      PAPPA)

<400> SEQUENCE: 46
gatgatggac tcgctgttgt g                                                 21

<210> SEQ ID NO 47
<211> LENGTH: 17
<212> TYPE: DNA
<213> ORGANISM: Homo sapiens
<220> FEATURE:
<223> OTHER INFORMATION: Probe Sequence of Hs01553554_m1 (Gene name:
      SOD2)

<400> SEQUENCE: 47
ctcccctttg ggttctc                                                      17

<210> SEQ ID NO 48
<211> LENGTH: 21
<212> TYPE: DNA
<213> ORGANISM: Homo sapiens
<220> FEATURE:
<223> OTHER INFORMATION: F.Primer Sequence of Hs01553554_m1 (Gene name:
      SOD2)

<400> SEQUENCE: 48
ggacaaacct cagccctaac g                                                 21

<210> SEQ ID NO 49
<211> LENGTH: 21
<212> TYPE: DNA
<213> ORGANISM: Homo sapiens
<220> FEATURE:
<223> OTHER INFORMATION: R.Primer Sequence of Hs01553554_m1 (Gene name:
      SOD2)

<400> SEQUENCE: 49
agtcacgttt gatggcttcc a                                                 21

<210> SEQ ID NO 50
<211> LENGTH: 16
<212> TYPE: DNA
<213> ORGANISM: Homo sapiens
<220> FEATURE:
<223> OTHER INFORMATION: Probe Sequence of Hs01026582_m1 (Gene name:
      STEAP4)

<400> SEQUENCE: 50
tcggcaggtg tttgtg                                                       16

<210> SEQ ID NO 51
<211> LENGTH: 20
<212> TYPE: DNA
<213> ORGANISM: Homo sapiens
<220> FEATURE:
<223> OTHER INFORMATION: F.Primer Sequence of Hs01026582_m1 (Gene name:
      STEAP4)

<400> SEQUENCE: 51
gtcaggagca ctggatgcaa                                                   20

-continued

```
<210> SEQ ID NO 52
<211> LENGTH: 22
<212> TYPE: DNA
<213> ORGANISM: Homo sapiens
<220> FEATURE:
<223> OTHER INFORMATION: R.Primer Sequence of Hs01026582_m1 (Gene name:
      STEAP4)

<400> SEQUENCE: 52
cttggctttg ctgtcatttc ca                                           22

<210> SEQ ID NO 53
<211> LENGTH: 20
<212> TYPE: DNA
<213> ORGANISM: Homo sapiens
<220> FEATURE:
<223> OTHER INFORMATION: Probe Sequence of Hs00472881_m1 (Gene name:
      PUM1_A4)

<400> SEQUENCE: 53
ctgaatgatc tgatgttccc                                              20

<210> SEQ ID NO 54
<211> LENGTH: 21
<212> TYPE: DNA
<213> ORGANISM: Homo sapiens
<220> FEATURE:
<223> OTHER INFORMATION: F.Primer Sequence of Hs00472881_m1 (Gene name:
      PUM1_A4)

<400> SEQUENCE: 54
ggtgatcaat ggcgagacag t                                            21

<210> SEQ ID NO 55
<211> LENGTH: 23
<212> TYPE: DNA
<213> ORGANISM: Homo sapiens
<220> FEATURE:
<223> OTHER INFORMATION: R.Primer Sequence of Hs00472881_m1 (Gene name:
      PUM1_A4)

<400> SEQUENCE: 55
ggtcttctct gcaccatgat tgg                                          23

<210> SEQ ID NO 56
<211> LENGTH: 15
<212> TYPE: DNA
<213> ORGANISM: Homo sapiens
<220> FEATURE:
<223> OTHER INFORMATION: Probe Sequence of Hs99999908_m1 (Gene name:
      GUSB_A4)

<400> SEQUENCE: 56
cgtcggtgac tgttc                                                   15

<210> SEQ ID NO 57
<211> LENGTH: 22
<212> TYPE: DNA
<213> ORGANISM: Homo sapiens
<220> FEATURE:
<223> OTHER INFORMATION: F.Primer Sequence of Hs99999908_m1 (Gene name:
      GUSB_A4)

<400> SEQUENCE: 57
ctcatttgga attttgccga tt                                           22
```

-continued

```
<210> SEQ ID NO 58
<211> LENGTH: 22
<212> TYPE: DNA
<213> ORGANISM: Homo sapiens
<220> FEATURE:
<223> OTHER INFORMATION: R.Primer Sequence of Hs99999908_m1 (Gene name:
      GUSB_A4)

<400> SEQUENCE: 58
ccgagtgaag atccccctttt ta                                                      22

<210> SEQ ID NO 59
<211> LENGTH: 19
<212> TYPE: DNA
<213> ORGANISM: Homo sapiens
<220> FEATURE:
<223> OTHER INFORMATION: Probe Sequence of Hs02800695_m1 (Gene name:
      HPRT1_A4)

<400> SEQUENCE: 59
tcagtcctgt ccataatta                                                           19

<210> SEQ ID NO 60
<211> LENGTH: 25
<212> TYPE: DNA
<213> ORGANISM: Homo sapiens
<220> FEATURE:
<223> OTHER INFORMATION: F.Primer Sequence of Hs02800695_m1 (Gene name:
      HPRT1_A4)

<400> SEQUENCE: 60
gctgaggatt tggaaagggt gttta                                                    25

<210> SEQ ID NO 61
<211> LENGTH: 24
<212> TYPE: DNA
<213> ORGANISM: Homo sapiens
<220> FEATURE:
<223> OTHER INFORMATION: R.Primer Sequence of Hs02800695_m1 (Gene name:
      HPRT1_A4)

<400> SEQUENCE: 61
ccttcatcac atctcgagca agac                                                     24

<210> SEQ ID NO 62
<211> LENGTH: 22
<212> TYPE: DNA
<213> ORGANISM: Homo sapiens
<220> FEATURE:
<223> OTHER INFORMATION: Probe Sequence of Hs00914041_m1 (Gene name:
      IPO8_A2)

<400> SEQUENCE: 62
cagatacaag ctaaggaata ta                                                       22

<210> SEQ ID NO 63
<211> LENGTH: 25
<212> TYPE: DNA
<213> ORGANISM: Homo sapiens
<220> FEATURE:
<223> OTHER INFORMATION: F.Primer Sequence of Hs00914041_m1 (Gene name:
      IPO8_A2)

<400> SEQUENCE: 63
tgcccttgct cttcagtctt taatt                                                    25
```

-continued

```
<210> SEQ ID NO 64
<211> LENGTH: 19
<212> TYPE: DNA
<213> ORGANISM: Homo sapiens
<220> FEATURE:
<223> OTHER INFORMATION: R.Primer Sequence of Hs00914041_m1 (Gene name:
      IPO8_A2)

<400> SEQUENCE: 64
ggcctcacat gtggcttca                                                19
```